(12) United States Patent
Kwon et al.

(10) Patent No.: US 9,084,782 B2
(45) Date of Patent: Jul. 21, 2015

(54) CHEMICAL INHIBITORS OF CHOLESTEROL BIOSYNTHESIS AND VENOUS ANGIOGENESIS

(75) Inventors: Ohyun Kwon, Los Angeles, CA (US); Jau-Nian Chen, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/979,566

(22) PCT Filed: Jan. 17, 2012

(86) PCT No.: PCT/US2012/021574
§ 371 (c)(1),
(2), (4) Date: Jul. 12, 2013

(87) PCT Pub. No.: WO2012/097371
PCT Pub. Date: Jul. 19, 2012

(65) Prior Publication Data
US 2013/0289073 A1   Oct. 31, 2013

Related U.S. Application Data

(60) Provisional application No. 61/432,650, filed on Jan. 14, 2011.

(51) Int. Cl.
*A61K 31/445* (2006.01)
*A61K 31/18* (2006.01)
*A61K 31/4418* (2006.01)
*C07D 211/74* (2006.01)
*C07D 401/04* (2006.01)
*C07D 405/04* (2006.01)
*C07D 409/04* (2006.01)
*A61K 31/4436* (2006.01)
*A61K 45/06* (2006.01)
*C07D 211/96* (2006.01)
*A61K 31/435* (2006.01)

(52) U.S. Cl.
CPC ......... *A61K 31/4418* (2013.01); *A61K 31/4436* (2013.01); *A61K 45/06* (2013.01); *C07D 211/74* (2013.01); *C07D 211/96* (2013.01); *C07D 401/04* (2013.01); *C07D 405/04* (2013.01); *C07D 409/04* (2013.01); *A61K 31/18* (2013.01); *A61K 31/435* (2013.01)

(58) Field of Classification Search
CPC ............................. A61K 31/18; A61K 31/435
USPC .................................................... 514/601, 318
See application file for complete search history.

(56) References Cited

U.S. PATENT DOCUMENTS 5,858,024 A * 1/1999 De Lacharriere et al. ........ 8/408

FOREIGN PATENT DOCUMENTS

WO   WO-2007/111948 A2   10/2007
WO   WO-2010/014054 A1   2/2010

OTHER PUBLICATIONS

Choi et al., "Aplexone targets the HMG-CoA reductase pathway and differentially regulates arteriovenous angiogenesis", Developement, vol. 138, No. 6, Mar. 2011, p. 1173-1181.
Matsumura et al., "Synthetic study of manzamine B: synthesis of tricyclic central core by an asymmetric Diels-Alder and RCM Strategy", Tetrahedron Letters, vol. 48, 2007, p. 1265-1268.
Zhu et al., "An Expedient Phisphine-Catalyzed [4 + 2] Annulation: Synthesis of Highly Functionalized Tetrahydropyridines", J. AM. Chem. SOC., vol. 125, No. 16, 2003, p. 4716-4717.
Lu et al., "Phosphine-Catalyzed [4 + 2] Annulation: Synthesis of Ethyl 6-Phenyl-1-Tosyl-1,2,5,6-Tetrahydropyridine-3-Carboxylate", Org. Synth., vol. 86, 2009, p. 212-224.
Zhao et al., "Baylis-Hillman reactions of N-tosyl aldimines and aryl aldehydes with 3-methylpenta-3,4-dien-2-one", Org. Biomol. Chem., vol. 3, No. 20, 2005, p. 3686-3694.
International Search Report and Written Opinion in Application No. PCT/US2012/021574 mailed Aug. 7, 2012.

* cited by examiner

*Primary Examiner* — Kevin E Weddington
(74) *Attorney, Agent, or Firm* — Venable LLP; Stefan J. Kirchanski; Nancy J. Axelrod

(57) ABSTRACT

This invention relates, e.g., to a compound, aplexone, and pharmaceutically acceptable salts and solvates, and functional variants, thereof. Methods of using the compounds and pharmaceutical compositions comprising them, e.g. to inhibit angiogenesis and to reduce cellular cholesterol levels, are also included.

6 Claims, 12 Drawing Sheets

CHEMICAL INHIBITORS OF CHOLESTEROL BIOSYNTHESIS AND VENOUS ANGIOGENESIS

CROSS-REFERENCE TO RELATED APPLICATIONS

This application is a U.S. National Stage of Application No. PCT/US2012/021574, filed Jan. 17, 2012, which claims priority to U.S. Provisional Application No. 61/432,650 filed Jan. 14, 2011, the entire contents of which are hereby incorporated by reference.

This invention was made with Government support under Grant Nos. HL081700, GM071779 and GM081282, awarded by the National Institutes of Health. The Government has certain rights in this invention.

SEQUENCE LISTING

The instant application contains a Sequence Listing which has been submitted in ASCII format via EFS-Web and is hereby incorporated by reference in its entirety. Said ASCII copy, created on Jun. 27, 2013, is named 58086-352670_SL.txt and is 4,931 bytes in size.

BACKGROUND INFORMATION

Arterial and venous endothelial cells (ECs) exhibit distinct molecular characteristics at early developmental stages. Blood vessels are diverse in size, structure and function to suit the needs of their local tissue environment. Endothelial cells, the inner lining of the blood and lymphatic vessels, have instructive roles in specifying vascular architecture and physiology. Prior to the initiation of blood circulation, ECs have already assumed specific molecular characteristics based on their arterial or venous identities. For example, in zebrafish embryos, ECs of the dorsal aorta (DA) activate a transcriptional program involving expression of notch and ephrinB2a upon stimulation by VEGF, whereas ECs of the posterior cardinal vein (PCV) express a distinct set of genes such as ephB4 and flt4 (Lawson et al., 2001; Zhong et al., 2001; Lawson et al., 2002). Similarly, in mouse embryos, capillaries of arterial origin express ephrinB2 and those of venous origin express ephB4 (Wang et al., 1998). Disrupting this arteriovenous lineage-specific expression pattern blocks circulation, highlighting the essential role for arteriovenous identity in establishing blood circulation (Gerety et al., 1999; Gerety and Anderson, 2002).

In addition to the diversity in their transcriptional profiles, ECs exhibit different cellular behaviors according to their arteriovenous origins. In zebrafish, angioblasts migrate from their lateral position to the midline in two waves to form the vascular cord. It has been hypothesized that angioblasts destined to form the DA migrate first, whereas the angioblasts destined to form the PCV migrate at a later stage (Torres-Vazquez et al., 2003; Jin et al., 2005; Williams et al., 2010). A pathway involving signaling molecules such as VEGF, Notch, PI3K and Eph/ephrin then directs a dorsal migration of ECs to form DA and a ventral migration to form PCV (Herbert et al., 2009). The diversity in lineage-dependent cellular behavior is further evident in the differential timing of angiogenesis during the formation of the dorsoventrally positioned intersegmental vessels (ISVs) in the trunk. Two waves of ISV sprouting were noted in zebrafish depending on the origin of ECs (Isogai et al., 2003; Hogan et al., 2009; Ellertsdottir et al., 2010). The first wave occurs at around 20 hours post fertilization (hpf) when ECs of the DA migrate dorsally in response to signals including VEGF and Notch to form the primary, aorta-derived vascular network. The second wave occurs about sixteen hours later (36 hpf) when a new set of vascular sprouts emerges exclusively from the PCV. Some of these secondary sprouts connect with the primary ISVs, linking the posterior cardinal vein to the primary vascular network (Isogai et al., 2003; Hogan et al., 2009; Ellertsdottir et al., 2010). The distinct timings of the arterial-derived primary sprouts and the venous-derived secondary sprouts suggest that arterial and venous angiogenesis are differentially regulated during development.

How the distinct molecular identities of arteries and veins influence lineage-specific angiogenesis has not heretofore been well-studied. The optical clarity and rapid development of zebrafish embryos, along with the fact that they are fertilized externally, offer an excellent opportunity to conduct in vivo screens for compounds modulating biological processes of interest (Zon and Peterson, 2005; Walsh and Chang, 2006), such as such lineage-specific angiogenesis.

Many diseases or conditions exist which can be benefited by a reduction in angiogenesis or a lowering of cell cholesterol levels. There is a need for new agents that can accomplish such therapeutic results.

(A) A representative image of Western blot for total Rac1 in HUAECs and HUVECs. The same blot was probed with anti-β-actin antibody to verify equal loading. The average of the relative amounts of total Rac1 in HUAECs and HUVECs collected from four independent experiments is indicated under the Western blot (*, p<0.05). (B)

Graph illustrates the inhibitory effect of 50 µM NSC 23766, a Rac1 inhibitor, on HUVECs and HUAECs.

Figure 11:
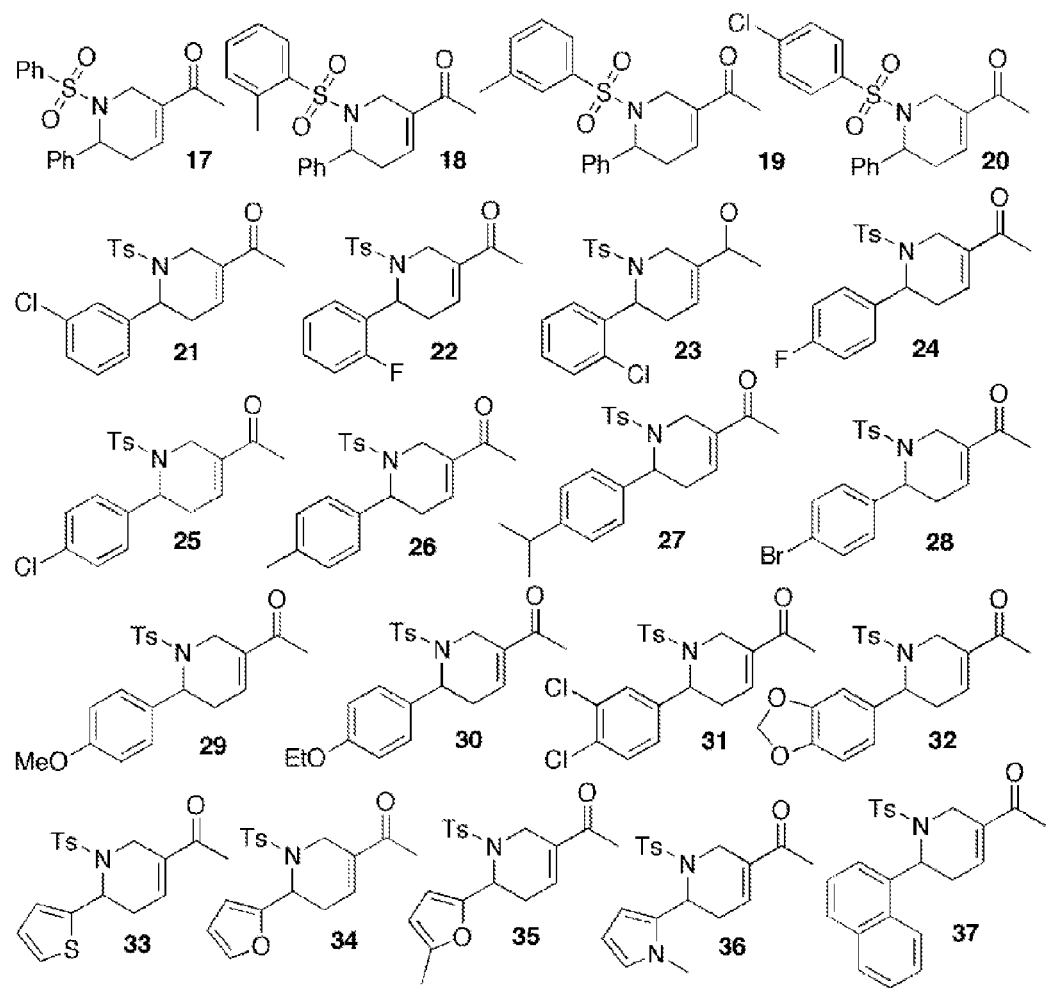

FIG. 11 shows the chemical structures of aplexone analogs 17-37.

Figure 12:
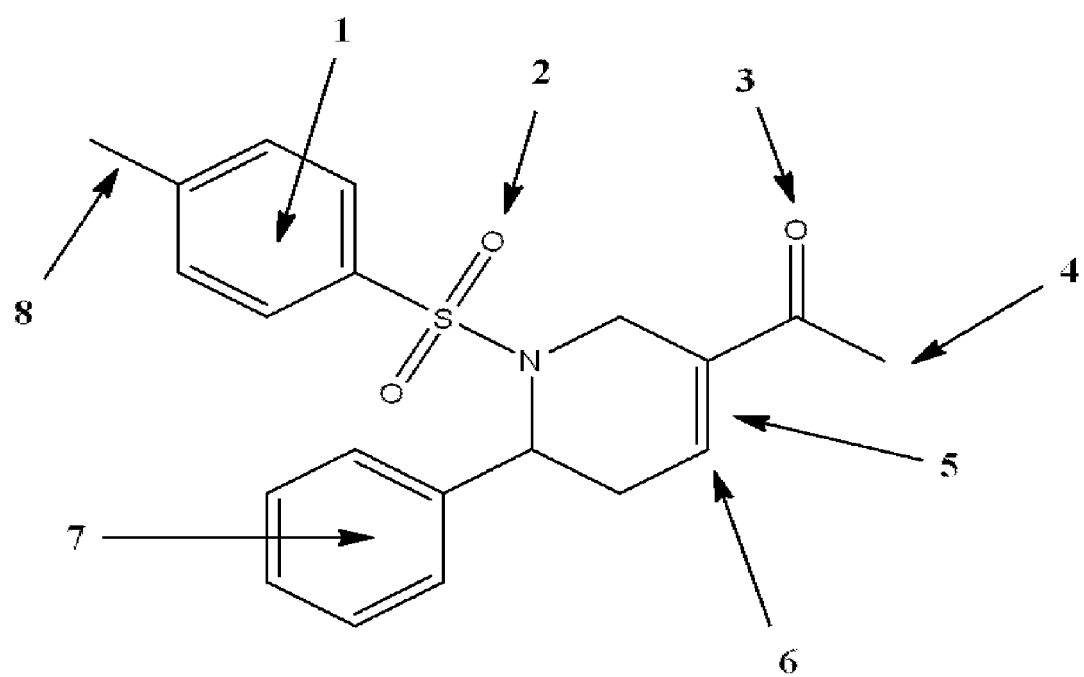

FIG. 12 shows a summary of the SAR data of aplexone.

DESCRIPTION

The present inventors have identified and characterized a group of small molecules including one called aplexone, and functional variants thereof, which, e.g., target the HMG-CoA reductase (HMGCR) pathway (e.g., elevate transcription of enzymes in the HMGCR pathway, which results in a decreased amount of HMGCR protein); effectively suppress angiogenesis, particularly venous angiogenesis (rather than arterial angiogenesis); inhibit prenylation (both farnesylation and geranylgeranylation) of cellular proteins (e.g., ras and rhoA); block cell proliferation and migration; and reduce cellular cholesterol levels. Studies are described in an embryonic zebrafish model (in vivo) and in cultured human endothelial cells [human umbilical vein cells (HUVECs) and human umbilical artery cells (HUAECs)].

The compounds of the invention are useful, for example, for treating angiogenesis-mediated conditions, such as cancer, and for treating subjects in need of lowering their cholesterol levels.

Advantages of aplexone and its functional variants include, e.g., its high degree of effectiveness in inhibiting angiogenesis and reducing cellular cholesterol levels, low toxicity, small molecular weight and ease of synthesis.

One aspect of the invention is a compound of formula I,

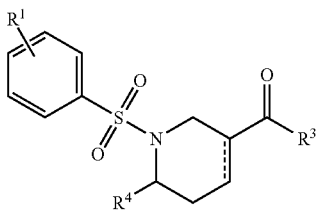

Formula I wherein the dashed bond indicates that a double bond may be present at the indicated location, or the ring may be saturated.

$R^1$ may be at any position on the phenyl ring and may be hydrogen, halogen, nitro, $(C_1-C_4)$alkyl, $(C_1-C_4)$haloalkyl, O—$(C_1-C_4)$alkyl (alkoxy), S—$(C_1-C_4)$alkyl (alkylthio) or NH—$(C_1-C_4)$alkyl (alkylamino). In some embodiments, $R^1$ may be hydrogen, halogen, $(C_1-C_4)$alkyl, or O—$(C_1-C_4)$alkyl. In some embodiments, $R^1$ may be hydrogen, chloride, or methyl.

$R^4$ may be hydrogen, halogen, nitro, $(C_1-C_4)$alkyl, $(C_1-C_4)$haloalkyl, O—$(C_1-C_4)$alkyl (alkoxy), S—$(C_1-C_4)$alkyl (alkylthio), NH—$(C_1-C_4)$alkyl (alkylamino), or Ar. In some embodiments $R^4$ is hydrogen or Ar. In some embodiments, $R^4$ is hydrogen, phenyl, or thiophene.

Ar may be an aryl or heteroaryl moiety, which may bear one or more substituents $R^2$. In some embodiments, Ar may be a 5-10 membered aryl or heteroaryl moiety. In some embodiments, Ar may be a 5-6 membered aryl or heteroaryl moiety. In some embodiments, Ar may be phenyl or thiophene.

$R^2$ may be at any available position on the aryl or heteroaryl moiety Ar and may be hydrogen, halogen, nitro, $(C_1-C_4)$alkyl, $(C_1-C_4)$haloalkyl, O—$(C_1-C_4)$alkyl (alkoxy), S—$(C_1-C_4)$alkyl (alkylthio) or NH—$(C_1-C_4)$alkyl (alkylamino). In some embodiments, $R^2$ may be at the ortho or meta position. In some embodiments, $R^2$ may be hydrogen, halogen, $(C_1-C_4)$alkyl, or O—$(C_1-C_4)$alkyl in the ortho or meta positions. In some embodiments, $R^2$ may be hydrogen, fluoro, or chloro, in the ortho or meta positions. In some embodiments, if $R^2$ is at the para position, $R^2$ may be any substituent except fluoro, chloro, bromo, isopropyl, methoxy or ethoxy. In some embodiments where $R^2$ is at the para position, $R^2$ may be hydrogen or methyl.

$R^3$ may be $(C_1-C_6)$alkyl, $(C_1-C_6)$haloalkyl, O—$(C_1-C_6)$alkyl, NH—$(C_1-C_6)$alkyl, $(C_1-C_6)$alkenyl, O—$(C_1-C_6)$alkenyl, or NH—$(C_1-C_6)$alkenyl, $(C_1-C_6)$alkynyl, O—$(C_1-C_6)$alkynyl, NH—$(C_1-C_6)$alkynyl, S—$(C_1-C_6)$alkyl, S—$(C_1-C_6)$alkenyl, or S—$(C_1-C_6)$alkynyl. In some embodiments, $R^3$ may be $(C_1-C_6)$alkyl, O—$(C_1-C_6)$alkyl, or $(C_1-C_6)$alkenyl. In some embodiments, $R^3$ is methyl, ethoxy, or but-3-en-1-yl, or a pharmaceutically acceptable salt or solvate thereof.

Another aspect of the invention is a compound which has the structure of Formula II, and is known as aplexone.

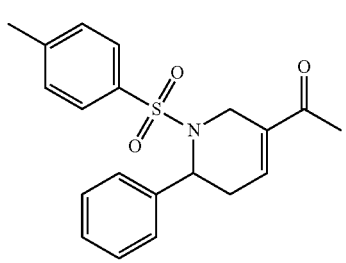

Formula II or a pharmaceutically acceptable salt or solvate thereof.

Another aspect of the invention is a compound of Formula I, which is one of the compounds shown in FIG. 11, or a pharmaceutically acceptable salt or solvate thereof.

Another aspect of the invention is a compound of Formula I, which is represented by Formula III,

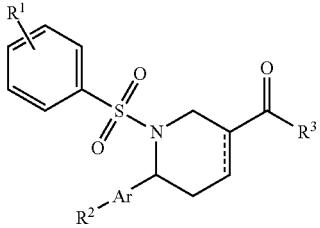

Formula III wherein the dashed bond indicates that a double bond may be present at the indicated location, or the ring may be saturated, $R^1$ may be at any position on the phenyl ring and is hydrogen, halogen, nitro, $(C_1-C_4)$alkyl, $(C_1-C_4)$haloalkyl, O—$(C_1-C_4)$alkyl (alkoxy), S—$(C_1-C_4)$alkyl (alkylthio) or NH—$(C_1-C_4)$alkyl (alkylamino), Ar may be phenyl, pyridine, or thiophene which may bear one or more substituents $R^2$, $R^2$ may be at any available position on the aromatic or heteroaromatic moiety Ar and may be hydrogen, halogen, nitro, $(C_1-C_4)$alkyl, $(C_1-C_4)$haloalkyl, O—$(C_1-C_4)$alkyl (alkoxy), S—$(C_1-C_4)$alkyl (alkylthio) or NH—$(C_1-C_4)$alkyl (alkylamino), except when $R^2$ is in the para-position of a 6-membered ring. In the para-position, $R^2$ may be hydrogen or methyl, and $R^3$ may be $(C_1-C_6)$alkyl, $(C_1-C_6)$haloalkyl, O—$(C_1-C_6)$alkyl, NH—$(C_1-C_6)$alkyl, $(C_1-C_6)$alkenyl, O—$(C_1-C_6)$alkenyl, or NH—$(C_1-C_6)$alkenyl, $(C_1-C_6)$alkynyl, O—$(C_1-C_6)$alkynyl, NH—$(C_1-C_6)$alkynyl, S—$(C_1-C_6)$alkyl, S—$(C_1-C_6)$alkenyl, or S—$(C_1-C_6)$alkynyl, or a pharmaceutically acceptable salt or solvate thereof.

Any of the compounds described above is sometimes referred to herein as a "compound of the invention" and the compounds may be referred to as "aplexone and its functional variants."

Another aspect of the invention is a method for making a compound of the invention, comprising using the relevant synthetic method described herein.

Another aspect of the invention is a pharmaceutical composition comprising a compound of the invention, or a pharmaceutically acceptable salt or solvate, or a functional variant, thereof, and a pharmaceutically acceptable carrier. The pharmaceutical compositions may further comprise additional therapeutic agents appropriate for the intended use of the aplexone, such as agents for treating cancer or lowering cellular cholesterol levels.

Another aspect of the invention is a method for inhibiting angiogenesis in a subject, or for lowing cellular cholesterol levels in a subject, comprising administering to the subject an amount of a compound of the invention or a pharmaceutically acceptable salt or solvate thereof, or a pharmaceutical composition of the invention, which is effective to inhibit angiogenesis or to lower cellular cholesterol levels in the subject, respectively.

In one embodiment, this method is used for treating, inhibiting or delaying the onset or progression of an angiogenesis-mediated condition or disease (such as a cancer or an inflammatory disease) in a subject in need thereof, wherein the amount of the compound or pharmaceutical composition is effective to inhibit angiogenesis associated with the angiogenesis-mediated condition or disease, and angiogenesis associated with the angiogenic disease is inhibited in the subject. The amounts may be effective to reduce one or more symptoms or to inhibit or delay the onset or progression of the condition or disease.

In another embodiment, this method is used for lowering cellular cholesterol levels in a subject in need thereof, wherein the amount of the compound or pharmaceutical composition is effective to lower cellular cholesterol levels in the subject.

In another embodiment, this method is used for reducing the amount of 3-hydroxy-3-methylglutaryl-coenzyme A reductase (HMGCR) in a subject, wherein the amount of the compound or pharmaceutical composition is effective to reduce the amount of HMGCR in the subject.

Another aspect of the invention is a method for treating a subject having an angiogenesis-mediated condition or disease, comprising administering to the subject an amount of a compound or pharmaceutical composition of the invention that is effective to reduce one or more symptoms of the condition or disease.

Another aspect of the invention is a method for treating a subject having cancer, comprising administering to the subject an amount of a compound or pharmaceutical composition the invention that is effective to reduce one or more symptoms of the cancer.

Another aspect of the invention is a method for treating a subject that would benefit from a reduction in cellular cholesterol levels (e.g., having hypercholesterolemia), comprising administering to the subject an amount of a compound or pharmaceutical composition the invention that is effective to lower cellular cholesterol levels in the subject.

In any of the methods of the invention, the subject may be human.

In another aspect of the invention, the method is performed in vitro. For example, it can be a method for inhibiting angiogenesis or reducing cholesterol in an in vitro system, comprising contacting a compound, cell extract, cell or organ in the in vitro system with an effective amount of a compound or a pharmaceutical composition of the invention.

Another aspect of the invention is a method for identifying an agent that preferentially blocks angiogenesis from veins but not arteries, or preferentially blocks angiogenesis from arteries but not veins, comprising contacting a putative agent with a zebrafish and determining the amount of caudal vein morphogenesis and the amount of dorsoventrally positioned intersegmental vessels (ISVs) in the trunk, wherein a statistically significant decrease in the amount of caudal vein morphogenesis compared to the decrease in ISVs indicates that the agent preferentially blocks angiogenesis from veins, and a statistically significant decrease in the amount of ISVs in the trunk compared to the amount of caudal vein morphogenesis indicates that the agent preferentially blocks angiogenesis from arteries.

Another aspect of the invention is a kit comprising a compound or pharmaceutical composition of the invention, wherein the components are packaged in one or more containers.

Another embodiment is a method of making a compound of the invention (e.g., the compound of Formula I, II or III or one of the compounds shown in FIG. 11), using one of the methods described herein.

The present invention relates, e.g., to a molecule of Formula II (aplexone), and to pharmaceutically acceptable salts or solvates, or functional variants thereof. Many such functional variants are encompassed by the molecule of Formula I, and some are shown as Formula III and as the structures in FIG. 11. The most active compounds in the angiogenesis test are Compounds 17-23, 26, and 33 in FIG. 11. The term "aplexone," as used herein, generally refers to aplexone, as well as to such salts, solvates and functional variants. Methods of synthesizing these molecules are conventional. Some such methods are described herein.

By "pharmaceutically acceptable" is meant a material that is not biologically or otherwise undesirable, i.e., the material may be administered to a subject without causing undesirable effects or interactions that are unacceptable for purposes of regulatory approval.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula I, II or III or the compounds shown in FIG. 11. Representative salts include the following organic and inorganic salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention As used herein, the term "solvate" refers to a complex of variable stoichiometry formed by a solute (in this invention, a compound of formula I, II, III or as shown in FIG. 11, or a salt or functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. In one embodiment, the solvent used is water.

Certain of the compounds described herein contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formulas I or II or as shown in FIG. 11, as well as any wholly or partially equilibrated mixtures thereof. The present invention also covers the individual isomers of the compounds represented by the formulas above as mixtures with isomers thereof in which one or more chiral centers are inverted. Also, it is understood that all tautomers and mixtures of tautomers of the compounds of formulas I, II, III and as shown in FIG. 11 are included within the scope of the compounds of formulas I and II and as shown in FIG. 11.

A "functional variant" of aplexone refers to a variant molecule that retains a measurable amount of at least one biological activity of aplexone, such as the ability to inhibit the synthesis of HMGCR, to preferentially inhibit venous angiogenesis, or to lower cholesterol levels in a cell. Described herein are structure-activity relationship (SAR) studies which have permitted the determination of modifications of the aplexone molecule that do or do not alter its biological activity. On the basis of these studies, a generic molecule (Formula I) has been designed, which encompasses a number of suitable function (functionally active) variants (derivatives, analogs) of aplexone. Some such functional variants are shown in FIG. 11. Other functionally active variants are also possible; putative alterations can be readily tested for their activity by a skilled worker, using methods and assays described herein.

The term "aryl" used alone or as part of a larger moiety, refers to mono-, bi-, or tricyclic aromatic hydrocarbon ring systems having five to fourteen members, five to ten members, or five to six members. Examples include phenyl, 1-naphthyl, 2-naphthyl, 1-anthracyl and 2-anthracyl. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl or tetrahydronaphthyl, where the radical or point of attachment is on the aromatic ring. An aryl group may have more than one substituent, up to the total number of free substitution positions. For example, an aryl group may have 1, 2, 3, 4, or 5 substituents. The substituents may the same or different. Substituents on an aryl group include hydrogen, halogen, alkyl, alkenyl, nitro, hydroxyl, amino, alkylamino, alkoxy, and alkylthio, O-acyl, N-acyl, S-acyl as defined herein.

The term "heteroaryl", used alone or as part of a larger moiety, refers to heteroaromatic ring groups having five to fourteen members, five to ten members, or five to six members, in which one or more ring carbons, preferably one to four, are each replaced by a heteroatom such as N, O, or S. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" may be used interchangeably with the term "heteroaryl ring" or the term "heteroaromatic," A heteroaryl group may have more than one substituent, up to the total number of free substitution positions. For example, a heteroaryl group may have 1, 2, 3, 4, or 5 substituents. The substituents may the same or different. Substituents on a heteroaryl group include hydrogen, halogen, alkyl, alkenyl, nitro, hydroxyl, amino, alkylamino, alkoxy, and alkylthio, O-acyl, N-acyl, S-acyl as defined herein.

As used herein, The term "alkyl" used alone or as part of a larger moiety (i.e. "alkoxy," "alkylthio," or "alkylamino" include both straight and branched chains containing one to ten carbon atoms (i.e. 1, 2, 3, 4, 5, 6, 7, 8, 9, or 10 carbon atoms), as well as cyclic structures such as cyclopropyl and cyclobutyl. The term $C_1$-$C_4$ alkyl means an alkyl substituent having 1, 2, 3, or 4 carbon atoms, including linear, branched, or cyclic forms. The term $C_1$-$C_6$ alkyl means an alkyl substituent having 1, 2, 3, 4, 5, or 6 carbon atoms including linear, branched, or cyclic forms. Examples of alkyl groups include methyl (Me), ethyl (Et), propyl (Pr) (including n-propyl ($^n$Pr or n-Pr), isopropyl ($^i$Pr or i-Pr) and cyclopropyl ($^c$Pr or c-Pr)), butyl (Bu) (including n-butyl ($^n$Bu or n-Bu), isobutyl ($^i$Bu or i-Bu), tert-butyl ($^t$Bu or t-Bu) and cyclobutyl ($^c$Bu or c-Bu)), pent (Pe) (including n-pentyl) and so forth. Alkyl groups also include mixed cyclic and linear alkyl groups, such as cyclopentylmethyl, cyclopentylethyl, cyclohexylmethyl, etc., so long as the total number of carbon atoms is not exceeded. The term "alkoxy" refers to an —O-alkyl radical, such as, for example —O-Me, —O-Et, —O-Pr, and so on. The term "alkylthio" refers to an —S-alkyl group, such as, for example, example —S-Me, —S-Et, —S-Pr. The term "alkylamino" refers to mono- (—NRH) or di-substituted (—NR$_2$) amine where at least one R group is an alkyl substituent, as defined above. Examples include methylamino (—NHCH$_3$), dimethylamino (—N(CH$_3$)$_2$). The term "haloalkyl" means alkyl, substituted with one or more halogen atoms, such as trifluoromethyl, chloromethyl, 2,2,2-trifluoroethyl, 1,1,2,2,2,-petanfluoroethyl, and so on.

The term "halogen" or "halo" means F, Cl, Br, or I.

The term "nitro" means (—NO$_2$).

The term "alkenyl" used alone or as part of a larger moiety include both straight and branched chains containing at least one double bond and two to ten carbon atoms (i.e. 2, 3, 4, 5, 6, 7, 8, 9, or 10 carbon atoms), as well as cyclic, non-aromatic alkenyl groups such as cyclopropenyl, cyclobutenyl, cyclopentenyl, cyclopentadienyl, cyclohexenyl, cyclohexadienyl, etc. The term $C_1$-$C_4$ alkenyl means an alkenyl substituent having 1, 2, 3, or 4 carbon atoms, including linear, branched, or cyclic forms. The term $C_1$-$C_6$ alkenyl means an alkenyl substituent having 1, 2, 3, 4, 5, or 6 carbon atoms including linear, branched, or cyclic forms. As used herein, alkenyl groups also include mixed cyclic and linear alkyl groups, such as cyclopentenylmethyl, cyclopentenylethyl, cyclohexenylmethyl, etc., so long as the total number of carbon atoms is not exceeded. The double bond may appear at any point in the alkenyl chain, i.e. it may be an internal double bond, or a terminal double bond. In some instances, the triple bond may be at the terminal end of the alkenyl substituent. When the total number of carbons allows (i.e. more than 4 carbons), an alkenyl group may have multiple double bonds, whether conjugated or non-conjugated, but do not include aromatic structures. Examples of alkenyl groups include ethenyl, propenyl, butenyl, butadienyl, isoprenyl, dimethylallyl, geranyl and so forth.

The term "alkynyl" used alone or as part of a larger moiety include both straight and branched chains containing at least one triple bond and two to ten carbon atoms (i.e. 2, 3, 4, 5, 6, 7, 8, 9, or 10 carbon atoms). The term $C_1$-$C_4$ alkynyl means an alkynyl substituent having 1, 2, 3, or 4 carbon atoms, including linear, branched, or cyclic forms. The term $C_1$-$C_6$ alkynyl means an alkenyl substituent having 1, 2, 3, 4, 5, or 6 carbon atoms including linear, branched, or cyclic forms. The triple bond may appear at any point in the alkynyl substituent, i.e. it may be an internal triple bond, or a terminal triple bond. In some instances, the triple bond may be at the terminal end of the alkynyl substituent. As used herein, alkynyl groups also include mixed branched and linear alkyl groups. When the total number of carbons allows (i.e. more than 4 carbons), an alkenyl group may have multiple triple bonds, whether conjugated or non-conjugated. Examples of alkynyl groups include ethynyl, 1-propynyl, 2-propynyl, 1-butynyl, 2-butynyl, or 3-butynyl, etc.

As used herein, a "substituted" structure refers to a chemical structure where a hydrogen atom has been replaced by a substituent. A "substituent" is a chemical structure that replaces a hydrogen atom on the substituted structure. The term "substituent" does not imply that the substituent is smaller than the substituted structure.

As used herein, the singular forms "a," "an" and "the" include plural referents unless the context clearly dictates otherwise. For example, "a" compound of Formula I includes more than one compound encompassed by the formula.

Traditionally, ISV formation has served as a model for angiogenesis in zebrafish. In this application, the inventors show that the caudal vein plexus in zebrafish forms by endothelial cell sprouting, migration and anastomosis, providing a venous-specific angiogenesis model. Using this model, the inventors screened a collection of small molecules for compounds that preferentially suppress angiogenesis by endothelial cells of either arterial or venous origin, using caudal vein morphogenesis and ISV formation as indicators. In this screen, the inventors identified a compound, aplexone, which can effectively block angiogenesis from the vein, but has limited impact on arterial angiogenesis. The inventors further showed that a number of analogs of aplexone (as shown in FIG. 11) also exhibit this anti-angiogenic activity. The methods to evaluate compounds which exhibit these properties can also be used to test additional small molecules compounds of any type, including other variants of aplexone, or larger molecules, for their ability to stimulate or inhibit venous and/or arterial angiogenesis. Suitable controls for such a method will be evident to a skilled worker.

Without wishing to be bound by any particular hypothesis, the inventors suggest, based on multiple lines of evidence described herein, that aplexone differentially regulates arteriovenous angiogenesis by targeting the HMG-CoA reductase (HMGCR) pathway. Treatment with aplexone effectively inhibits venous EC migration both in zebrafish embryos and cultured human ECs, and it affects the transcription of enzymes in the HMGCR pathway and reduces cellular cholesterol levels. Injecting mevalonate, a metabolic product of HMGCR, reverses the inhibitory effect of aplexone on venous angiogenesis. In addition, aplexone treatment inhibits protein prenylation and blocking the activity of geranylgeranyltransferase induces a venous angiogenesis phenotype resembling that observed in aplexone-treated embryos. Furthermore, endothelial cells of venous origin have higher levels of proteins requiring geranylgeranylation than arterial endothelial cells and inhibiting the activity of Rac or Rho Kinase effectively reduces the migration of venous, but not arterial, endothelial cells. Without wishing to be bound by any particular mechanism, the inventors propose that, taken together, these findings suggest that angiogenesis is differentially regulated by the HMGCR pathway via an arteriovenous-dependent requirement for protein prenylation in zebrafish and human endothelial cells, and that the HMGCR biochemical pathway has an important role in influencing the angiogenic migration.

One aspect of the invention is a method for inhibiting angiogenesis in a subject, or for lowing cellular cholesterol levels in a subject, comprising administering to the subject an amount of a compound of the invention or a pharmaceutically acceptable salt or solvate thereof, or a pharmaceutical composition of the invention, which is effective to inhibit angiogenesis or to lower cellular cholesterol levels in the subject, respectively. This method can be used, e.g., for treating a subject in need thereof; for experimental purposes, such as studying in vivo the mechanisms of cell migration (e.g., germ cell formation, generation of hematopoietic cells from endothelium, angiogenesis) or the mechanism of the regulation of cellular cholesterol levels; or for clinical studies, such as evaluating the effectiveness of a putative therapeutic agent.

Another aspect of the invention is a method for reducing the amount of HMGCR in a subject, comprising administering to the subject an amount of a compound of the invention or a pharmaceutically acceptable salt or solvate thereof, or a pharmaceutical composition of the invention, that is effective to reduce the amount of HMGCR in the subject. Pathways for synthesizing HMGCR are found in a wide variety of organisms, including bacteria, yeast, plants and animals ranging from the simplest (e.g., zebrafish) to higher eukaryotes. A method for inhibiting the HMGCR pathway with aplexone can be carried out in any cell which comprises an HMGCR pathway.

A "subject," as used herein, includes any organism in which the HMGCR pathway can be inhibited, angiogenesis can be inhibited, or cellular cholesterol levels can be reduced by treatment with an aplexone or a functional variant of the invention. Among the suitable subjects are laboratory animals (such as zebrafish, mouse, rat, rabbit, or guinea pig), farm animals, and domestic animals or pets (such as a cat or dog). Mammals, including non-human primates and human patients, are included. Typical subjects that can be treated by a method of the invention include, e.g., animals that have an angiogenesis-mediated disease or condition, such as a cancer, or that are in need of lowering their cholesterol levels. Cells, tissues or organs from such subjects can also be contacted by an aplexone of the invention and studied or used by a method of the invention (e.g., in vitro).

"Angiogenesis," as used here, refers to the development of new blood vessels, generally capillaries, from pre-existing vasculature. Venous angiogenesis originates from veins; arterial angiogenesis originates from arteries. Normal angiogenesis is activated during tissue growth, from embryonic development through maturity, and then enters a period of relative quiescence during adulthood. Normal angiogenesis is also activated during wound healing, and at certain stages of the female reproductive cycle. Inappropriate (aberrant) angiogenesis (e.g., at greater levels than in "normal" subjects) has been associated with a number of conditions or disease states. Such conditions or diseases are referred to herein as "angiogenesis-mediated" conditions or diseases. An "angiogenesis-mediated" condition or disease is a condition or disease which is, at least in part, caused by aberrant or inappropriate angiogenesis, or in which symptoms result from, at least in part, aberrant or inappropriate angiogenesis. Various forms of inflammatory diseases, including chronic inflammatory disorders, can be treated by a method of the invention.

In cancer, the growth of solid tumors has been shown to be angiogenesis-dependent; and the inhibition of angiogenesis has been reported to reduce tumor growth, particularly wherein the cancer is characterized by cancer cells that have not yet been vascularized to form a solid tumor. Among the types of cancer that can be treated by a method of the invention are, e.g., basal cell carcinoma or other solid tumors, medulloblastoma, small cell lung cancer, pancreatic cancer, stomach cancer, esophageal cancer, colorectal cancer, ovarian cancer, multiple myeloma, leukemia, prostate cancer and breast cancer.

Among the conditions or diseases that can be treated by a method of the invention are, e.g., cancer, rheumatoid arthritis, osteoarthritis, asthma, or pulmonary fibrosis), various retinopathies, including diabetic retinopathy, macular degeneration, angiofibroma, neovascular glaucoma, arteriovenous malformation, nonunion fracture, connective tissue disorder, spider veins, Osler-Weber syndrome, atherosclerotic plaque, psoriasis, corneal graft neovascularization, pyogenic granuloma, retrolental fibroplasia, scleroderma, granulations, hemangioma (e.g. in infants), trachoma, hemophilic joints, vascular adhesions, angiofibroma of the nasopharynx, avascular necrosis of bone, endometriosis, metastasis, ischemic disease, atherosclerosis, acute coronary syndromes, stroke, and peripheral vascular diseases (e.g. peripheral ischemia).

Plasma cholesterol levels have been positively correlated with the incidence of clinical events associated with coronary heart disease (CHD). Thus, pharmacological interventions that reduce cholesterol levels in mammals have a beneficial effect on CHD. In particular, decreased plasma levels of cholesterol (e.g., low density lipoprotein (LDL) cholesterol) levels are associated with decreased atherosclerosis and a decreased risk of CHD, and hypolipidemic agents used in either monotherapy or combination therapy are effective at reducing plasma LDL cholesterol levels and the subsequent risk of CHD.

Cholesterol metabolism in mammals involves a series of pathways including cholesterol absorption in the small intestine, cholesterol biosynthesis in numerous tissues (primarily the liver and small intestine), bile acid biosynthesis in the liver and reabsorption in the small intestine, synthesis of cholesterol-containing plasma lipoproteins by the liver and intestine, catabolism of the cholesterol-containing plasma lipoproteins by the liver and extrahepatic tissues and secretion of cholesterol and bile acids by the liver.

Cholesterol synthesis occurs in multiple tissues, but principally in the liver and the intestine. It is a multistep process starting from acetyl-coenzyme A catalyzed by a series of enzymes including HMG-CoA reductase, HMG-CoA synthase, squalene synthetase, squalene epoxidase, squalene cyclase and lanosterol demethylase. Without wishing to be bound by any particular mechanism it is suggested that inhibition of catalysis by these enzymes or blocking HMG-CoA reductase gene expression may be an effective means to reduce cholesterol biosynthesis, and can lead to a reduction in cholesterol levels. For example, there are known HMG-CoA reductase inhibitors (e.g., lovastatin, simvastatin, pravastatin, fluvastatin, atorvastatin, rivastatin, cerivastatin, nisvastatin) that are used for the treatment of hypercholesterolemia.

The inventors show herein that aplexone and functional variants thereof are effective for reducing cellular cholesterol levels and thus are useful for treating subjects having undesirably high cellular levels of cholesterol (hypercholesteremia).

An "effective amount," as used herein, refers to an amount that can bring about at least a detectable effect. A "therapeutically effective amount," as used herein, refers to an amount that can bring about at least a detectable therapeutic response in a subject being treated (e.g. the amelioration of a symptom), over a reasonable time frame. For example, a "therapeutic effect" can refer to a measurable amount of a reduction in cholesterol levels or of an inhibition of angiogenesis. A therapeutic effect for cancer treatment may refer, e.g., to one or more of the following: 1) reduction in the number of cancer cells; 2) reduction in tumor size; 3) inhibition (e.g., slowing to some extent, preferably stopping) of cancer cell infiltration into peripheral organs; 4) inhibition, to some extent, of tumor growth; 5) reduction on the number and/or biological activity of cancer stem cells; and/or 6) relieving to some extent one or more of the symptoms associated with an angiogenesis-mediated disorder other than cancer that is being treated, such as, e.g., inhibition or regression of atherosclerotic lesions, inhibition of Alzheimer's disease, or inhibition of an inflammatory response, e.g. in arthritis.

In embodiments of the invention, the amount of, e.g., reduction of serum cholesterol level or of angiogenesis can vary depending upon the particular assay or condition being measured, the amount of the aplexone administered, etc, and can be routinely determined using conventional methods. Angiogenesis can be quantified, e.g., by cell migration (e.g., wound closure) or by sprouting by in vivo imaging (both as described herein), in vitro by using cultured endothelial cells in matrigel, etc. The effect of aplexone on cancer can be measured, e.g., by assaying cancer cell survival, growth, or migration in vitro using cultured cancer cell lines in or in vivo by testing survival or tumor size in an animal model, such as a mouse model. For example, the inhibited value can be about 1%, 5%, 10%, 20%, 30%, 40%, 50% or more of that in the untreated sample. Intermediate values in these ranges are also included.

The agents discussed herein can be formulated into various compositions, e.g., pharmaceutical compositions, for use in therapeutic treatment methods. The pharmaceutical compositions can be assembled as a kit. Generally, a pharmaceutical composition of the invention comprises a therapeutically effective amount of a composition of the invention.

A pharmaceutical composition of the invention can comprise a carrier, such as a pharmaceutically acceptable carrier. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

A pharmaceutical composition or kit of the invention can contain other pharmaceuticals, in addition to an aplexone or a functional variant thereof. Suitable additional pharmaceuticals or other treatments will be evident to a skilled worker.

For example, for the treatment of cancer, aplexone can be combined or co-administered with any of a variety of anti-cancer (chemotherapeutic) agents, which will be evident to a skilled worker. These include, e.g., EGFR inhibitors, kinase inhibitors, Taxol related agents, etc.

For the treatment of a disease or condition characterized by high blood levels of cholesterol, aplexone can be combined or co-administered with a variety of suitable cholesterol-lowering agents, including, e.g., a variety of statins, such as, e.g., atorvastatin, marketed as Lipitor or Torvast (manufactured by Pfizer), fluvastatin (Lescol), lovastatin (Mevacor, Altocor, Altoprev), pitavastatin (Livalo, Pitava), pravastatin (Pravachol, Selektine, Lipostat), roosuvastatin (Crestor), simvastatin (Zocor, Lipex), or combinations of a statin or another agent, as ezetimibe/simvastatin.

The other agent(s) can be administered at any suitable time during the treatment of the subject, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

An aplexone of the invention, alone or in combination with other therapeutic agents, can be made into any of a variety of formulations, for any of a variety of routes of administration.

Suitable routes of administration of aplexone include, e.g., oral, intravenous, topical, intravesicular, intraperitoneal, intramuscular, intradermal, subcutaneous and intraarterial.

In embodiments of the invention, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

Formulations suitable for oral administration can consist of liquid solutions, such as an effective amount of the agent dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract.

Formulations suitable for parenteral administration (e.g. intravenous) include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Formulations suitable for administration via inhalation (aerosols) can be made and placed into pressurized acceptable propellants, such as dichlorodifluoromethane, propane, nitrogen and the like.

An aplexone of the invention, alone or in combination with other therapeutic agents, can be made into suitable formulations for transdermal application and absorption (Wallace et al., 1993, supra). Transdermal electroporation or iontophoresis also can be used to promote and/or control the systemic delivery of the agents and/or pharmaceutical compositions of the present invention through the skin (e.g., see Theiss et al. (1991), *Meth. Find. Exp. Clin. Pharmacol,* 13, 353-359).

Formulations which are suitable for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, or the like.

One skilled in the art will appreciate that a suitable or appropriate formulation can be selected, adapted or developed based upon the particular application at hand.

Dosages for an aplexone or functional variant thereof can be in unit dosage form, such as a tablet or capsule. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient. One skilled in the art also can readily determine and use an appropriate indicator of the "effective concentration" of the compounds of the present invention by a direct or indirect analysis of appropriate patient samples (e.g., blood and/or tissues).

The dose of an aplexone or functional variant thereof of the invention, or a pharmaceutical composition thereof, administered to an animal, particularly a human, in the context of the present invention should be sufficient to elicit at least a therapeutic response in the individual over a reasonable time frame. The dose used to achieve a desired concentration in vivo will be determined by the potency of the particular aplexone employed, the pharmacodynamics associated with the agent in the host, the severity of the disease state of infected individuals, as well as, in the case of systemic administration, the body weight and age of the individual. The size of the dose also will be determined by the existence of any adverse side effects that may accompany the particular agent, or composition thereof, employed. It is generally desirable, whenever possible, to keep adverse side effects to a minimum.

For example, a dose can be administered at dosage levels in the range of from about 10 mg to about 600 mg per day (e.g., about 10, 20, 30, 40, 50, 60, 70, 80, 90, 100, 150, 200, 250, 300, 350, 400, 450, 500, 550, 600 mg per day). Intermediate values are also included. For a normal human adult of approximately 70 kg or body weight, this translates to a dosage of from about 0.125 mg/kg to about 8.0 mg/kg of body weight per day.

A therapeutically effective dose of an aplexone or other agent useful in this invention is one which has a positive clinical effect on a patient, e.g. as measured by the ability of the agent to reduce angiogenesis or cellular cholesterol levels. The therapeutically effective dose of each agent can be modulated to achieve the desired clinical effect, while minimizing negative side effects. The dosage of the agent may be selected for an individual patient depending upon the route of administration, severity of the disease, age and weight of the patient, other medications the patient is taking and other factors normally considered by an attending physician, when determining an individual regimen and dose level appropriate for a particular patient.

When given in combined therapy, the other agent can be given at the same time as the aplexone, or the dosing can be staggered as desired. The two (or more) drugs also can be combined in a composition. Doses of each can be less when used in combination than when either is used alone. Those skilled in the art would be able to determine the accepted dosages for each of the therapies using standard therapeutic dosage parameters.

The invention may include a method of systemic delivery or localized treatment alone or in combination with administration of other agent(s) to the patient.

In another aspect of the invention, a method for reducing the amount of HMGCR, inhibiting angiogenesis, or reducing cellular cholesterol levels by administering an aplexone of the invention is carried out in vitro (in an in vitro system). An in vitro system can comprise, e.g., isolated chemical constituents, cell-free extracts, cell, tissue or organ culture, etc. The method can comprise administering to the in vitro system (e.g., to a cell, tissue or extract thereof in the system) an effective amount of a compound or composition of the invention to exert a measurable effect. In embodiments of the invention, in which angiogenesis is inhibited, the angiogenesis is primarily venous, rather than arterial, angiogenesis.

Both in vitro and in vivo embodiments of the invention can be used for a variety of experimental purposes. Experimental studies can be carried out in vitro (cell, tissue or organ culture) or in vivo (e.g., in zebrafish or in mammals) to study the mechanisms responsible for aplexone function and/or to elucidate biochemical and physiological pathways which aplexone can disrupt, such as, e.g., cell migration (such as germ cell formation or generation of hematopoietic cells from endothelium), cholesterol metabolism and angiogenesis. Aplexone can also be used as a starting material for identifying additional functional variants that exhibit desirable properties; and can be studied by such methods. In addition, in vitro and in vivo methods of the invention can be used for characterizing and evaluating the effectiveness of putative or known therapeutic agents, including in clinical studies. Furthermore, aplexone can be used to stimulate growing organs, e.g. from stem cells.

Another embodiment of the invention is a kit useful for any of the methods disclosed herein, either in vitro or in vivo. Such a kit can comprise one or more of the aplexones or functional variants discussed herein. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form. A skilled worker will recognize components of kits suitable for carrying out any of the methods of the invention.

When a "statistically significant amount" is referred to herein, this depends on a number of factors, such as the technique of the experimenter. The clinical trial conditions, the quality of the equipment used, etc. For example, in certain cases, a statistically significant amount may be a change of 1%. In other cases, a statistically significant amount can be represented by a change of at least about 5%, 10%, 20%, 50%, 75%, double, or more. In relation to inhibition, the significant reduction may be to a level of less than about 90%, 75%, 50%, 25%, 10%, 5%, 1%, or less.

In the foregoing and in the following examples, all temperatures are set forth in uncorrected degrees Celsius; and unless otherwise indicated, all parts and percentages are by weight.

EXAMPLES

Example 1

Methods for the Experiments Described in Example 2

Zebrafish Husbandry

The Tg(kdrl:GFP)$^{la116}$ and Tg(myl7:GFP) transgenic line and smo$^{hi1640}$ were used for this study (Chen et al., 2001; Huang et al., 2003; Choi et al., 2007). Adult fish and embryos were maintained as previously described (Westerfield, 2000).

Imaging

Images of GFP expression in Tg(kdrl:GFP) embryos were acquired using a Zeiss SV-11 epifluorescence microscope. Confocal images were acquired using a Carl Zeiss Laser Scanning Systems LSM510 equipped with 20× air, 20× water or 40× water immersion objectives. For single time point confocal images, embryos were anesthetized with 0.01% tricaine and embedded in 1% agarose. When capturing time-lapse confocal movies, embryos were mounted in 3.5% methylcellulose (Sigma-Aldrich) and imaged for 5 hrs on a heated stage at 28.5° C. The images obtained were analyzed using the Zeiss LSM Image Brower version 4 and Image J.

Chemical Screen and Aplexone Treatment

A synthetic chemical library containing 168 compounds (Castellano et al., 2007) and 300 chemicals from Biomol International LP, consisting of 72 ion channel inhibitors (Cat No. 2805), 84 kinase/phosphatase inhibitors (Cat No. 2831), 84 orphan ligands (Cat No. 2825), and 60 endocannabinoids (Cat No. 2801) were screened. The synthetic small molecules were prepared through nucleophilic phosphine catalysis of allenoates (Zhu et al., 2003). Four Tg(kdrl:GFP) embryos were placed into each well of 96-well plates containing a 10 µM solution of each chemical compound dissolved in embryo buffer with 0.1% DMSO. The embryos were raised at 28.5° C. and examined for defects in blood vessel development at 1 and 2 days after treatment. Standard parameters such as numbers of somites and head to body angle were used to determine the stages of zebrafish embryos (Kimmel et al., 1995).

Aplexone treatment described in this study was carried out at a concentration of 10 µM starting at 10 hpf unless otherwise specified.

Microarray and Quantitative RT-PCR

Embryos at the 5-somite stage were treated with 0.4% DMSO (control) or 10 µM of aplexone in 0.4% DMSO and total RNA was isolated using the RNAeasy micro kit (Qiagen) at 30 hpf. Microarray analysis was performed in triplicate using the Affymetrix Zebrafish GeneChip, representing 15,617 genes. Synthesis and labeling of antisense RNA was performed as recommended by the array manufacturer using kits from Invitrogen for double-stranded cDNA synthesis, Enzo Life Sciences for transcription and labeling of antisense RNA and Affymetrix for probe purification and hybridization controls. Microarray hybridization data were analyzed using scripts written in the statistical programming language R (Team, 2009). Differentially expressed genes (DEGs) were identified using a linear model and multiple testing correction from the limma package (Smyth, 2004). The expression values were obtained using the robust multi array algorithm (Irizarry et al., 2003).

Quantitative RT-PCR was performed as follows. First strand cDNA was synthesized using the SuperScript™ first-strand synthesis system for RT-PCR (Invitrogen) and relative expression levels of genes were determined using iQ SYBR Green Supermix and an iCycler (Bio-Rad Laboratories). GAPDH was used for normalization. Sequences of primers used in this study are provided in Table 2.

TABLE 2

Primers used in quantitative PCR and generating chimeric proteins.

| gene | | primer sequences |
|---|---|---|
| hmgcs1 | forward | 5'-TGAAGAGTCGGGCAACACTGATGT-3' |
| hmgcs1 | reverse | 5'-GCAATATCACCAGCAACAACCAGAGC-3' |

TABLE 2 -continued

Primers used in quantitative PCR and generating chimeric proteins.

| gene | | primer sequences |
|---|---|---|
| hmgcr | forward | 5'-GCTTTGGCCAAGTTTGCTCTGAGT-3' |
| hmgcr | reverse | 5'-TCCACGAGGGCATCAAGAGTGAAA-3' |
| fdps | forward | 5'-GATCCTGTTCTCAGTGATGCCCTCAA-3' |
| fdps | reverse | 5'-ACTTCCTCAGTTGGCAGCTCAGAT-3' |
| cyp51 | forward | 5'-TTCAGACGGAGAGATCGAGCACAT-3' |
| cyp51 | reverse | 5'-TCTCGGTATCTTCTCTGCGCTTCTTG-3' |
| sc4mol | forward | 5'-GGAAGTGCTTCAAGATGCTGCTGT-3' |
| sc4mol | reverse | 5'-GTGTCCCAGTCATAAGGGATGCTGAA-3' |
| dhcr7 | forward | 5'-TAAGCAGCAGGAGCTGTATGGTTACG-3' |
| dhcr7 | reverse | 5'-GTCTTCAGGTACCAGGCTTCATTCCA-3' |
| insig1 | forward | 5'-AGAGGAAGTGCTGGACACGCTATT-3' |
| insig1 | reverse | 5'-CGCTTGAACTTGTGTGGTTCTCCAAG-3' |
| gapdh | forward | 5'-TGTGATGGGAGTCAACCAGGACAA-3' |
| gapdh | reverse | 5'-TTAGCCAGAGGAGCCAAGCAGTTA-3' |
| cherry-RhoA | forward | 5'-GGATCCACCATGGTGAGCAAGGGCGAG-3' |
| cherry-RhoA | reverse | 5'-GAATTCTCACAAGACAAGGCACCCAGATT TTTTCTTCCCACGTCTAGCTTGCAGAGCAGCT CTCGTCTTGTACAGCTCGTCCATGCC-3' |
| cherry-Ras | forward | 5'-ACGTCGGATCCACCATGGTGAGCAAGG-3' |
| cherry-Ras | reverse | 5'-ACGTCGAATTCAGGAGAGCACACACTTGC-3' |

The SEQ ID NOs of the primers shown in this Table are, from top to bottom: SEQ ID NO:1-SEQ ID NO:20.

Cholesterol Assay

The yolk was removed from embryos by vortexing in calcium-free Ringer's solution with 1 mM EDTA at 4° C. The embryos were then pelleted and washed with fresh calcium free Ringer's solution 5 times before being resuspended in cholesterol assay reaction buffer and were then lysed by sonication using a Sonifier 450 (Branson). Cholesterol levels in the embryo lysate were measured with an Amplex Red Cholesterol Assay Kit (Invitrogen) and Flex station II (Bucher Biotec). The total protein concentration of the embryo lysate was measured using a DC protein assay (Bio-Rad Laboratories) and SpectraMax plus (Molecular Devices).

Localization of Chimeric Proteins mCherry-RhoCLVL was generated by PCR amplification of mCherry from pmCherry-N3 (a generous gift from S. Walsh) using primers containing sequences coding for the C-terminal 20 amino acid residues of human RhoA. mCherry-RasCVLS was amplified from pME-mCherry-CAAX (a generous gift from C.-B. Chien). The PCR products were sub-cloned into pcGlobin2 (Ro et al., 2004) and mRNA was synthesized using the mMESSAGE mMACHINE kit (Ambion). Zebrafish embryos were injected with 250 pg of mCherry-RhoCLVL and mCherry-RasCVLS mRNA at 1-cell stage, and raised with or without the presence of 10 µM aplexone at 25° C. and fixed at 80% epiboly. Cellular localizations of the mCherry chimeras were analyzed with confocal microscopy.

Cell Culture and Wound Healing Assays

HUVECs and HUAECs were purchased from VEC Technologies. Cells were cultured on 0.1% Gelatin-coated dishes in Medium 199 (Mediatech), supplemented with 15% Fetal Bovine Serum (ATCC), 48 µg/mL Endothelial Cell Growth Supplement (BD Biosciences), 64 µg/mL Heparin Sulfate (Sigma-Aldrich), 0.9 mM Sodium Pyruvate (Mediatech), 100 IU/ml Penicillin (Mediatech), and 100 µg/ml Streptomycin (Mediatech).

For the wound healing assay, cells were cultured in 24-well plates to confluence before being subjected to a 2-hour pre-treatment with either DMSO, aplexone, Rockout (Calbiochem) or NSC 23766 (TOCRIS Bioscience). After the pre-treatment, the monolayer of endothelial cells was scratched and the closure of the wound was measured after 8 hr. The images of wounds were taken at 0 and 8 hr after scratching and the area of the wound was measured using Image J. The migration distance (the width of the wound) was calculated by dividing the area by the length of the wound. Cells below passage seven were used in this study.

Western Blotting

Total proteins were prepared by lysis of endothelial cells with sample buffer (62.5 mM, Tris-HCl pH6.8, 20% Glycerol, 2% SDS, 5% β-mercaptoethanol, 0.025% Bromophenol blue) and boiling for 5 min. The antibodies for RhoA (Santa Cruz Biotechnology, Inc.) and Rac1 (Millipore) were purchased and the Western blots were performed according to the manufacturer's protocols.

Microinjection 8 ng tnnt2 MO (Gene Tools) (Sehnert et al., 2002), 3 nl of 4 mM GGTI-2133 (Calbiochem), 3 nl of 5 mM L744,832 (Calbiochem) and 1 nl of 2M mevalonate (Sigma-Aldrich) were injected into 1-2 cell stage embryos.

Example 2

Figure 9:
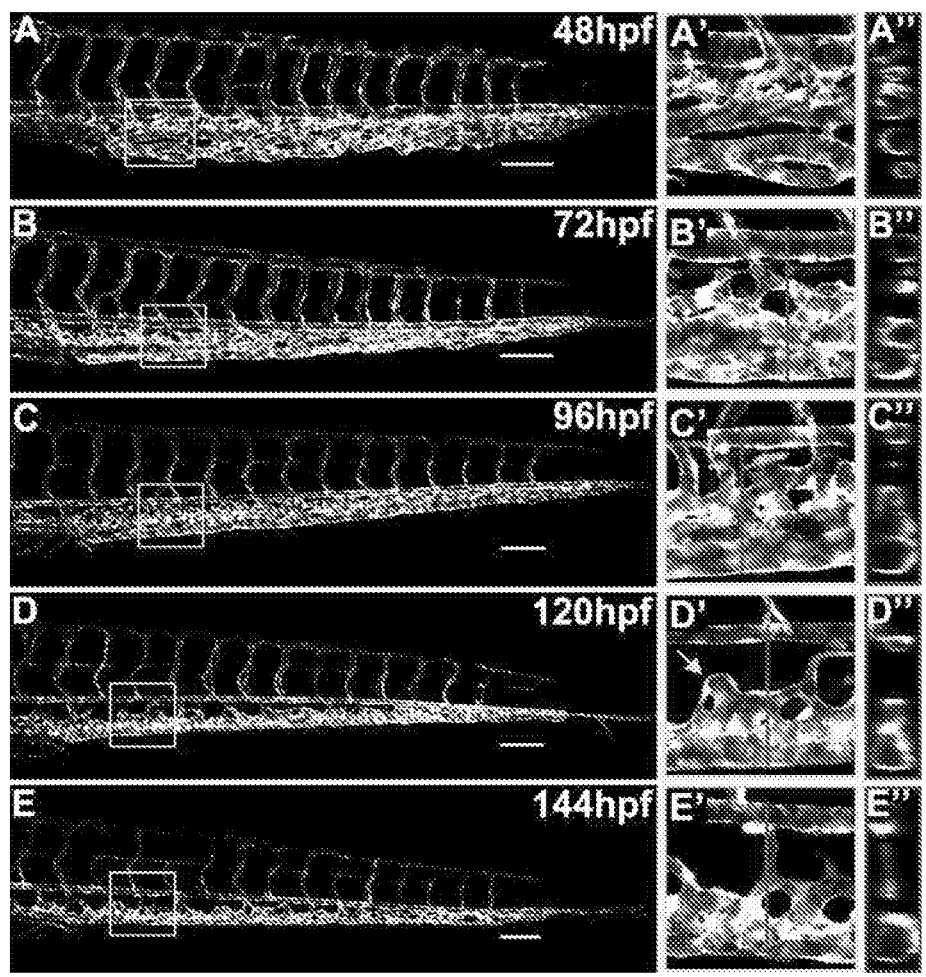
FIG. 9 shows remodeling of the caudal vein plexus. A-E, Confocal images of caudal vasculature from 2 dpf to 6 dpf. A'-E', Higher magnification images of the boxed regions shown in A-E. A"-E", Optical cross sections of blood vessels indicated by red bars in A'-E'.

Aplexone Targets the HMG-CoA Reductase Pathway and Differentially Regulates Arteriovenous Angiogenesis a. Zebrafish Caudal Vein Morphogenesis At 25 hpf, coinciding with the initiation of blood circulation, the caudal aorta and caudal vein are positioned very closely to each other. Using time-lapse confocal imaging of Tg(kdrl:GFP) embryos, we identified a two-stage process involving angiogenesis and vascular remodeling that relocates the caudal vein from its initial position of less than 5 µm ventral to the DA at 27 hpf to a position of 50 µm ventral to the DA after 5 days of development (FIG. 1B,E). Stage I of caudal vein morphogenesis begins at 25 hpf when active angiogenesis is observed in the caudal region. Angiogenic sprouts originating from the caudal aorta migrate dorsally along the boundaries of somites and become ISVs, whereas ECs of the caudal vein send out filopodia at various sites and then migrate ventrally and fuse with neighboring sprouts (FIG. 1A-C). Active sprouting, migration and anastomosis occur in the caudal vein region between 25 hpf and 30 hpf to form the primordial caudal vein plexus (CVP). Soon after that, sprouting angiogenesis in this region slows down, but the primordial CVP continues to mature and becomes lumenized and serves as a conduit for blood circulation by 36 hpf. Stage II of caudal vein morphogenesis begins at around 48 hpf when active ventral sprouting of ECs of the caudal vein has ceased. During the next few days of development, many endothelial cells of the venous origin in the tail regress restricting flow to the most ventrally positioned vascular channel (FIG. 1E and FIG. 9). Taken together, the morphogenesis of the caudal vein involves sprouting, migration, anastomosis, pruning and regression of ECs originating exclusively from the vein and therefore can serve as an excellent model for venous angiogenesis (Stage I) and remodeling (Stage II) in zebrafish.

B. Zebrafish Chemical Screen Identifies Aplexone as an Inhibitor of Venous Angiogenesis To understand whether angiogenesis from arterial and venous ECs are under different genetic controls we screened a collection of small molecules for compounds that preferentially suppress angiogenesis from exclusively one cell type. In this screen, we used the primary ISV sprouts as the readout for arterial-derived angiogenesis, and the CVP and secondary ISV sprouts as indicators of venous-derived angiogenesis. We found one synthetic compound, aplexone, which has a lineage-dependent effect on angiogenesis. The spatial and temporal development of primary ISVs in the trunk is indistinguishable between 2-day-old control and aplexone-treated embryos (FIG. 1L-M'). The formation of the CVP, however, is severely defective in aplexone-treated embryos, resulting in a single-lumen caudal vein (FIG. 1F-I, K). Secondary ISVs are also absent in these embryos (FIG. 1L-M'). In situ hybridization analyses using arterial (ephrin B2a) and venous (flt4 and ephB4) markers could not distinguish aplexone-treated embryos from control embryos (FIG. 2), suggesting that treatment with aplexone suppresses venous angiogenesis without affecting arteriovenous differentiation.

We further studied the impact of aplexone on caudal vein angiogenesis at the cellular level. During angiogenesis, ECs send out filopodia followed by the migration of the cell body to form sprouts. In control embryos, multiple angiogenic sprouts are generated from the caudal vein by 27 hpf (FIG. 1B). Interestingly, while the caudal vein ECs of aplexone-treated embryos formed filopodia, they never matured into angiogenic sprouts (FIG. 1G,H), suggesting a defect in EC migration. We then traced the migration distance of ECs during CVP formation. In vivo time-lapse confocal imaging showed that ECs migrated an average distance of 70 µm between 25 hpf and 30 hpf in control embryos, but only 35 µm in aplexone-treated embryos (FIG. 3A-C), demonstrating a strong inhibitory effect of aplexone on venous EC migration.

Figure 3:
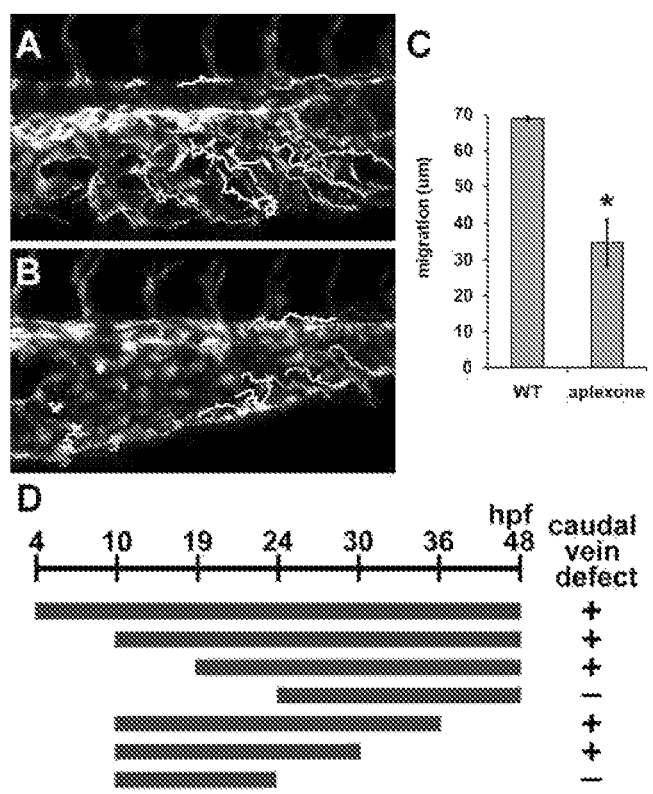
FIG. 3 shows that aplexone affects the migration of caudal vein endothelial cells. A-B, Representative images of the caudal vein of control (A) and 10 µM aplexone-treated embryos (B) at 30 hpf. Images were overlaid with the endothelial cell migration path inferred from time-lapse confocal movies taken from 25 hpf to 30 hpf. The migration of caudal vein endothelial cells was traced using the Manual Tracking feature of ImageJ and the positions of ISV sprouting points were used as references to adjust for the growth of embryos. C, The distance of endothelial cell migration in caudal vein of control and aplexone-treated Tg(kdrl:GFP) embryos. Asterisk indicates p<0.05. (D) The window of application of aplexone. Grey bars represent the developmental stages during which Tg(kdrl:GFP) embryos were exposed to 10 µM aplexone and the caudal vein phenotype was analyzed at 48 hpf. A "+" indicates that caudal vein angiogenesis was inhibited. A "−" indicates the formation of normal caudal vein plexus.

We next examined the critical time window of application in which aplexone treatment effectively blocks CVP formation. In the first set of experiments, we began the treatment of aplexone at various time points and analyzed CVP formation at 48 hpf. In a second set of experiments, the treatment of aplexone began at 10 hpf and the compound was washed off at various developmental stages. As shown in FIG. 3D, only those embryos exposed to aplexone between 19 and 30 hpf, the time when caudal vein ECs undergo active sprouting, developed a single lumenized caudal vein, demonstrating that aplexone should be present during the active angiogenic phase of caudal vein morphogenesis to block CVP formation.

Figure 4:
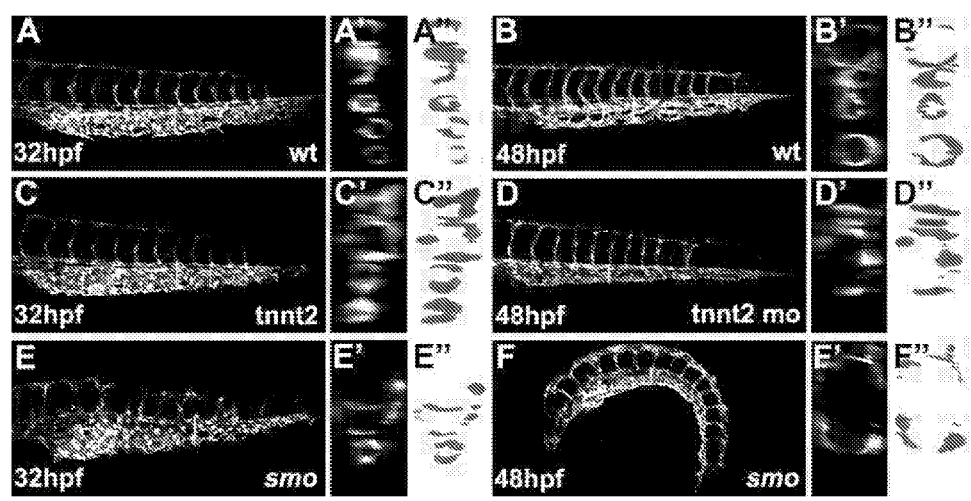
FIG. 4 shows that blood circulation is not required for sprouting angiogenesis from the caudal vein. A-B, Caudal vein plexus in wild type Tg(kdrl:GFP) embryos observed at 32 hpf (A) and 48 hpf (B). C-F, At 32 hpf, the primordial caudal vein plexus was properly formed in tnnt2 morphant (C) and smo mutant (E) embryos, but the plexus structure was not maintained and degenerated into a single-lumen structure at 48 hpf (D, F). A'-F', Optical cross sections of blood vessels indicated by yellow lines in A-F. A"-F", schematic drawings of images shown in A'-F'. Grey and black represent the artery and vein, respectively.

Hemodynamic flow has a significant impact on vascular remodeling (Lucitti et al., 2007). Aplexone-treated embryos lack blood circulation, raising the question of whether the effects of aplexone on venous angiogenesis are secondary to the hemodynamic defect. To assess the impact of blood circulation on CVP formation, we utilized embryos deficient in tnnt2 or smoothened (smo), two zebrafish models without circulation (Chen et al., 2001; Sehnert et al., 2002). We found that the formation of angiogenic sprouts is normal and an elaborate primordial CVP is noted in both models by 32 hpf (FIG. 4C,E), indicating that circulation is not required for caudal vein angiogenesis and excluding the notion that the inhibitory effect of aplexone on venous angiogenesis is secondary to a defect in circulation. Interestingly, a single lumen structure is observed in tnnt2 morphants and smo mutant embryos at 48 hpf (FIG. 4D,F), suggesting that the maintenance of the plexus structure of the caudal vein requires proper circulation.

C. Aplexone Modulates the HMG-CoA Reductase Pathway

To elucidate the molecular mechanism of action of aplexone, we compared expression profiles of aplexone-treated embryos to DMSO-treated control embryos. Fourteen genes represented on the Affymetrix Zebrafish Genome Array are up-regulated by 2-fold or greater in aplexone-treated embryos, including insig-1 and four genes involved in the HMG-CoA reductase (HMGCR) pathway (Table 1). Quantitative RT-PCR confirmed this finding and further revealed that additional enzymes in the HMGCR pathway that were not represented on the microarray were also up-regulated in aplexone-treated embryos (Table 1). Cholesterol is a metabolic product of the HMGCR pathway that negatively regulates the transcription of insig-1 and enzymes in the HMGCR pathway (Horton et al., 2002). We found that aplexone reduced embryonic cholesterol levels to a comparable degree as treatment with atorvastatin, a potent inhibitor of HMGCR (FIG. 5B) (Ii and Losordo, 2007). On the contrary, embryos treated with compound AP13, a non-functional aplexone analog, have normal cholesterol levels (FIG. 5B) and normal venous angiogenesis (data not shown), suggesting that, as with atorvastatin, aplexone blocks the HMGCR biochemical pathway.

TABLE 1

Enzymes involved in the HMGCR pathway are up-regulated in aplexone treated embryos. The genes that up- or down-regulated more than 2 fold in aplexone-treated embryos are listed. Fold changes of the gene in aplexone-treated embryos detected by microarray and quantitative RT-PCR are indicated on the right.

| Gene | microarray | qPCR |
| --- | --- | --- |
| glutathione S-transferase | 3.2 | |
| selenoprotein W | 3.1 | |
| sulfotransferase | 3.0 | |
| cytochrome P450, family 51 (CYP51) | 2.8 | 4.4 |
| insulin induced gene 1 (INSIG) | 2.6 | 5.1 |
| fatty acid desaturase 2 | 2.4 | |
| glutathione reductase like | 2.2 | |
| glutamate dehydrogenase 1a | 2.2 | |
| Krueppel-like factor 11 (TIEG-2) | 2.1 | |
| carbonyl reductase 1-like | 2.1 | |
| insulin-like growth factor binding protein 1 | 2.1 | |
| 3-hydroxy-3-methylglutaryl-Coenzyme A synthase 1 (HMGCS) | 2.0 | 2.8 |
| farnesyl diphosphate synthetase (FDPS) | 2.0 | 2.2 |
| sterol-C4-methyl oxidase-like (SC4MOL) | 2.0 | 5.6 |
| 3-hydroxy-3-methylglutaryl-Coenzyme A reductase (HMGCR) | | 6.7 |
| 7-dehydrocholesterol reductase (DHCR7) | | 2.5 |
| coronin, actin binding protein, 1A | −2.1 | |
| myosin regulatory light chain interacting protein | −2.1 | |
| nephrosin | −2.4 | |
| lymphocyte cytosolic plastin 1 | −2.7 | |
| lysozyme | −2.7 | |

Figure 5:
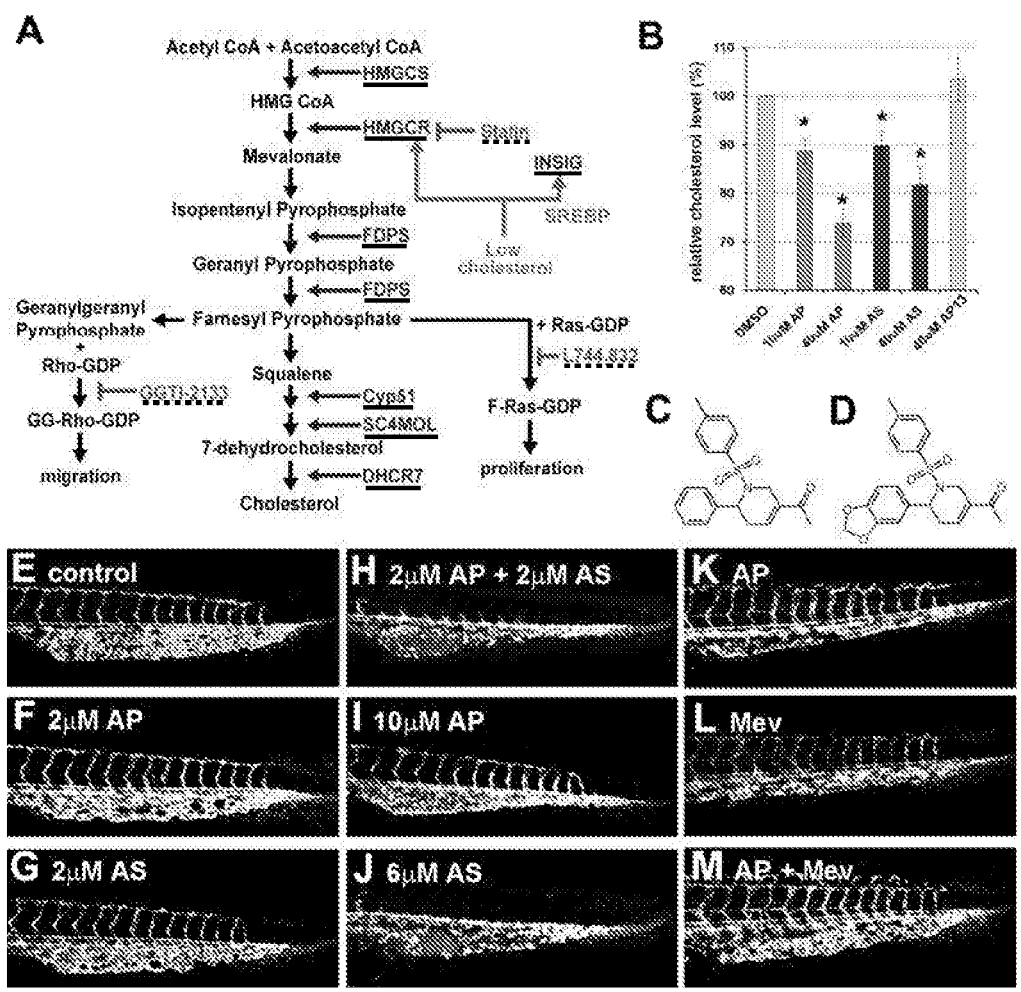
FIG. 5 shows that aplexone affects the HMGCR pathway. A, Simplified schematic diagram of the HMGCR pathway. Enzymes involved in the pathway are indicated by solid underlining. Feedback loop is indicated in grey. Chemical inhibitors of the pathway are indicated by dotted underlining. HMGCS, 3-hydroxy-3-methylglutaryl-CoA synthase; HMGCR, HMG CoA reductase; FDPS, farnesyl diphosphate synthetase; Cyp51, lanosterol 14α-demethylase; SC4MOL, sterol-C4-methyl oxidase-like; DHCR7,7-dehydrocholesterol reductase; INSIG, insulin induced gene 1; SREBP, sterol regulatory element binding proteins. B, Relative cholesterol levels in embryos treated with 0.4% DMSO as a control (DMSO), aplexone (AP (aplexone), structure shown in C), atorvastatin (AS) or a non-functional aplexone analog (AP13, structure shown in D). Both aplexone and atorvastatin reduce cholesterol level significantly (*, p<0.05). E-J, Aplexone and atorvastatin have a synergistic effect on caudal vein angiogenesis. Embryos were treated with the chemicals indicated beginning at 10 hpf and caudal vein images were taken at 48 hpf. K-M, Mevalonate reverses the effect of aplexone on caudal vein plexus formation. Caudal vein plexus of embryos treated with 5 µM aplexone beginning at 2 hpf (K), injected with 1 nl of 2M mevalonate (I) or injected with mevalonate followed by aplexone treatment (M).

If aplexone blocks venous angiogenesis via influencing the activity of the HMGCR pathway, one would expect that blocking the same pathway with atorvastatin should impede CVP formation. Indeed, atorvastatin-treated embryos exhibited phenotypes similar to those observed in embryos exposed to aplexone (FIG. 5J). In addition, while embryos treated with suboptimal levels of aplexone (2 µM) or atorvastatin (2 µM) develop a normal CVP, embryos co-treated with suboptimal levels of aplexone and atorvastatin exhibit a single-lumen CVP (FIG. 5F-H), indicating a synergistic effect of atorvastatin and aplexone on venous angiogenesis. Furthermore, injecting mevalonate, a downstream metabolic product of HMGCR, into zebrafish embryos blocks the inhibitory effects of aplexone (FIG. 5M). Together, these findings indicate that aplexone influences venous angiogenesis by modulating the activity of early steps in the HMGCR pathway. In light of the rescue effect of mevalonate, we also surmise, without wishing to be bound by any particular mechanism, that it is likely that aplexone acts upstream of mevalonate.

D. Venous Angiogenesis Requires Protein Prenylation

Figure 6:
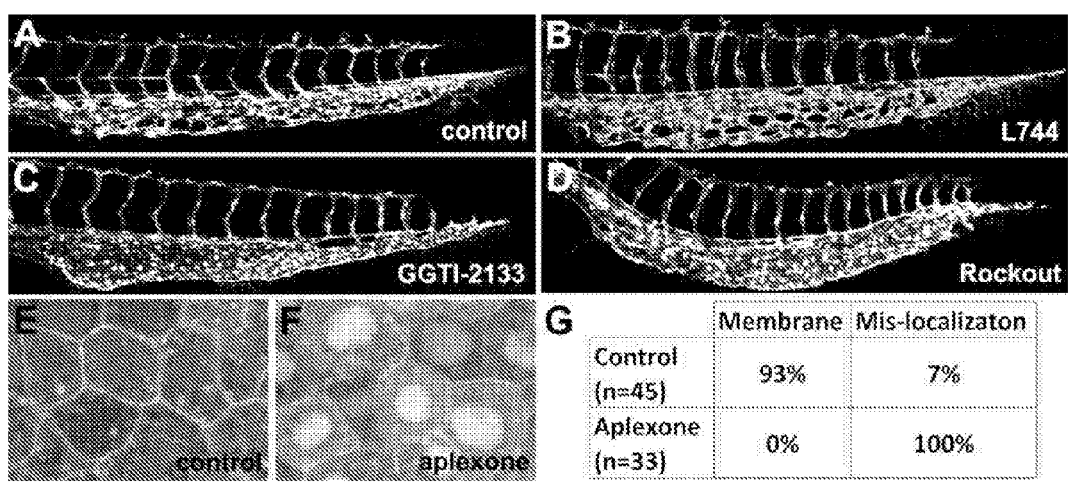
FIG. 6 shows that aplexone inhibits caudal vein angiogenesis by blocking geranylgeranylation. A, Caudal vein of control Tg(kdrl:GFP) embryo at 48 hpf. B-D, Caudal vein of L744,832-injected (B), GGTI-2133-injected (C) or 50 µM Rockout-treated (D) Tg(kdrl:GFP) embryos analyzed at 48 hpf. E-F, Representative confocal images of the localization of mCherry-rhoCAAX fusion proteins in control (E) and aplexone-treated (F) embryos at 80% epiboly. mCherry-rhoCAAX fusion proteins are predominantly localized to the plasma membrane in control embryos but are mis-localized to the nucleus and cytoplasm in aplexone-treated embryos. G, Table quantifying the subcellular localization of mCherry-rhoCAAX in control or aplexone-treated embryos.

The HMGCR pathway is responsible for the synthesis of isoprene derivatives, which are substrates for protein prenylation, a post-translational modification essential for multiple cellular processes including cell migration, proliferation and membrane trafficking (Santos and Lehmann, 2004; Thorpe et al., 2004; Bifulco, 2005; D'Amico et al., 2007). Treatment with aplexone severely compromises the migration of ECs raising the possibility that aplexone inhibits venous angiogenesis by modulating protein prenylation. To evaluate the impact of aplexone on protein prenylation, we generated a chimeric protein with mCherry fused to a CAAX motif from RhoA specific for geranylgeranylation, CLVL (Roberts et al., 2008). As expected, the chimeric protein was primarily localized to the plasma membrane in control embryos (FIG. 6E). Upon treatment with aplexone, the chimeric protein was no longer localized predominantly to the membrane, and fluorescent signals were present on the membrane as well as in the cytoplasm and nucleus (FIG. 6F). Similar results were observed when we analyzed membrane localization of mCherry proteins fused with a CAAX motif from Ras specific for farnesylation, CVLS (Roberts et al., 2008) (data not shown). These findings demonstrate the inhibitory effect of aplexone on protein prenylation. We then treated zebrafish embryos with GGTI-2133, a geranylgeranyl transferase inhibitor, or L744,832, a farnesyl transferase inhibitor, to evaluate their impacts on venous angiogenesis. We found that while L744,832 does not affect the formation of the CVP (FIG. 6B), embryos injected with GGTI-2133 exhibited CVP phenotypes reminiscent of aplexone treatment (FIG. 6C), suggesting aplexone acts in a Rho-dependent manner. We further analyzed the effects of Rho signaling in CVP formation by blocking the activity of Rho kinases (ROCKs), specific downstream targets of Rho signaling (Riento and Ridley, 2003), using a selective inhibitor, Rockout (Yarrow et al., 2005). Treatment with Rockout recapitulated the caudal vein phenotype of aplexone treatment (FIG. 6D). Without wishing to be bound by any particular mechanism, we suggest that, taken together, our findings indicate that farnesylation is not required for CVP formation and that aplexone inhibits CVP formation and EC migration primarily by interfering with protein geranylgeranylation.

Figure 7:
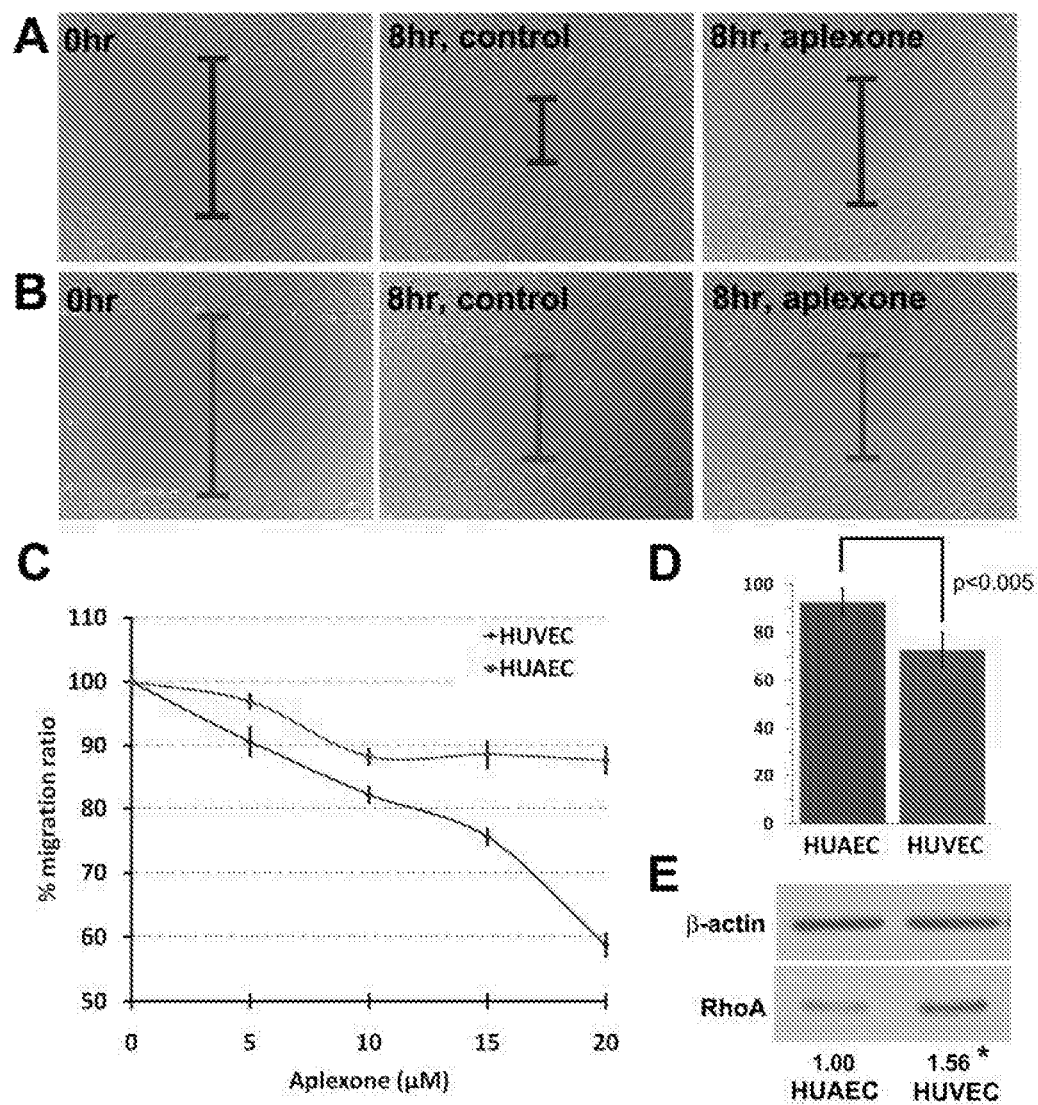
FIG. 7 shows that aplexone inhibits migration of human endothelial cells. A-B, Representative images of wound healing assay. A-B, HUVECs (A) and HUAECs (B) at 0 hr and 8 hrs after wounds were made. C, The percentage of the migration distance of HUVECs and HUAECs at various aplexone concentrations for 8 hrs after wounds were made. D, Graph illustrates the inhibitory effect of 40 µM Rockout, a Rho kinase inhibitor, on HUVECs and HUAECs. E, A representative image of Western blot for total RhoA in HUAECs and HUVECs. The same blot was probed with anti-β-actin antibody to verify equal loading. The average of the relative amounts of total RhoA in HUAECs and HUVECs collected from four independent experiments is indicated under the Western blot (*, p<0.05).
Figure 10:
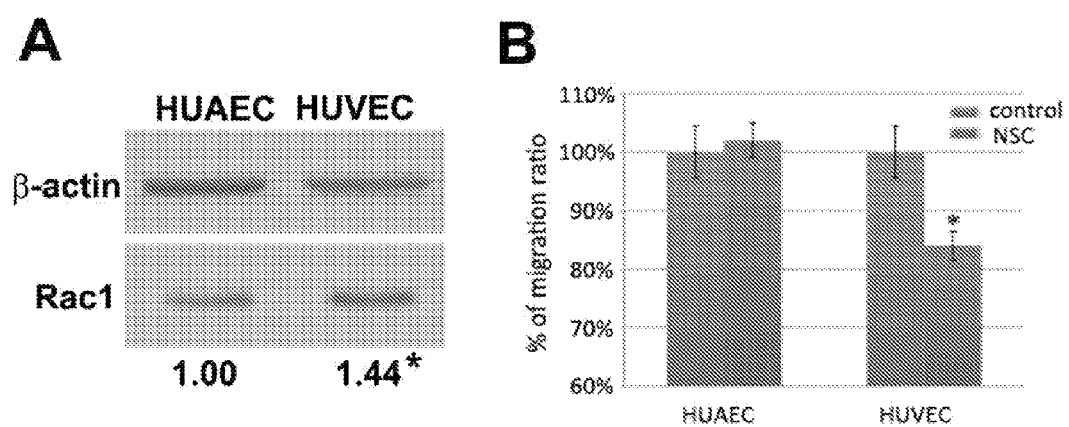
FIG. 10 shows that the suppression of Rac1 activity preferentially inhibits the migration of venous endothelial cells.

E. Aplexone Differentially Regulates the Migration of Human Arterial and Venous Endothelial Cells We next investigated whether aplexone also regulates the migration of human ECs in a wound healing assay using human umbilical vein endothelial cells (HUVECs) and human umbilical artery endothelial cells (HUAECs). Like zebrafish venous ECs, the migration of HUVECs was inhibited by treatment with aplexone and the inhibitory effect became more apparent as the concentration of aplexone increased (FIG. 7A,C). Interestingly, HUAECs exhibited a different response to aplexone. HUAEC migration is unaffected by 5 µM aplexone, a dosage sufficient to impede the migration of HUVECs (FIG. 7C). At a concentration of 10 µM, a small, but significant, impediment in HUAEC migration (10%, $p<0.05$) was noted but this inhibitory effect did not appear to have a linear relationship to the dosage of aplexone (FIG. 7C). The differential threshold for response to aplexone between HUVECs and HUAECs indicates that ECs of arterial and venous origins have innate differences in sensitivity to changes in the activity of the HMGCR pathway and suggests that these cells may have differential amounts of proteins subject to geranylgeranylation. Indeed, Western analysis showed that HUVECs have about 50% more RhoA and Rac1, two proteins of the Rho family GTPases that require geranylgeranyl modification for their biological functions (Roberts et al., 2008), than HUAECs (FIG. 7E and FIG. 10A), demonstrating an arteriovenous difference in the amounts of CAAX-motif containing proteins. Rho and Rac play pivotal roles in regulating cytoskeletal dynamics and cell migration. We found that blocking the activity of Rho kinase or Rac1 reduces the migration of HUVECs but has limited impact on the migration of HUAECs (FIG. 7D), demonstrating that venous ECs are more sensitive to changes of Rho or Rac activity than arterial ECs.

Consistently, zebrafish ECs also showed a differential threshold for responding to aplexone treatment depending on their arteriovenous origins. The vascular defects of zebrafish embryos exposed to 10 µM aplexone are restricted to development of the CVP and the secondary sprouts. However, while embryos subjected to the treatment of a high dose of aplexone (30 µM) develop primary sprouts, these primary ISVs are shorter and never reach the dorsal side of the somites (FIG. 8C'), demonstrating that aorta-derived ECs do respond to aplexone, but require higher dosages when compared to ECs of venous origin.

Figure 8:
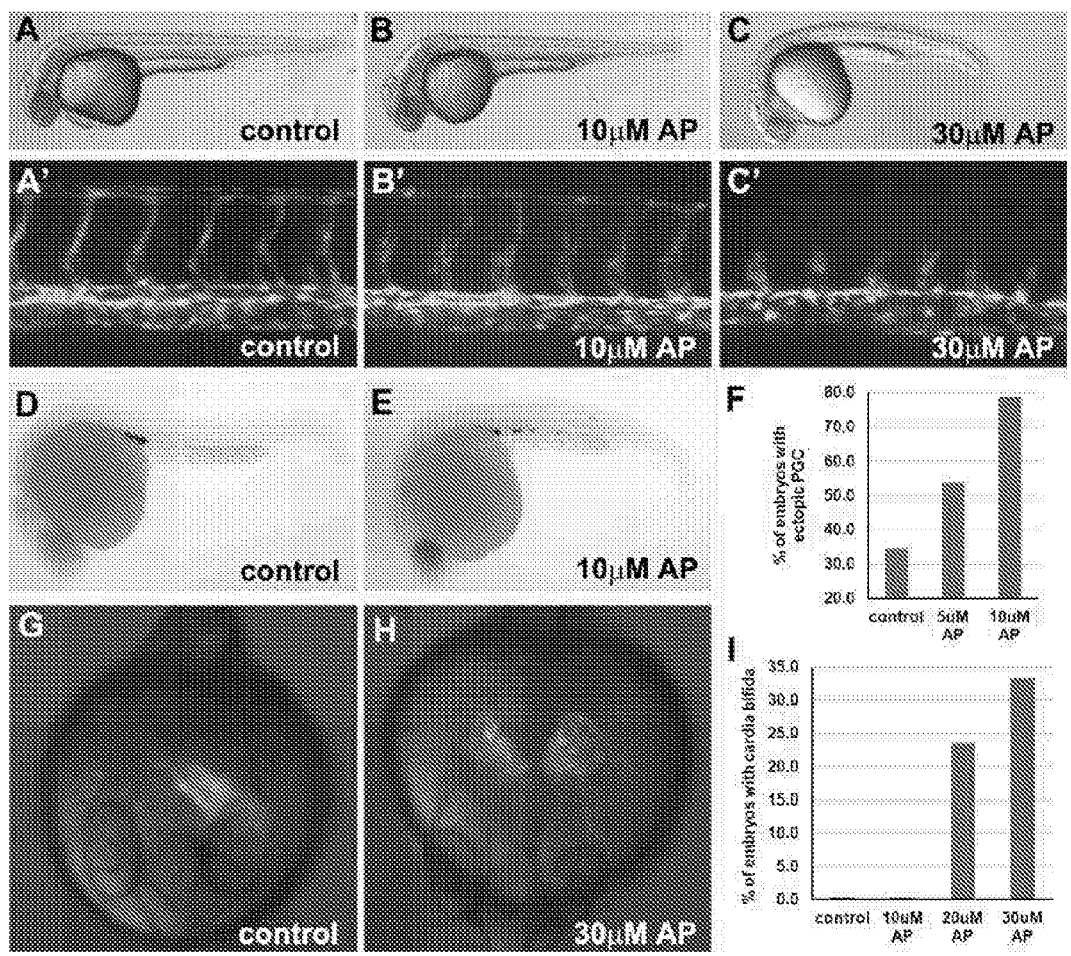
FIG. 8 shows that aplexone inhibits migration of germ cells, cardiomyocytes and arterial endothelial cells. A,B,C, Overall phenotype of control and aplexone-treated embryos at 30 hpf. A',B',C', Vasculature in trunk. Note that 10 µM aplexone does not affect the development of primary ISVs but 30 µM aplexone inhibits the growth of primary ISVs. D-E, Germ cells in control and aplexone treated embryos at 24 hpf were detected by in situ hybridization using the nanos probe. F, The percentage of embryos with ectopic primordial germ cells in control (n=26), 5 µM (n=13), and 10 µM (n=14) aplexone-treated embryos. G-H, Cardiomyocytes migrate to the midline and form a heart tube in Tg(myl7:GFP) embryos by 24 hpf(G), but fail to migrate to midline in embryos treated with 30 µM aplexone (H). I, The percentage of embryos with cardia bifida in control (n=16) and 10 µM-(n=17), 20 µM-(n=17) and 30 µM-(n=18) aplexone-treated embryos.

In addition to the vascular defects, embryos treated with a higher dosage of aplexone exhibit multiple morphogenic abnormalities. Embryos exposed to a low dosage of aplexone (10 µM) have a relatively normal body shape and, except for a defect in germ cell migration, the morphogenesis of the internal organs is normal (FIG. 8B,E,F). On the contrary, embryos treated with 30 µM aplexone have additional defects in the fusion of the bilaterally positioned cardiac primordia (FIG. 8C,H,I). While these embryos are shorter than control embryos, no evidence suggesting that this is a result of developmental delay was noted. Without wishing to be bound by any particular mechanism we suggest that, taken together, our findings demonstrate an important role for the HMGCR pathway in regulating the migration of angioblasts, cardiac precursors and primordial germ cells, and a cell type-specific variation in sensitivity to changes in activity of the HMGCR pathway.

References

Bifulco, M. (2005). Role of the isoprenoid pathway in ras transforming activity, cytoskeleton organization, cell proliferation and apoptosis. *Life Sci* 77, 1740-9, Castellano, S., Fiji, H. D., Kinderman, S. S., Watanabe, M., Leon, P., Tamanoi, F. and Kwon, O. (2007). Small-molecule inhibitors of protein geranylgeranyltransferase type I. *J Am Chem Soc* 129, 5843-5.

Chen, M., Philipp, M., Wang, J., Premont, R. T., Garrison, T. R., Caron, M. G., Lefkowitz, R, J. and Chen, W. (2009). G Protein-coupled receptor kinases phosphorylate LRP6 in the Wnt pathway. *J Biol Chem* 284, 35040-8.

Chen, W., Burgess, S, and Hopkins, N. (2001). Analysis of the zebrafish smoothened mutant reveals conserved and divergent functions of hedgehog activity. *Development* 128, 2385-96.

Choi, J., Dong, L., Ahn, J., Dao, D., Hammerschmidt, M. and Chen, J. N. (2007). FoxH1 negatively modulates flk1 gene expression and vascular formation in zebrafish. *Dev Biol* 304, 735-44.

Cleaver, O. and Melton, D. A. (2003). Endothelial signaling during development. *Nat Med* 9, 661-8.

D'Amico, L., Scott, I. C., Jungblut, B. and Stainier, D. Y. (2007). A mutation in zebrafish hmgcr1b reveals a role for isoprenoids in vertebrate heart-tube formation. *Curr Biol* 17, 252-9.

Ellertsdottir, E., Lenard, A., Blum, Y., Krudewig, A., Herwig, L., Affolter, M. and Belting, H. G. (2010). Vascular morphogenesis in the zebrafish embryo. *Dev Biol* 341, 56-65, Gerety, S. S, and Anderson, D. J. (2002). Cardiovascular ephrinB2 function is essential for embryonic angiogenesis. *Development* 129, 1397-410.

Gerety, S. S., Wang, H. U., Chen, Z. F. and Anderson, D. J. (1999). Symmetrical mutant phenotypes of the receptor EphB4 and its specific transmembrane ligand ephrin-B2 in cardiovascular development. *Mol Cell* 4, 403-14.

Herbert, S. P., Huisken, J., Kim, T. N., Feldman, M. E., Houseman, B. T., Wang, R. A., Shokat, K. M. and Stainier, D. Y. (2009). Arterial-venous segregation by selective cell sprouting: an alternative mode of blood vessel formation. *Science* 326, 294-8.

Hogan, B. M., Herpers, R., Witte, M., Helotera, H., Alitalo, K., Duckers, H. J. and Schulte-Merker, S. (2009). Vegfc/Flt4 signalling is suppressed by Dll4 in developing zebrafish intersegmental arteries. *Development* 136, 4001-9.

Horton, J. D., Goldstein, J. L. and Brown, M. S. (2002). SREBPs: transcriptional mediators of lipid homeostasis. *Cold Spring Harb Symp Quant Biol* 67, 491-8.

Huang, C. J., Tu, C. T., Hsiao, C. D., Hsieh, F. J. and Tsai, H. J. (2003). Germ-line transmission of a myocardium-specific GFP transgene reveals critical regulatory elements in the cardiac myosin light chain 2 promoter of zebrafish. *Dev Dyn* 228, 30-40.

Ii, M. and Losordo, D. W. (2007). Statins and the endothelium. *Vascul Pharmacol* 46, 1-9.

Irizarry, R. A., Hobbs, B., Collin, F., Beazer-Barclay, Y. D., Antonellis, K. J., Scherf, U. and Speed, T. P. (2003). Exploration, normalization, and summaries of high density oligonucleotide array probe level data. *Biostatistics* 4, 249-64.

Isogai, S., Lawson, N. D., Torrealday, S., Horiguchi, M. and Weinstein, B. M. (2003). Angiogenic network formation in the developing vertebrate trunk. *Development* 130, 5281-90.

Jin, S. W., Beis, D., Mitchell, T., Chen, J. N. and Stainier, D. Y. (2005). Cellular and molecular analyses of vascular tube and lumen formation in zebrafish. *Development* 132, 5199-209.

Kimmel, C, B., Ballard, W. W., Kimmel, S. R., Ullmann, B. and Schilling, T. F. (1995). Stages of embryonic development of the zebrafish. *Dev Dyn* 203, 253-310.

Lawson, N. D., Scheer, N., Pham, V. N., Kim, C. H., Chitnis, A. B., Campos-Ortega, J. A. and Weinstein, B. M. (2001). Notch signaling is required for arterial-venous differentiation during embryonic vascular development. *Development* 128, 3675-83.

Lawson, N. D., Vogel, A. M. and Weinstein, B. M. (2002). sonic hedgehog and vascular endothelial growth factor act upstream of the Notch pathway during arterial endothelial differentiation. *Dev Cell* 3, 127-36.

Lucitti, J. L., Jones, E. A., Huang, C., Chen, J., Fraser, S. E. and Dickinson, M. E. (2007). Vascular remodeling of the mouse yolk sac requires hemodynamic force. *Development* 134, 3317-26.

Makanya, A. N., Hlushchuk, R. and Djonov, V. G. (2009). Intussusceptive angiogenesis and its role in vascular morphogenesis, patterning, and remodeling. *Angiogenesis* 12, 113-23.

Riento, K. and Ridley, A. J. (2003). Rocks: multifunctional kinases in cell behaviour. *Nat Rev Mol Cell Biol* 4, 446-56.

Ro, H., Soun, K., Kim, E. J. and Rhee, M. (2004), Novel vector systems optimized for injecting in vitro-synthesized mRNA into zebrafish embryos. *Mol Cells* 17, 373-6.

Roberts, P. J., Mitin, N., Keller, P. J., Chenette, E. J., Madigan, J. P., Currin, R. O., Cox, A. D., Wilson, O., Kirschmeier, P. and Der, C. J. (2008). Rho Family GTPase modification and dependence on CAAX motif-signaled posttranslational modification. *J Biol Chem* 283, 25150-63, Santos, A. C. and Lehmann, R. (2004). Isoprenoids control germ cell migration downstream of HMGCoA reductase. *Dev Cell* 6, 283-93.

Sawamiphak, S., Seidel, S., Essmann, C. L., Wilkinson, G. A., Pitulescu, M. E., Acker, T. and Acker-Palmer, A. Ephrin-B2 regulates VEGFR2 function in developmental and tumour angiogenesis. *Nature* 465, 487-91.

Sehnert, A. J., Huq, A., Weinstein, B. M., Walker, C., Fishman, M. and Stainier, D. Y. (2002). Cardiac troponin T is essential in sarcomere assembly and cardiac contractility. *Nat Genet* 31, 106-10.

Smyth, G. K. (2004). Linear models and empirical bayes methods for assessing differential expression in microarray experiments. *Stat Appl Genet Mol Biol* 3, Article 3.

Team, R. D. C. (2009). R: A language and environment for statistical computing, (ed.

Thorpe, J. L., Doitsidou, M., Ho, S. Y., Raz, E. and Farber, S. A. (2004). Germ cell migration in zebrafish is dependent on HMGCoA reductase activity and prenylation. *Dev Cell* 6, 295-302.

Torres-Vazquez, J., Kamei, M. and Weinstein, B. M. (2003). Molecular distinction between arteries and veins. *Cell Tissue Res* 314, 43-59.

Walsh, D. P. and Chang, Y.-T. (2006). Chemical genetics. *Chem Rev* 106, 2476-2530.

Wang, H. U., Chen, Z. F. and Anderson, D. J. (1998). Molecular distinction and angiogenic interaction between embryonic arteries and veins revealed by ephrin-B2 and its receptor Eph-B4. *Cell* 93, 741-53, Westerfield, M. (2000). The zebrafish book: The University of Oregon Press.

Williams, C., Kim, S. H., Ni, T. T., Mitchell, L., Ro, H., Penn, J. S., Baldwin, S. H., Solnica-Krezel, L. and Zhong, T. P. (2010). Hedgehog signaling induces arterial endothelial cell formation by repressing venous cell fate. *Dev Biol* 341, 196-204.

Yarrow, J. C., Totsukawa, G., Charras, G. T. and Mitchison, T. J. (2005). Screening for cell migration inhibitors via automated microscopy reveals a Rho-kinase inhibitor. *Chem Biol* 12, 385-95.

Yi, P., Han, Z., Li, X. and Olson, E. N. (2006). The mevalonate pathway controls heart formation in Drosophila by isoprenylation of Ggamma1. *Science* 313, 1301-3.

Zhong, T. P., Childs, S., Leu, J. P. and Fishman, M. C. (2001). Gridlock signalling pathway fashions the first embryonic artery. *Nature* 414, 216-20.

Zhu, X., Lan, J. and Kwon, O. (2003). An expedient phosphine-catalyzed [4+2] annulation: synthesis of highly functionalized tetrahydropyridines. *J Am Chem Soc* 125, 4718-4717.

Zon, L. I. and Peterson, R. T. (2005). In vivo drug discovery in the zebrafish. *Nat Rev Drug Discov* 4, 35-44.

Example 3

Methods for the Experiments Described in Example 4

General Experimental

Methods not described below were carried out as described in Example 1.

All reactions were performed under argon atmospheres in oven-dried glassware with dry solvent and anhydrous conditions. Unless otherwise stated, all reagents were purchased from commercial suppliers and used without further purification. Toluene, dichloromethane (DCM) and methanol were freshly distilled from $CaH_2$. THF was distilled from sodium benzophenone ketyl prior to use. Organic solutions were concentrated under reduced pressure on a rotary evaporator or an oil pump. All tetrahydropyridine ester compounds were synthesized according to the procedures reported previously.[9] Tebbe reagent (~1.0 M in toluene) was synthesized according to the procedure reported by Grubbs.[21] Reactions were monitored through thin layer chromatography (TLC) on silica gel-precoated glass plates (0.25 mm thickness, SiliCycle silica gel). Chromatograms were visualized through fluorescence quenching with UV light at 254 nm. Flash column chromatography was performed using SiliCycle Silica-P Flash silica gel (60 Å pore size, 40-63 um). Infrared spectra were recorded using a Perkin-Elmer Spectrum One FT-IR spectrometer. $^1H$ and $^{13}C$ NMR spectra were recorded in $CDCl_3$ on Bruker Avance 500, ARX-500, or ARX-400 spectrometers, as indicated. Chemical shifts (δ ppm) are provided relative to tetramethylsilane (TMS), with the resonance of the undeuterated solvent or TMS as the internal standard, $^1H$ NMR spectral data are reported as follows: chemical shift, multiplicity (s=singlet; d=doublet; t=triplet; q=quartet; m=multiplet), coupling constant(s) (Hz), integration. $^{13}C$ NMR spectral data are reported in terms of chemical shift. Samples were analyzed on a Waters LCT Premier XE Time of Flight Instrument controlled by MassLynx 4.1 software. Samples were infused using direct loop injection from a Waters Acquity UPLC into the Multi Mode Ionization source. The lock mass standard for accurate mass determination was Leucine Enkephalin (Sigma L9133).

Results of the analyses are shown in Example 6.

Synthetic Methods

General Procedure for the Formation of Aplexone and Aplexone Analogs (13 and 17-37)

To a solution of tetrahydropyridine ester (1.0 mmol) and anhydrous pyridine (0.3 eq.) in dry THF (10 mL), Tebbe reagent (~10 M in toluene, 3.0 eq.) was added dropwise for 10 minutes at −78° C. (dry ice in acetone). The reddish mixture was allowed to be stirred overnight at room temperature while a cooling bath was warmed by evaporation of dry ice. 15% aqueous NaOH (0.5 mL) was added dropwise at −78° C. (acetone/dry ice) and $CH_4$ was evolved. After 1 hour, 10 mL THF was added to the reaction mixture. Then the mixture was stirred for another 4 hours at room temperature. The organic solution was filtered through Celite pad and filtrate was concentrated. The crude residue was purified through flash column chromatography on the silica gel using 10-25% ethyl acetate and 1% $Et_3N$ in hexanes to afford the diene intermediate. To a solution of the diene intermediate in acetone (20 mL), 2 M HCl (2 mL) was added dropwise at room temperature. After 10 minutes, the solution was concentrated, the saturated $NaHCO_3$ (10 mL) was added, and the mixture was extracted by $CH_2Cl_2$ (3×10 mL). The organic phase was dried by anhydrous $Na_2SO_4$ and concentrated. The crude residue was purified through flash column chromatography on the silica gel using 25-50% ethyl acetate in hexanes to afford the product.

Aplexone: 80% yield, two steps; IR (film) $v_{max}$ 3062, 2920, 1666, 1160 cm$^{-1}$; $^1H$ NMR (500 MHz, CDCl$_3$): δ 7.64 (d, J=8.2 Hz, 2H), 7.27-7.19 (m, 7H), 6.92 (br, 1H), 5.38 (d, J=5.4 Hz, 1H), 4.46 (d, J=18.4 Hz, 1H), 3.38 (ddd, J=18.4, 5.6, 3.3 Hz, 1H), 2.70-2.67 (m, 2H), 2.38 (s, 3H), 2.22 (s, 3H); $^{13}C$ NMR (125 MHz, CDCl$_3$): δ 196.4, 143.3, 138.2, 137.1, 136.9, 136.2, 129.5, 128.5, 127.7, 127.0, 126.9, 52.1, 38.9, 27.6, 24.9, 21.4; HRMS (m/z): [M+H]$^+$ calcd. for $C_{20}H_{21}NO_3SH$, 356.1315. found, 356.1299.

Synthesis of Aplexone Analogs 3 and 4[25]

Aplexone (0.28 mmol) was dissolved in chloroform along with Pd(PPh$_3$)$_4$ (5.6 μmol) and ZnCl$_2$ (0.14 mmol). Ph$_2$SiH$_2$ (0.56 mmol) was added dropwise to the solution and the mixture was stirred at −20° C. for 2 days. The reaction mixture was filtered through celite pad and the filtrate was concentrated. The crude residue was purified through flash column chromatography on the silica gel using 25% ethyl acetate in hexanes to afford the product as colorless oil in 80% yield. Two diastreoisomers (4:1) were obtained. 3: IR (film) $v_{max}$ 3057, 2953, 1711, 1156 cm$^{-1}$; $^1$NMR (500 MHz, CDCl$_3$): δ 7.60 (d, J=8.2 Hz, 2H), 7.32-7.24 (m, 7H), 4.81 (t, J=5.0 Hz, 1H), 3.79 (dd, J=13.6, 5.0 Hz, 1H), 3.76 (dd, J=13.6, 5.0 Hz, 1H), 2.62-2.58 (m, 1H), 2.45 (s, 3H), 2.16 (s, 3H), 2.11-2.07 (m, 2H), 1.85-1.79 (m, 1H), 1.76-1.69 (m, 1H); $^{13}C$ NMR (125 MHz, CDCl$_3$): δ 208.2, 143.2, 139.3, 136.4, 129.3, 128.2, 127.4, 127.1, 127.0, 57.6, 46.7, 43.5, 28.1, 27.9, 21.4, 20.8; HRMS (m/z): [M+Na]$^+$ calcd. for $C_{20}H_{23}NO_3SNa$, 380.1291. found, 380.1307. 4: IR (film) $v_{max}$ 3060, 2931, 1708, 1157 cm$^{-1}$; $^1H$ NMR (500 MHz, CDCl$_3$): δ 7.75 (d, J=8.3 Hz, 2H), 7.31-7.27 (m, 4H), 7.23-7.21 (m, 3H), 5.32 (d, J=4.1 Hz, 1H), 3.98 (dd, J=14.5, 3.5 Hz, 1H), 2.97 (dd, J=14.5, 12.0 Hz, 1H), 2.50-2.45 (m, 1H), 2.44 (s, 3H), 2.38-2.34 (m, 1H), 2.07 (s, 3H), 1.89-1.82 (m, 2H), 1.50-1.44 (m, 1H); $^{13}C$ NMR (125 MHz, CDCl$_3$): δ 208.7, 143.3, 137.9, 137.7, 129.7, 128.6, 127.0, 126.9, 126.6, 54.2, 47.9, 42.0, 28.2, 26.7, 22.1, 21.4; HRMS (ink): [M+H]$^+$ calcd. for $C_{20}H_{23}NO_3SH$, 358.1471. found, 358.1474.

Synthesis of Aplexone Analog 5

To a mixture of Aplexone (0.44 mmol) and CuBr (0.022 mmol) in THF, neat Me$_3$Al (0.05 mL) was added dropwise at −78° C. The reaction mixture was allowed to be stirred overnight at room temperature while a cooling bath was warmed by evaporation of dry ice. Then 2 mL hexanes was added and the reaction was quenched by careful addition of 0.07 mL of 2.5 M NH$_4$Cl solution at −78° C. The reaction mixture was warmed up to rt slowly. 0.1 g MgSO$_4$ was added. The reaction mixture was filtered through celite pad and the filtrate was concentrated. The crude residue was purified through flash column chromatography on the silica gel using 33% ethyl acetate in hexanes to afford the product as colorless oil. 60% yield; IR (film) $v_{max}$ 3060, 2928, 1710, 1159 cm$^{-1}$; $^1H$ NMR (500 MHz, CDCl$_3$): δ 7.79 (d, =8.2 Hz, 2H), 7.36-7.31 (m, 4H), 7.27-7.24 (m, 3H), 5.33 (d, J=5.1 Hz, 1H), 3.95 (dd, J=14.0, 3.9 Hz, 1H), 2.91 (dd, J=13.7, 11.4 Hz, 1H), 2.47 (s, 3H), 2.31-2.24 (m, 2H), 2.14 (s, 3H), 1.93-1.87 (m, 1H), 1.51 (ddd, J=14.1, 12.7, 5.6 Hz, 1H), 0.83 (d, J=6.5 Hz, 3H); $^{13}C$ NMR (125 MHz, CDCl$_3$): δ 209.4, 143.4, 138.1, 137.8, 129.7, 128.6, 127.0, 126.9, 126.5, 55.6, 54.8, 42.8, 34.6, 30.9, 27.8, 21.4, 19.8; HRMS (m/z): [M+H]$^+$ calcd. for C$_{21}$H$_{25}$NO$_3$SH, 372.1628. found, 372.1613.

Synthesis of Aplexone Analogs 6 and 7

To a solution of Aplexone (0.22 mmol) in CH$_2$Cl$_2$ (6 mL) at −78° C., 0.55 mL Diisobutylaluminium hydride (DIBAL, 1.0 M in CH$_2$Cl$_2$) was added dropwise. The reaction was finished in 1 hour. Water (0.03 mL) was added at −78° C. and the reaction was warmed up to rt. 0.1 g anhydrous Na$_2$SO$_4$ was added. The reaction mixture was filtered through celite pad and the filtrate was concentrated. The crude residue was purified through flash column chromatography on the silica gel using 33% ethyl acetate in hexanes to afford the product as white solid. Two diastreoisomers (1.25:1) were obtained in 90% yield. The diastreoisomers could be separated by prep. HPLC. 6: IR (film) $v_{max}$ 3519, 2972, 1332, 1156 cm$^{-1}$; $^1$H NMR (500 MHz, CDCl$_3$): δ 7.71 (d, J=8.3 Hz, 2H), 7.31-7.22 (m, 7H), 5.72 (s, 1H), 5.32 (t, J=3.8 Hz, 1H), 4.19-4.15 (m, 2H), 3.30 (ddd, J=18.0, 5.2, 2.8 Hz, 1H), 2.4 (br, 2H), 2.40 (s, 3H), 1.54 (br, 1H), 1.14 (d, J=6.5 Hz, 3H); $^{13}$C NMR (125 MHz, CDCl$_3$): δ 143.1, 138.9, 138.3, 137.5, 129.4, 128.3, 127.4, 127.2, 127.0, 118.6, 69.9, 52.7, 39.2, 26.0, 21.4, 21.2; HRMS (m/z): [M+Na]$^+$ calcd. for C$_{20}$H$_{23}$NO$_3$SNa, 380.1291. found, 380.1286, 7: IR (film) $v_{max}$ 3519, 2972, 1332, 1156 cm$^{-1}$; $^1$H NMR (500 MHz, CDCl$_3$): δ 7.67 (d, J=8.2 Hz, 2H), 7.33-7.18 (m, 7H), 5.72 (d, J=3.3 Hz, 1H), 5.29 (d, J=6.4 Hz, 1H), 4.15-4.11 (m, 2H), 3.34 (ddd, J=20.4, 5.1, 2.4 Hz, 1H), 2.47-2.36 (m, 5H), 1.58 (br, 1H), 1.19 (d, J=6.4 Hz, 3H); $^{13}$C NMR (125 MHz, CDCl$_3$): δ 143.1, 139.0, 138.0, 137.4, 129.4, 128.3, 127.4, 127.2, 126.9, 117.8, 69.3, 52.7, 40.0, 26.1, 21.5, 21.4; HRMS (m/z): [M+H]$^+$ calcd. for C$_{20}$H$_{23}$NO$_3$SH, 358.1471. found, 358.1484.

Synthesis of Aplexone Analog 8

Anhydrous diisopropylamine (0.05 ml) was dissolved in THF (2 mL), cooled to −30° C. (dry ice in acetonenitrile), and n-BuLi (1.4 M in hexanes, 0.26 mL) was slowly added at this temperature, and stirring was continued for 30 min to form lithium diisopropylamide (LDA) solution, Aplexone (0.14 mmol) was then added dropwise in THF (1 mL) to this LDA solution at −30° C. After 30 min, the allyl bromide (0.17 mmol) was added dropwise to the reaction solution. The reaction mixture was stirred for 1 h and then the reaction was quenched by careful addition of 0.07 mL of 2.5 M NH$_4$Cl solution at −30° C. and warmed up to rt. The mixture was extracted by Et$_2$O (3×10 mL). The organic phase was dried by anhydrous Na$_2$SO$_4$ and concentrated. The crude residue was purified through The crude residue was purified through flash column chromatography on the silica gel using 33% ethyl acetate in hexanes to afford the product as colorless oil in 71% yield. IR (film) $v_{max}$ 3064, 2924, 1667, 1160 cm$^{-1}$; $^1$H NMR (500 MHz, CDCl$_3$): δ 7.67 (d, J=8.3 Hz, 2H), 7.25-7.22 (m, 5H), 7.18-7.16 (m, 2H), 6.93-6.91 (m, 1H), 5.83-5.75 (m, 1H), 5.39 (t, J=3.9 Hz, 1H), 5.03-4.98 (m, 2H), 4.48 (d, J=18.5 Hz, 1H), 3.39 (ddd, J=18.6, 5.5, 3.3 Hz, 1H), 2.76-2.70 (m, 4H), 2.38-2.34 (m, 2H), 2.23 (s, 3H); $^{13}$C NMR (125 MHz, CDCl$_3$): δ 196.4, 147.0, 138.1, 137.4, 137.0, 136.9, 136.2, 129.0, 128.5, 127.7, 127.0, 126.9, 115.5, 52.1, 38.9, 35.0, 34.9, 27.7, 24.9; HRMS (m/z): [M+Na]$^+$ calcd. for C$_{23}$H$_{25}$NO$_3$SNa, 418.1447. found, 418.1462.

Synthesis of Aplexone Analogs 11 and 12

To a solution of aplexone (0.48 mmol) and ethylene glycol (2.40 mmol) in benzene (6 mL), tosylate acid (0.15 mmol) was added. The mixture was stirred under reflux for 4 hours and the by-product water was removed with the Dean-Stark apparatus. The mixture was concentrated. The crude residue was purified by flash column chromatography on the silica gel using 33% ethyl acetate in hexanes to afford the ketal intermediate 9 as colorless oil in 92% yield. To a solution of the ketal intermediate 9 (0.44 mmol) in THF (5 mL), the Na/naphthalene THF solution (34 mg Na and 0.24 g naphthalene in 0.7 mL THF, The solution was stirred at room temperature for 2 hours before using) was added dropwise at −78° C. After 1 hour, the reaction mixture was warmed up to room temperature and the reaction was continued for another hour. The reaction was quenched by water (5 mL) carefully. The mixture was extracted by ethyl acetate (3×10 mL). The organic phase was dried over anhydrous Na$_2$SO$_4$ and concentrated. The crude residue was purified by flash column chromatography on the silica gel using 10% methanol in ethyl acetate to afford the amine intermediate 10 in 56% yield. To a solution of the amine intermediate 10 (0.25 mmol) in methanol (5 mL), 2 M HCl (1.0 mL) was added dropwise at room temperature. After 48 hours, the saturated NaHCO$_3$ (3.0 mL) was added to the reaction system and the mixture was extracted by ethyl acetate (3×10 mL). The organic phase was dried over anhydrous Na$_2$SO$_4$ and concentrated. The crude residue was purified by flash column chromatography on silica gel using 10% methanol in ethyl acetate to afford final product 11 as yellow oil in 86% yield; IR (film) $v_{max}$ 3321, 3028, 2886, 1663, 1250 cm$^{-1}$; $^1$H NMR (500 MHz, CDCl$_3$): δ 7.35-7.29 (m, 4H), 7.26-7.22 (m, 1H), 6.96 (br, 1H), 3.83 (d, J=12.0 Hz, 1H), 3.74 (dd, J=8.7, 5.3 Hz, 1H), 3.57 (ddd, J=17.0, 5.9, 3.6 Hz, 1H), 2.45-2.44 (m, 2H), 2.28 (s, 3H); $^{13}$C NMR (125 MHz, CDCl$_3$): δ 197.6, 143.5, 139.0, 138.6, 128.5, 127.4, 126.4, 56.9, 44.5, 34.8, 25.0; HRMS (m/z): [M+H]$^+$ calcd. for C$_{13}$H$_{15}$NOH, 202.1226. found, 202.1222. To a solution of 11 (0.50 mmol) and NaH (1.0 mmol) in DMF (4 mL), benzyl bromide (1.0 mmol) was added dropwise at room temperature. After 20 hours, saturated NH$_4$Cl (2.0 mL) was added and the mixture was extracted by ethyl acetate (3×10 mL). The organic phase was dried over anhydrous Na$_2$SO$_4$ and concentrated. The crude residue was purified by flash column chromatography on the silica gel using 33% ethyl acetate in hexanes to afford final product 12 as yellow oil in 78% yield; IR (film) $v_{max}$ 3027, 2914, 1665, 1127 cm$^{-1}$; $^1$H NMR (500 MHz, CDCl$_3$): δ 7.43-7.36 (m, 4H), 7.32-7.27 (m, 5H), 7.24-7.20 (m, 1H), 6.98-6.97 (m, 1H), 3.79 (d, J=15.4 Hz, 1H), 3.61-3.57 (m, 2H), 3.08 (d, J=13.4 Hz, 1H), 2.99 (ddd, J=17.3, 5.3, 3.0 Hz, 1H), 2.68-2.64 (m, 2H), 2.30 (s, 3H); $^{13}$C NMR (125 MHz, CDCl$_3$): δ 197.4, 142.3, 138.7, 138.0, 137.8, 128.6, 128.5, 128.2, 127.7, 127.4, 126.8, 62.4, 58.8, 49.6, 35.4, 25.0; HRMS (m/z): [M+H]$^+$ calcd. for C$_{20}$H$_{21}$NOH, 292.1696. found, 292.1687.

Synthesis of Aplexone Analog 16

To a solution of ethyl 4-piperidone-3-carboxylate hydrochloride (2.0 g, 9.6 mmol) in DCM (40 mL) was added dropwise at 0° C. Et$_3$N (5.3 mL, 4.0 eq.). After 30 mins, a solution of TsCl in DCM (20 mL) was added dropwise to the mixture. After stirring over night at room temperature, the reaction mixture was washed by 2 N HCl (3×30 mL), saturated NaHCO$_3$ (2×30 mL), and brine (2×30 mL). The organic phase was dried over anhydrous Na$_2$SO$_4$ and concentrated. The crude residue was used for the next step without any purification. To a stirred solution of the crude residue (~9.6 mmol) in absolute ethanol (15 ml) was added dropwise at 0° C. a solution of NaBH$_4$ (363 mg, 9.6 mmol) in absolute ethanol (15 mL). Stirring was continued for an additional 13 h, during which the reaction temperature rose slowly to room temperature. A few drops of aqueous acetic acids followed by water were added to the reaction mixture which was then extracted with DCM (3×30 mL). The organic phase was dried over anhydrous Na$_2$SO$_4$ and concentrated. The crude residue was purified by flash column chromatography on the silica gel using 33% ethyl acetate in hexanes to afford the product alcohol 14 in 54% yield, two steps. To a stirred solution of the alcohol 14 (1.7 g, 5.2 mmol) and Et$_3$N (2.2 mL, 3.0 eq.) in ether (12 mL) was added dropwise at 0° C. methanesulfonyl chloride (0.8 mL). The reaction was stirred for 3 h after which a solution of DBU (1.5 mL) in ether (6 mL) was added to it. Stirring was continued for an additional 4 h after which the reaction mixture was quenched by the addition of water, and then extracted with ether (3×30 mL). The organic phase was dried over anhydrous Na$_2$SO$_4$ and concentrated. The crude residue was purified by flash column chromatography on the silica gel using 20% ethyl acetate in hexanes to afford the product α,β-unsaturated ester 15 in 70% yield, two steps. The aplexone analog 16 was synthesized following the same procedure of Aplexone synthesis from the α,β-unsaturated ester 15 in 80% yield, two steps. Colorless oil, 30% overall yield, 6 steps; IR (film) ν$_{max}$ 3063, 2925, 1668, 1165 cm$^{-1}$; $^1$H NMR (500 MHz, CDCl$_3$): δ 7.67 (d, J=8.0 Hz, 2H), 7.30 (d, J=8.0 Hz, 2H), 6.89-6.87 (m, 1H), 3.73 (dd, J=4.5, 2.4 Hz, 2H), 3.14 (t, J=5.7 Hz, 2H), 2.48-2.44 (m, 2H), 2.40 (s, 3H), 2.25 (s, 3H); $^{13}$C NMR (125 MHz, CDCl$_3$): δ 196.6, 143.6, 137.9, 136.0, 132.9, 129.6, 127.6, 43.4, 41.7, 26.0, 24.9, 21.4; HRMS (m/z): [M+H]$^+$ calcd. for C$_{14}$H$_{17}$NO$_3$SH, 280.1002. found, 280.1000.

Example 4
Identification of Aplexone from a Library of Heterocycles Derived from Nucleophilic Phosphine Catalysis of Allenes and its Structure-Activity Relationship (SAR) Studies A. Introduction Screening an unbiased library of compounds for the chance of identifying small organic molecules with desired biological activity has been thoroughly established as one of the main activities of chemical biology.[1] While there exist many commercial libraries of small organic molecules,[4] de novo synthesis also provides a means to prepare new and novel compounds for biological screening.[2,3] Due to the random nature of the chemical screening, the thought was that it would be advantageous to test a large number of compounds. Combinatorial chemistry in its broadly defined sense has been exercised for the purpose of generating collections of small organic molecules.[3,4] In the not so long history of combinatorial synthesis conjoined with subsequent biological screening, however, it has been recognized that the diversity in the structures of compounds is as important as (if not more than) the number of (structurally related) molecules.[5-8] It was in this vein that the idea of developing a series of related reactions that are amenable to combinatorial synthesis (even on solid phase in a split-and-pool format) while generating structurally distinct collection of compounds was conceived.

Nucleophilic phosphine catalysis of allenes provided the potential to satisfy such a demand, especially with the exponential increase in the number of new reactions reported during the past decade or so. Our laboratory alone reported phosphine-catalyzed reactions of allenes with imines, alkenes, aldehydes, aziridines, and maleimides to produce tetrahydropyridines,[9,10] cyclohexenes,[11] dioxanes,[12] pyrones,[13] dihydropyrones,[14] pyrrolines,[15] bicyclic succinimides,[16] dihydrocoumarins, and cyclic nitronates (Scheme 1).[17] Some of these reactions have been indeed applied to the solid phase split-and-pool synthesis using resin-bound allenoates.[18] While the immediate products from the phosphine-catalyzed annulation reactions of allenes were screened and produced novel biological modulators,[18-20] the common functional group, such as the α,β-unsaturated carbonyl functionality in the allenoate-derived heterocycles provided an addition handle for further structural modification. One such pathway was the conversion of the α,β-unsaturated ester to alkoxydiene through Tebbe reaction. For instance, tetrahydropyridine carboxylic ester 1, derived from the phosphine-catalyzed Scheme 1. Nucleophilic Phosphine Catalyses of Allenoates.

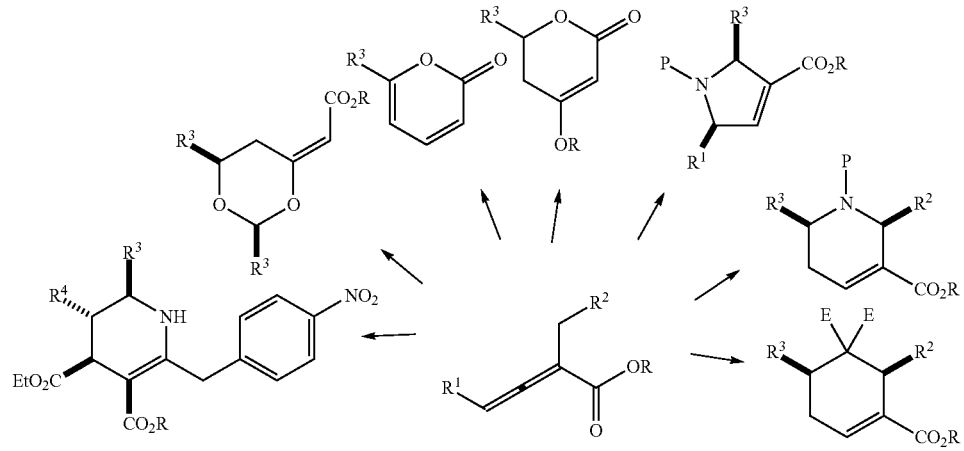

-continued

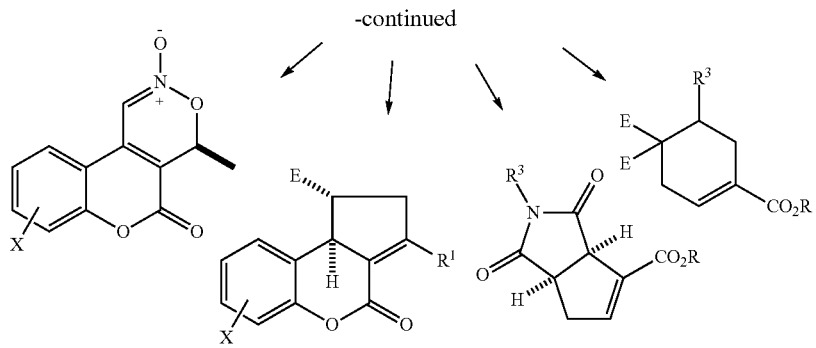

[4+2] annulation between α-methyl allenoate and N-sulfonyl imine, was treated with the in situ generated Tebbe's reagent[21] and converted into dienol ether 2 (Scheme 2). The resulting dienes render a handle for regular electron demand Diels-Alder reaction with a variety of electron deficient dienophiles.[22] The product dienol ether can also be simply hydrolyzed and produce an enone. It was one such enone compound, aplexone, that was discovered to selectively disrupt venous angiogenesis in zebrafish embryos.

Synthesis aimed at generation of a collection of molecules with drastic structural variations are claimed to be undertaken based on the premise that a diverse range of scaffolds should provide a higher chance for discovery of small-molecule biological functional modulators. However, more often than not the synthesis is reported without the subsequent biological testing and it is even rarer to see the follow-up medicinal chemistry efforts to dissect the structure-activity relationship (SAR) of the initial hit molecule(s). Herein, we report a Scheme 2 Synthesis of Aplexone.

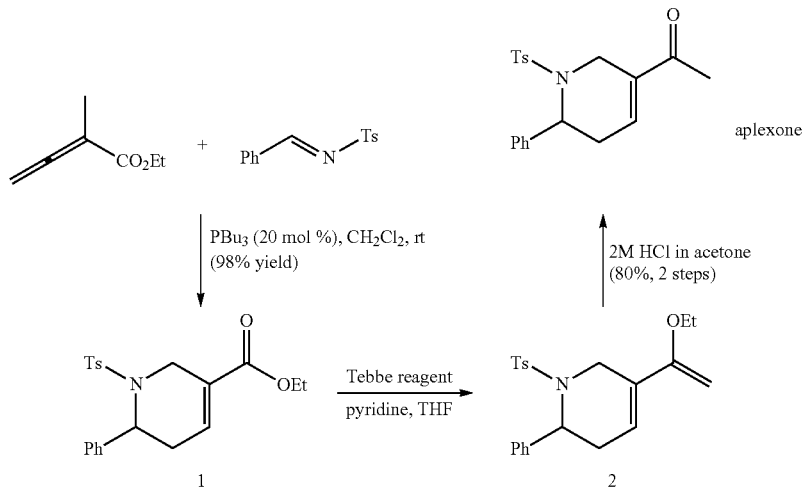

The use of zebrafish embryo as a model organism for in vivo chemical screens is becoming increasingly popular due to the following advantages:[23] 1] The zebrafish produce a large number of small progeny rapidly developing in an extra-uterus manner. These factors allow easy application of the compounds for high throughput screening in 96-well plates. 2] The transparent nature of zebrafish embryos greatly assists morphological and functional analyses in live embryos. And, 3] accumulating evidence indicates that molecular and cellular mechanisms critical for fundamental biological processes are conserved from fish to mammals. Therefore, information obtained from the zebrafish system can be applied to other model organisms and even humans. In addition, unlike genetic modification chemical compounds can provide an easy temporal and dose control at desired developmental stages to interrogate the molecular mechanisms of biological phenomenon of interest.

discovery of aplexone from a library of compounds generated from the phosphine-catalyzed annulation of allenoates and its SAR studies.

SAR elements are shown in FIG. 12. Aplexone is used for illustration purposes only. The phenyl ring (1), sulfonyl group (2) and carbonyl group (3) are important for biological activity. The substituent (4) attached to the carbonyl carbon (2) may vary. The endocyclic bond (5) may be a single or double bond, but the configurational integrity the double bond maintains improves activity. The C4 carbon (6) should remain unsubstituted. The C6 phenyl (7) may be absent, or may be replaced with other substituents, and bulky substituents at the para position of the C6 phenyl may decrease activity. Substituents (8) on phenyl ring (1) may vary and be at the ortho, meta, or para positions.

B. Screening

The library of 168 compounds[24] prepared through the nucleophilic phosphine catalysis of allenes were screened using Tg(kdrl:GFP) zebrafish. Four embryos were placed in each well of 96-well plates containing a 10 uM solution of each chemical compound dissolved in embryo buffer with 0.1% DMSO. The embryos were raised at 28.5° C. and defects in blood vessel development were examined at 1 and 2 days after fertilization.

C. Biology

By doing the transcription profiling, it was found out that aplexone targets the HMG-CoA reductase pathway. Injecting mevalonate, a metabolic product of HMGCR, reverses the inhibitory effect of aplexone on venous angiogenesis.

methyl group to produce piperidine 5.[27] The anti-angiogenetic activity testing showed that the trans isomer 3 is as potent as aplexone in its inhibitory actions against the CVP formation while the cis isomer 4 and 5 were inactive. These observations indicate that 1] the enone functional group is not required for the aplexone's effect, suggesting that aplexone is not a covalent modifier of its target vis Michael addition and 2] the three-dimensional shape of aplexone, particularly the didehydropiperidine heterocycle, is important for its van der Waals interactions with its cellular target protein. Structure confirmation, including NMR data, for aplexone analogs shown in FIG. 11 are presented in Example 6 below.

Scheme 3. Synthesis of Acetylpiperidines 3, 4 and 5.

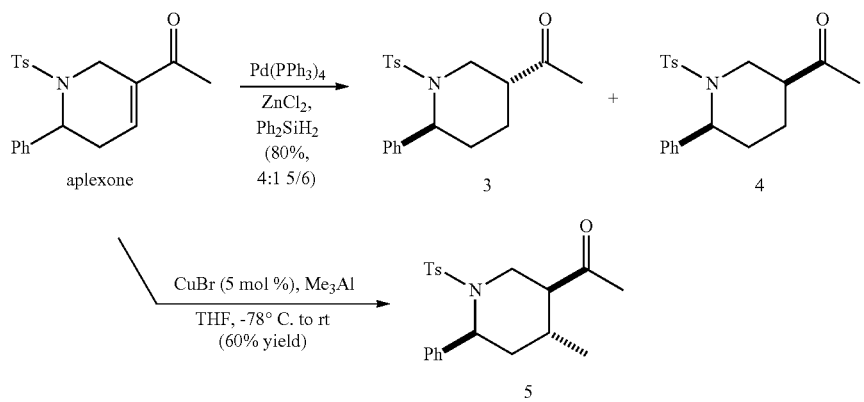

Figure 1:
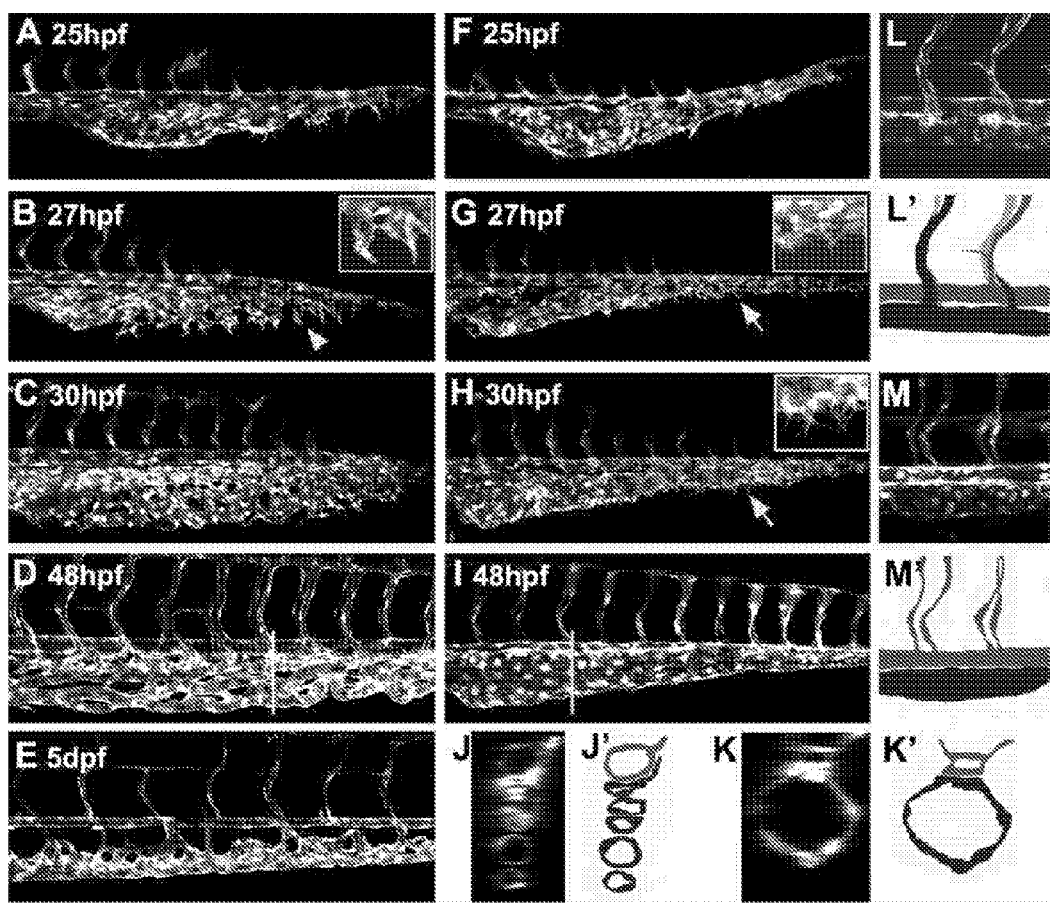
FIG. 1 shows the development of the zebrafish caudal vein plexus. A-I, Confocal images of caudal vasculature at different developmental stages, A-E, untreated control Tg(kdrl:GFP) embryos. F-I, Tg(kdrl:GFP) embryos treated with 10 µM aplexone beginning at 10 hpf. The arrow in (A) indicates a primary ISV. The arrowhead in (B) indicates venous angiogenic sprouts. Arrows in (G, H) indicate filopodia that fail to mature into angiogenic sprouts. Insets in (B, G, H) are magnified images of the areas indicated by the yellow arrowhead and arrows. Bars in (B) and (E) indicate the distance between the axial artery and vein. J and K, Optical cross sections of blood vessels in control (J) and aplexone treated (K) embryos at 48 hpf. Bars in (D, I) indicate the position where the cross sections were extracted. J' and K', Schematic drawings of the cross sections in control (J') and aplexone treated (K') embryos. Grey represents the dorsal aorta and black the caudal vein. L and M, Confocal images of blood vessels in the trunk of control (L) and aplexone-treated (M) Tg(kdrl:GFP) embryos. Images were taken at 48 hpf. L' and M', Schematic drawings of L and M. Grey and black represent the artery and vein, respectively. Horizontal vessels are the dorsal aorta and posterior cardinal vein. Vertical vessels are intersegmental vessels.
Figure 2:
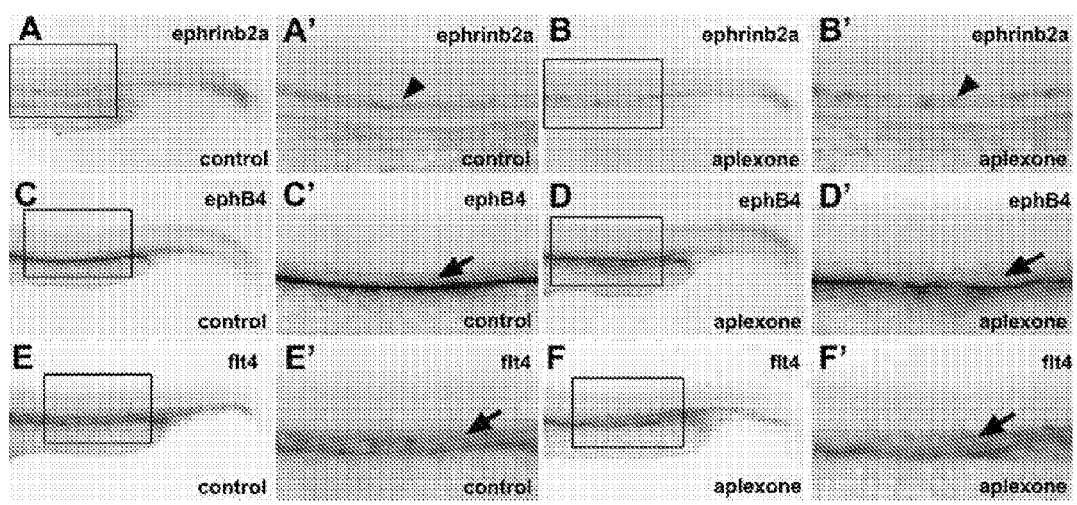
FIG. 2 shows that aplexone does not affect arterial and venous fate. Untreated control embryos (A, C, E and A', C', E') and embryos treated with 10 µM aplexone beginning at 10 hpf (B, D, F and B', D', F') were fixed at 24 hpf. Arterial and venous fates were analyzed by in situ hybridization using ephrinB2a (A,A',B,B'), ephB4 (C,C',D,D') and flt4 (E,E',F,F') probes. Arrowhead, dorsal aorta. Embryos were analyzed at higher magnification in the trunk in A'-F', with regions of interest indicated by black boxes in A-F. Arrow, posterior cardinal vein.

Stains are widley used drugs that are well established to target HMG-CoA reductase, rendering its as its ultimate effect as lowering the blood cholesterol level in humans. The effect of aplexone on the level of cholesterol was tested and it was found that aplexone reduces cellular cholesterol levels (FIG. 1). It was noticeable that aplexone was as efficient as atorvastatin at lower concentration (10 uL), but more efficient at higher concentration (40 uL).

Aplexone disrupts protein geranylation. Blocking the activity of geranygeranyltransferase induces a venous angiogenesis phenotype resembling that observed in aplexone treated embryos, which indicated that protein geranylgeranylation is important in angiogenesis. Furthermore, Aplexone effectively inhibits venous EC migration both in zebrafish embryos and cultured human ECs. This was found due to the fact that venous ECs have higher levels of proteins requiring geranylgeranylation than arterial ECs and their migration is more sensitive to changes in protein prenylation.

D. Syntheses of Aplexone Analogs and their Aplexone-Like Activities

Next, we synthesized aplexone analogs to determine the structural features required for aplexone to suppress venous angiogenesis. Aside from the didehydropiperidine structure, one of the key structural elements of aplexone is the enone functional group. Enone is a great Michael acceptor and aplexone could potentially function as a covalent modulator of its target protein through the Michael addition of thiol and amine groups. To test whether aplexone functions as a Michael acceptor under the cell physiological conditions, the enone double bond was hydrogenated under the influence of palladium tetrakistriphenylphosphine, diphenylsilane, and zinc(II) chloride,[25] which produced two diastereoisomeric ketones 3 and 4 in 80% yield (Scheme 3).[26] The α,β-unsaturation was also obliterated by the Michael addition of a We further probed the importance of the acetyl substituent in aplexone by reducing the ketone functionality. When treated with diisobutylaluminum hydride (DIBAL), aplexone produced two diastereoisomeric alcohols 5 and 6 in 90% efficiency (Scheme 4). Both alcohols did not inhibit the CVP formation, indicating that the ketone functional group is required for aplexone's biological activity. The relative configuration of the newly formed alcohols were not determined, especially since both of the alcohols were inactive. This observation hinted the possibility of another covalent modification of the target protein via Schiff base formation. To verify (or exclude) this possibility we tested the ethyl ester 1, which retained the bioactivity of aplexone. Again, these observations indicated that the acetyl carbonyl group is highly important (and possibly essential) for noncovalent interactions of aplexone with its cellular target rather then covalent modification of it.

Scheme 4. Synthesis of Alcohols 6 and 7.

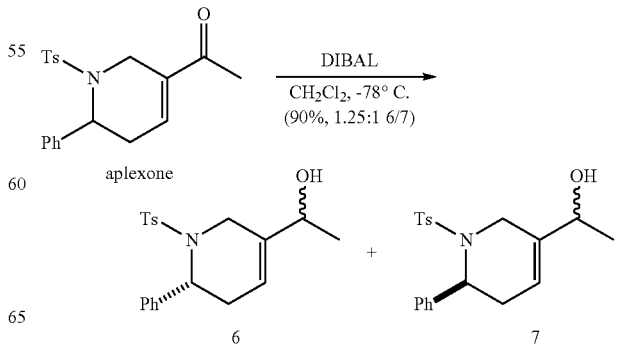

We further examined the importance of the acetyl substituent by introducing an additional substituent at the α'-carbon (compound 8) of the acetyl group. Aplexone was treated with lithium diisopropylamide (LDA) followed by allyl bromide to provide enone 8 (Scheme 5). The α'-allyl substituted aplexone analog 8 showed the bioactivity of aplexone albeit to a lesser extent. The retained, albeit mild, activity of the analog 8 was encouraging since the terminal olefin group (via olefin metathesis) can provide a handle for affinity and fluorescent labeling for the future studies.

Scheme 5. α'-Allylation of Aplexone.

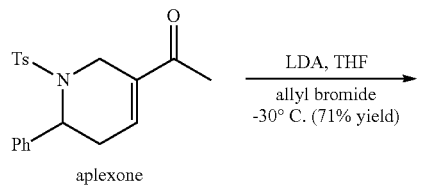

aplexone p-toluenesulfonyl (tosyl) protecting group on the didehydropiperidine ring nitrogen. Since the dissolving metal reduction conditions were not compatible with the enone functionality of aplexone, the ketone was first protected with ethylene glycol under p-toluenesulfonic acid catalysis (Scheme 6). Treatment of compound 9 with sodium naphthalide smoothly removed the tosyl group. Subsequent deprotection of the dioxolane in 10 produced the desired N-detosylated aplexone analog 11. To test the functional requirement of the sulfonyl group, the free amine in 11 was protected with the benzyl group (compounds 12). For the requirement of the benzene ring in the N-tosyl group, N-methanesulfonyl (N-mesyl) analog of aplexone 13 was prepared through the phosphine-catalyzed [4+2] annulation of α-methyl allenoate and N-mesyl (N-Ms) benzealdimine, Tebbe reaction, and hydrolysis (see Scheme 2). The treatment of an analog without the tosyl group (compound 11), as well as the N-benzyl (compound 12) and N-mesyl (compound 13) analogs, failed to inhibit the formation of CVP, indicating that both the sulfonyl functionality and the phenyl ring of the tosyl group are highly important (and possibly critical) for the inhibitory activity of aplexone on venous angiogenesis.

Scheme 6. Modification of the N-Tosyl Group of Aplexone.

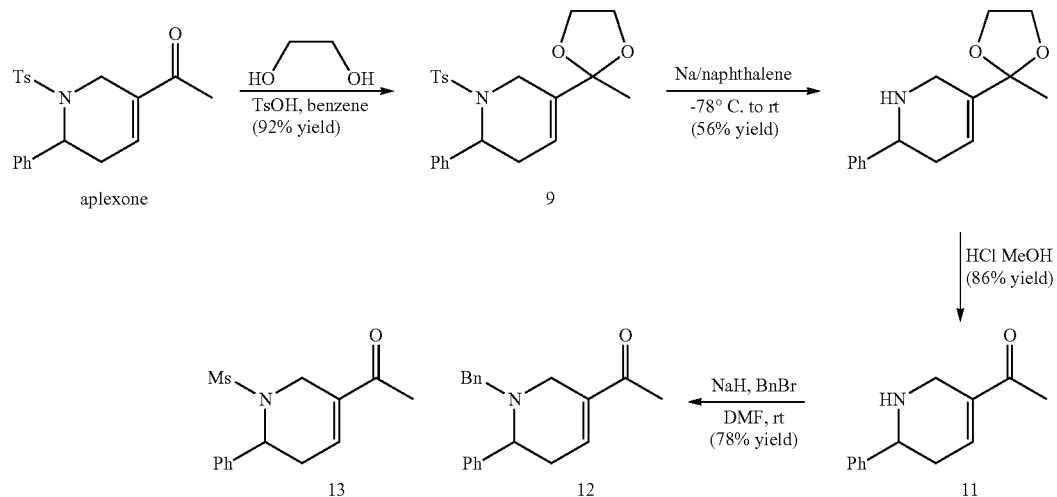

-continued

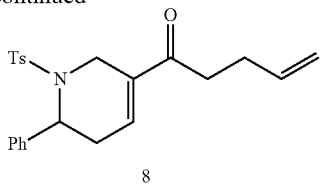

8

Having triaged the possibility of covalent modification of the cellular target by aplexone, the attention was shifted into structural requirement of aplexone's vein-specific anti-angiogenetic activity. First, we evaluated the requirement of the We then investigated whether the phenyl group at the C6 position of the didehydropiperidine ring is required for aplexone activity. Since the phosphine-catalyzed [4+2] annuation does not work for N-sulfonylimines derived from formaldehyde, aplexone analog 16 without the C6 phenyl group needed to be synthesized via alternative route (Scheme 7). Since the known procedure to synthesize 16 was highly inefficient,[28] we devised an alternative route for its preparation. First, the nitrogen of ethyl 4-piperidinone-3-carboxylate was protected with tosyl group and the ketone was reduced using sodium borohydride to provide a mixture of diastereoisomeric alcohols 14 (54% yield, two steps). The resulting alcohol was then mesylated and eliminated to provide enoate 15 (70% yield, two steps). The ethoxycarbonyl group was transformed into the acetyl group in 16 through the Tebbe/hydrolysis processes in 80% yield. Embryos treated with compound 16, an analog lacking the phenyl group, developed a single-lumen caudal vein like aplexone, albeit in lower efficiency, demonstrating that unlike the phenyl ring of the tosyl group, the C6-phenyl group of the didehydropiperidine ring is dispensable.

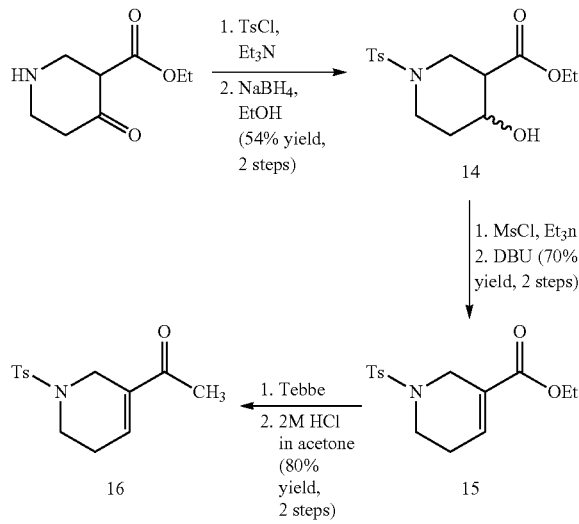

Scheme 7. Preparation of an Aplexone Analog 16 without C6-Phenyl.

⑦ indicates text missing or illegible when filed

To gain more insights into aplexone's structure activity relationship and potentially identify even more potent analogs, we prepared analogs with variations in the structures of the two aryl groups on the didehydropiperidine ring and the sulfonamide. The identifications of permissible modifications on the aplexone structure can also provide handles for derivatization that would be necessary for the future chemical biological studies. Each analog was prepared through the phosphine-catalyzed [4+2] annulation of ethyl α-methyl allenoate and N-sulfonyl arylimines, Tebbe reaction, and hydrolysis and the yield for the Tebbe/hydrolysis is provided under each compound (FIG. 11). Each of the structures has been confirmed by NMR analysis.

Analogs 17-20 with variations in the substituents of the phenyl ring of the sulfonamide group showed inhibitory activity for venous angiogenesis. The p-methyl group could be removed (compound 17) or changed to chloride substituent (compound 20). The methyl group could also be placed in the ortho (compound 18) or meta (compound 19) positions without showing much decrease in the activity. On the other hand, substituents on the didehydropiperidine ring-pheny group showed more dramatic effect to its antiangiogenetic activity. Aplexone analogs with an additional substituent at ortho- and meta-positions of the C2-phenyl group (compounds 21-23) retained the anti-angiogenetic activity while the introduction of para-fluoro groups (compounds 24) abolished the biological activity and para-chloro group (compound 25) diminished the antiangiogenic activity of the otherwise identical analogs. Intrigued by this observation, we further prepared aplexone analogs with C6-phenyl ring substituted with para-methyl, isopropyl, methoxy, ethoxy, and bromo groups. The general observation was that p-methylphenyl substituted didehydropiperidine (compound 26) was active while p-isopropyl, p-bromo, p-methoxy and p-ethoxy- groups (compounds 27-30) were detrimental to the biological activity. Not surprisingly, 3,4-disubstituted phenyl containing aplexone analogs (compounds 31 and 32) were not active. One could conclude that a bulky substituent at the para-position of the didehydropiperidine ring-phenyl group hinders the small molecule-protein interaction. C2-heteroaryl and naphthyl substituted didehydropiperidines were prepared. Among them, 2-thiophenyl substituted aplexone analog (compound 33) was active while 2-furyl (34 and 35), 2-pyrrolyl (36), and 1-naphthyl (37) derivatives were inactive. The survey of the extensive variation in the substituents in both aryl groups on the didehydropiperidine ring and the sulfonamides unveiled the delicate balance between the anti-angiogenetic activity of aplexone and slight changes in its structure and provided information on the indispensable elements and flexible portions of aplexone molecular architecture. This information can be used in the future as the basis for preparing additional functional variants of aplexone.

Conclusions

The diversity library generated from the nucleophilic phosphine catalysis of allenoates, when screened in a developmental assay using zebrafish embryos, allowed identification of aplexone, an antagonist for venous angiogenesis. Using this DOS approach, we efficiently achieved sufficiently high levels of skeletal diversity to explore biologically relevant regions of chemical space. Indeed, our current library, despite its small number of components, allowed the identification of compounds that inhibit angiogenesis specifically for veins. It is expected that these compounds will also exhibit the other properties of aplexone, such as the ability to inhibit HMGCR synthesis and to lower cellular cholesterol levels when contacted with a suitable cell or administered to a suitable subject.

Overall, the studies based on 33 aplexone analogs indicated the following structural requirement for its anti-anigiogenetic activity: 1] The configurational integrity that the tetrahydropyridine ring provides is highly important (and possibly essential) for the activity of aplexone. 2] It is unlikely that aplexone modulates its target protein via covalent modification. 3] The carbonyl of the C3 acetyl group, the N-sulfonyl group, and the phenyl ring of the N-tosyl group of aplexone are required while the C6-phenyl group is not essential for aplexone's activity. 4] While various substituents on the benzene ring of the N-benzenesulfonyl group are tolerated, bulky substituents on the C6-phenyl ring, especially at the para-position, are pernicious to the aplexone's activity. C6-heteroaryl rings, especially sterically demanding ones are detrimental to the aplexone's effect too.

References

Electronic Supplementary Information (ESI) available: The experimental procedures and physical/spectroscopic characterization of aplexone and its analogs. See DOI: 10.1039/b000000x/

1 S. L. Schreiber, T. M. Kapoor and G. Wess, *Chemical Biology: From Small Molecules to Systems Biology and Drug Design*, Wiley-VCH Verlag GmbH & Co. KGaA, Weinheim, 2008.

2 D. P. Walsh and Y.-T. Chang, *Chem. Rev.* 2006, 106, 2476.

3 R. E. Dolle, B. L. Bourdonnec, A. J. Goodman, G. A. Moorales, C. J. Thomas and W. Zhang, *J, Comb. Chem.*, 2009, 11, 739.

4 N. K. Terret, Combinatorial Chemistry, Oxford Univ Press, Oxford, UK, 1998.

5 M. D. Burke and S. L. Schreiber, *Angew. Chem. Int. Ed.*, 2004, 43, 46.

6 T. E. Nilsen and Schreiber, *Angew. Chem. Int. Ed.*, 2008, 47, 48.

7 R. J. Spandl, A. Bender and D. R. Spring, *Org. Biomol. Chem.*, 2008, 6, 1149.
8 W. R. J. D. Galloway, A. Isidro-Llobet and D. R. Spring, *Nat. Common.*, 2010, 1, 80.
9 X.-F. Zhu, J. Lan and O. Kwon, *J. Am. Chem. Soc.*, 2003, 125, 4716.
10 H. Guo, Q. Xu and O. Kwon, *J. Am. Chem. Soc.*, 2009, 131, 6318.
11 Y. S. Tran and O. Kwon, *J. Am. Chem. Soc.* 2007, 129, 12632.
12 X.-F. Zhu, C. E. Henry J. Wang, T. Dudding and O. Kwon, *Org. Lett.*, 2005, 7, 1387.
13 X.-F. Zhu, A. Schaffner, R. C. Li and O. Kwon, *Org. Lett.*, 2005, 7, 2977.
14 G. S. Creech and O. Kwon, *Org. Lett.*, 2008, 10, 429.
15 X.-F. Zhu, C. E. Henry and O. Kwon, *Tetrahedron*, 2005, 61, 6276.
16 Unpublished results???
17 C. E. Henry and O. Kwon, *Org. Lett.*, 2007, 9, 3069.
18 S. Castellano, H. D. G. Fiji, S. S. Kinderman, M. Watanabe, M.; P. De Leon, F. Tamanoi and O. Kwon, *J. Am. Chem. Soc.*, 2007, 129, 5843.
19 J. Lu, L. Chan, H. D. G. Fiji, R. Dahl, O. Kwon and F. Tamanoi, *Mol. Cancer Ther.*, 2009, 8, 1218.
20 M. Watanabe, H. D. G. Fiji, L. Guo, L. Chan, S. S. Kinderman, D. J. Slamon, O. Kwon and F. Tamanoi, *J. Biol. Chem.*, 2008, 283, 9571.
21 L. F. Cannizzo and R. H. Grubbs, *J. Org. Chem.*, 1985, 50, 2386.
22 Z. Wang, S. Castellano, S. S. Kinderman, C. E. Argueta, A. B. Beshir, G. Fenteany and O. Kwon, *Chem.—Eur. J.*, 2011, 17, 649.
23 C. A. MacRae and R. T. Peterson, *Chem. Biol.*, 2003, 10, 901.
24 The chemical structures of the synthetic chemical library of 168 compounds are provided in ESI, Figure S1.
25 E. Keinan and N. Greenspoon, *J. Am. Chem. Soc*, 1989, 108, 7314.
26 The relative stereochemistry of the cis- and tran-isomers was assigned based on the coupling patterns of the piperidine ring protons in the $^1$H NMR spectra. The identities of the ring protons were assigned based on the chemical shifts of the protons and by COSY NMR experiment. According to the literature, the C6 phenyl group adopts an axial position in the favored chair conformations of the cis- and trans-isomers; D. Craig, J. D. Meadows, and M. Pécheux, *Tetrahedron Lett.*, 1998, 39, 147-150; C. A. M. Cariou and J. S. Snaith, *Org. Biomol. Chem.*, 2006, 4, 51.
27 The relative stereochemistry of 5 was assigned by the analogy to that of 4 and based on the coupling constants in the NMR spectrum. The identities of the ring protons were assigned based on the chemical shifts of the protons and by the COSY NMR experiment.
28 The synthetic scheme and the overall yield (4%) of the alternative route to compound 16 is shown in the ESI. For reference, see: M. Banziger, S. Klein and G. Rihs, *Helv. Chim. Acta*, 2002, 85, 1399.
29 Westerfield, M. *The zebrafish book*, (The University of Oregon Press, 2000).

Example 5

Confirmation of Activity of Aplexones of the Invention in Mammals

An aplexone of the invention is introduced (administered) into a suitable animal model for cancer or other angiogenesis-mediated condition of disease, or for a condition or disease in which the model would benefit from a reduction in cholesterol levels. Suitable models will be evident to a skilled worker, and include, e.g., for the study of cancer, nude mice into which an exogenous tumor has been introduced. Methods for carrying out tests for efficacy and suitable controls will be evident to a skilled worker. It is expected that aplexones of the invention (as represented by Formulas I, II, III and the structures shown in FIG. 11, as well as pharmaceutically salts and hydrates thereof, and pharmaceutical compositions comprising those compounds, will reduce angiogenesis (e.g., result in inhibition of tumor growth) and/or will result in a lowering of cholesterol levels in the tested animal models. The most active compounds in the angiogenesis test are Compounds 17-23, 26, and 33, shown in FIG. 11.

Example 6

NMR Analysis of the Structures Shown in Table 11

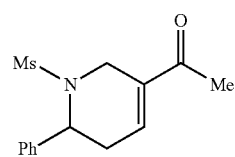

13

White solid, 50% yield, two steps; IR (film) $v_{max}$ 3027, 2929, 1666, 1151 cm$^{-1}$; $^1$H NMR (500 MHz, CDCl$_3$): δ 7.39-7.31 (m, 5H), 7.20-7.18 (m, 1H), 5.38 (d, J=7.3 Hz, 1H), 4.45 (d, J=17.8 Hz, 1H), 3.51-3.46 (m, 1H), 3.12-3.05 (m, 1H), 2.85-2.80 (m, 1H), 2.72 (s, 3H), 2.39 (s, 3H); $^{13}$C NMR (125 MHz, CDCl$_3$); δ 196.4, 138.0, 137.3, 136.0, 128.8, 128.2, 127.1, 52.4, 38.7, 38.6, 29.4, 25.0; HRMS (m/z): [M+Na]$^+$ calcd, for C$_{14}$H$_{17}$NO$_3$SNa, 302.0821. found, 302.0807.

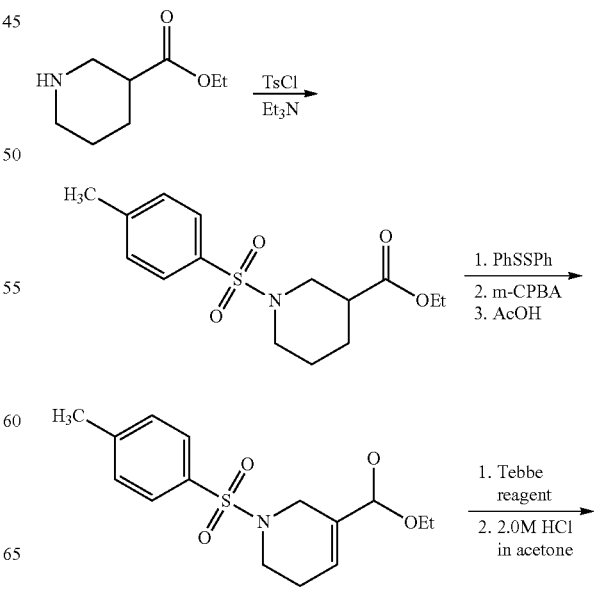

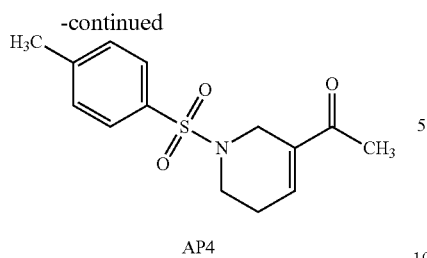

AP4

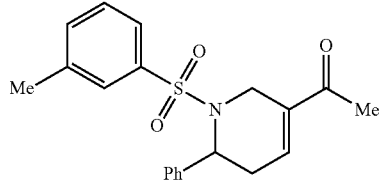

19

16 was synthesized following the known procedure.[1] Colorless oil, 4% overall yield, 6 steps; IR (film) $v_{max}$ 3063, 2925, 1668, 1165 cm$^{-1}$; $^1$H NMR (500 MHz, CDCl$_3$): δ 7.67 (d, J=8.0 Hz, 2H), 7.30 (d, J=8.0 Hz, 2H), 6.89-6.87 (m, 1H), 3.73 (dd, J=4.5, 2.4 Hz, 2H), 3.14 (t, J=5.7 Hz, 2H), 2.48-2.44 (m, 2H), 2.40 (s, 3H), 2.25 (s, 3H); $^{13}$C NMR (125 MHz, CDCl$_3$): δ 196.6, 143.6, 137.9, 136.0, 132.9, 129.6, 127.6, 43.4, 41.7, 26.0, 24.9, 21.4; HRMS (m/z): [M+H]$^+$ calcd. for C$_{14}$H$_{17}$NO$_3$SH, 280.1002. found, 280.1000.

[1] M. Banziger, S. Klein and G. Rihs, Helv. Chim. Acta, 2002, 85, 1399

Colorless oil, 72% yield, two steps; IR (film) $v_{max}$ 3062, 2923, 1667, 1155 cm$^{-1}$; $^1$H NMR (500 MHz, CDCl$_3$): δ 7.55-7.52 (m, 2H), 7.29-7.26 (m, 2H), 7.22-7.16 (m, 5H), 6.90 (t, J=1.7 Hz, 1H), 5.36 (d, J=5.4 Hz, 1H), 4.48 (d, J=18.5 Hz, 1H), 3.38 (ddd, J=18.5, 5.5, 3.3 Hz, 1H), 2.71-2.65 (m, 2H), 2.31 (s, 3H), 2.20 (s, 3H); $^{13}$C NMR (125 MHz, CDCl$_3$): δ 196.5, 139.8, 139.1, 138.2, 137.2, 136.0, 133.3, 128.8, 128.5, 127.7, 127.2, 127.0, 124.0, 52.2, 38.9, 27.6, 24.9, 21.2; HRMS (m/z): [M+Na]$^+$ calcd. for C$_{20}$H$_{21}$NO$_3$SNa, 378.1134. found, 378.1129.

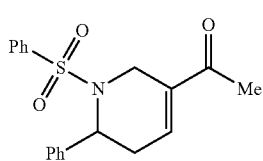

17

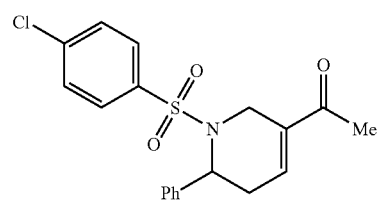

20

White solid, 76% yield, two steps; IR (film) $v_{max}$ 3059, 2913, 1666, 1162 cm$^{-1}$; $^1$H NMR (400 MHz, CDCl$_3$): δ 7.78-7.75 (m, 2H), 7.54-7.50 (m, 1H), 7.45-7.40 (m, 2H), 7.25-7.16 (m, 5H), 6.92-6.90 (m, 1H), 5.40 (dd, J=5.5, 1.9 Hz, 1H), 4.49 (d, J=18.5 Hz, 1H), 3.40 (ddd, J=18.5, 5.9, 3.6 Hz, 1H), 2.70-2.67 (m, 2H), 2.22 (s, 3H); $^{13}$C NMR (100 MHz, CDCl$_3$): δ 196.5, 140.1, 138.2, 137.1, 136.2, 132.6, 129.0, 128.6, 127.9, 127.1, 127.0, 52.3, 39.0, 27.8, 25.0; HRMS (m/z): [M+Na]$^+$ calcd. for C$_{19}$F$_{19}$NO$_3$SNa, 364.0978. found, 364.0970.

White solid, 75% yield, two steps; IR (film) $v_{max}$ 3060, 2895, 1667, 1163 cm$^{-1}$; $^1$H NMR (500 MHz, CDCl$_3$): δ 7.67 (d, J=8.6 Hz, 2H), 7.37 (d, J=8.6 Hz, 2H), 7.24-7.22 (m, 3H), 7.17-7.15 (m, 2H), 6.93-6.92 (m, 1H), 5.37 (d, J=5.1 Hz, 1H), 4.45 (d, J=18.4 Hz, 1H), 3.39 (ddd, J=18.4, 5.6, 3.2 Hz, 1H), 2.70-2.68 (m, 2H), 2.22 (s, 3H); $^{13}$C NMR (125 MHz, CDCl$_3$): δ 196.4, 138.9, 138.5, 137.9, 137.0, 135.9, 129.2, 128.6, 128.4, 127.9, 126.9, 52.3, 39.0, 27.9, 24.9; HRMS (m/z): [M+H]$^+$ calcd. for C$_{19}$H$_{18}$ClNO$_3$SH, 376.0769. found, 376.0771.

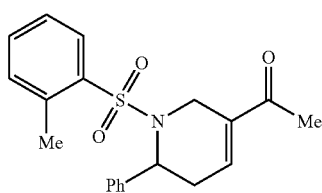

18

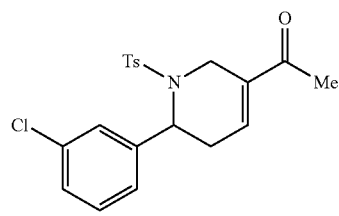

21

Yellow oil, 70% yield, two steps; IR (film) $v_{max}$ 3062, 2929, 1667, 1159 cm$^{-1}$; $^1$H NMR (400 MHz, CDCl$_3$): δ 7.96 (d, J=8.2 Hz, 1H), 7.43 (td, J=7.5, 1.3 Hz, 1H), 7.29-7.18 (m, 5H), 7.11-7.08 (m, 3H), 5.17 (d, J=6.6 Hz, 1H), 4.43 (dd, J=18.3, 0.9 Hz, 1H), 3.41-3.34 (m, 1H), 2.95-2.86 (m, 1H), 2.79-2.72 (m, 1H), 2.52 (s, 3H), 2.25 (s, 3H); $^{13}$C NMR (100 MHz, CDCl$_3$): δ 196.6, 138.0, 137.8, 137.7, 137.6, 136.5, 133.0, 132.8, 130.1, 128.6, 128.0, 127.1, 126.2, 51.9, 38.6, 28.0, 25.0, 20.3; HRMS (m/z): [M+Na]$^+$ calcd. for C$_{20}$H$_{21}$NO$_3$SNa, 378.1134. found, 378.1129.

White solid, 75% yield, two steps; IR (film) $v_{max}$ 3060, 2914, 1668, 1160 cm$^{-1}$; $^1$H NMR (500 MHz, CDCl$_3$): δ 7.63 (d, J=8.2 Hz, 2H), 7.22 (d, J=8.2 Hz, 2H), 7.18-7.17 (m, 2H), 7.09-7.07 (m, 2H), 6.89-6.88 (m, 1H), 5.32 (t, J=3.8 Hz, 1H), 4.48 (d, J=18.6 Hz, 1H), 3.38 (ddd, J=18.6, 5.6, 3.3 Hz, 1H), 2.65-2.64 (m, 2H), 2.38 (s, 3H), 2.21 (s, 3H); $^{13}$C NMR (125 MHz, CDCl$_3$): δ 196.4, 143.6, 140.2, 136.8, 136.5, 136.1, 134.4, 130.0, 129.6, 127.9, 127.2, 126.9, 125.1, 51.7, 38.9, 27.4, 24.9, 21.4; HRMS (m/z): [M+H]$^+$ calcd. for C$_{20}$H$_{20}$ClNO$_3$SH, 390.0925. found, 390.0927,

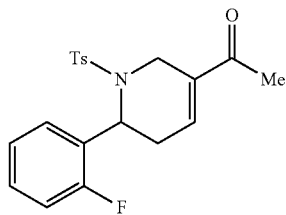

22

Yellow solid, 69% yield, two steps; IR (film) $v_{max}$ 3064, 2917, 1667, 1162 cm$^{-1}$; $^1$H NMR (400 MHz, CDCl$_3$): δ 7.64 (d, J=8.3 Hz, 2H), 7.24-7.17 (m, 3H), 7.02-6.92 (m, 4H), 5.72 (d, J=7.2 Hz, 1H), 4.42 (d, J=18.3 Hz, 1H), 3.59-3.52 (m, 1H), 2.93-2.84 (m, 1H), 2.64-2.57 (m, 1H), 2.37 (s, 3H), 2.26 (s, 3H); $^{13}$C NMR (100 MHz, CDCl$_3$): δ 196.5, 161.4, 158.9, 143.4, 137.2, 136.5, 136.3, 129.4, 127.8, 127.3, 126.7, 126.6, 124.0, 116.0, 115.8, 46.7, 39.4, 29.3, 25.0, 21.5; HRMS (m/z): [M+Na]$^+$ calcd. for C$_{20}$H$_{20}$FNO$_3$SNa, 396.1040. found, 396.1031.

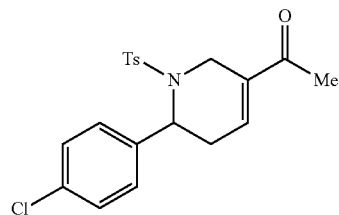

25

Yellow oil, 65% yield, two steps; IR (film) $v_{max}$ 3060, 2925, 1666, 1160 cm$^{-1}$; $^1$H NMR (400 MHz, CDCl$_3$): δ 7.63 (d, J=8.3 Hz, 2H), 7.23-7.20 (m, 4H), 7.13 (d, J=8.3 Hz, 2H), 6.89-6.87 (m, 1H), 5.34 (t, J=3.9 Hz, 1H), 4.45 (d, J=18.6 Hz, 1H), 3.36 (ddd, J=18.6, 5.6, 3.3 Hz, 1H), 2.67-2.64 (m, 2H), 2.39 (s, 3H), 2.21 (s, 3H); $^{13}$C NMR (100 MHz, CDCl$_3$): δ 196.4, 143.6, 137.0, 136.8, 136.6, 136.3, 133.7, 129.7, 128.8, 128.5, 127.0, 51.6, 39.0, 27.6, 25.0, 21.5; HRMS (m/z): [M+H]$^+$ calcd. for C$_{20}$H$_{20}$ClNO$_3$SH, 390.0925. found, 390.0911.

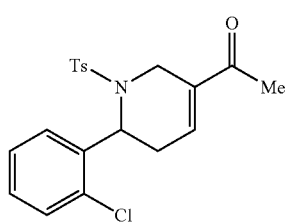

23

White solid, 70% yield, two steps; IR (film) $v_{max}$ 3060, 2917, 1668, 1163 cm$^{-1}$; $^1$H NMR (400 MHz, CDCl$_3$): δ 7.59 (d, J=8.2 Hz, 2H), 7.31 (dd, J=8.0, 1.0 Hz, 1H), 7.15-7.11 (m, 3H), 7.00 (td, J=7.6, 0.7 Hz, 1H), 6.93 (dd, J=7.8, 1.5 Hz, 1H), 6.89-6.88 (m, 1H), 5.72 (dd, J=7.2, 1.4 Hz, 1H), 4.36 (d, J=18.2 Hz, 1H), 3.67 (dd, J=18.2, 2.4 Hz, 1H), 2.91-2.83 (m, 1H), 2.58-2.52 (m, 1H), 2.33 (s, 3H), 2.21 (s, 3H); $^{13}$C NMR (125 MHz, CDCl$_3$): δ 196.4, 143.4, 137.5, 137.2, 136.4, 135.9, 133.1, 130.0, 129.3, 128.9, 127.4, 127.3, 126.7, 50.0, 39.9, 29.3, 24.9, 21.4; HRMS (m/z): [M+H]$^+$ calcd. for C$_{20}$H$_{20}$NO$_3$SH, 390.0925. found, 390.0913.

26

Yellow solid, 78% yield, two steps; IR (film) $v_{max}$ 3030, 2917, 1667, 1160 cm$^{-1}$; $^1$H NMR (400 MHz, CDCl$_3$): δ 7.66 (d, J=8.0 Hz, 2H), 7.22 (d, J=8.0 Hz, 2H), 7.08 (d, J=8.4 Hz, 2H), 7.05 (d, J=8.4 Hz, 2H), 6.92-6.91 (m, 1H), 5.36 (dd, J=4.7, 2.6 Hz, 1H), 4.45 (d, J=18.5 Hz, 1H), 3.37 (ddd, J=18.5, 5.8, 3.5 Hz, 1H), 2.69-2.64 (m, 2H), 2.39 (s, 3H), 2.29 (s, 3H); $^{13}$C NMR (100 MHz, CDCl$_3$): δ 196.5, 143.3, 137.6, 137.3, 137.2, 136.3, 135.2, 129.6, 129.3, 127.1, 127.0, 52.0, 38.9, 27.7, 25.0, 21.5, 21.0; HRMS (m/z): [M+H]$^+$ calcd. for C$_{21}$H$_{23}$NO$_3$SH, 370.1471. found, 370.1469.

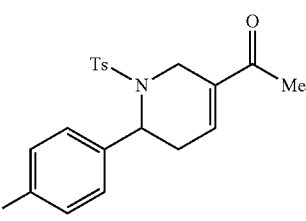

24

Yellow solid, 72% yield, two steps; IR (film) $v_{max}$ 3062, 2921, 1667, 1161 cm$^{-1}$; $^1$H NMR (400 MHz, CDCl$_3$): δ 7.61 (d, J=8.3 Hz, 2H), 7.21 (d, J=8.0 Hz, 2H), 7.18-7.14 (m, 2H), 6.93-6.88 (m, 3H), 5.33 (d, J=3.6 Hz, 1H), 4.44 (d, J=18.6 Hz, 1H), 3.34 (ddd, J=18.6, 5.6, 3.3 Hz, 1H), 2.64-2.63 (m, 2H), 2.37 (s, 3H), 2.20 (s, 3H); $^{13}$C NMR (100 MHz, CDCl$_3$): δ 196.5, 163.4, 160.9, 143.6, 137.1, 136.9, 136.8, 136.2, 134.1, 134.0, 129.7, 129.6, 128.9, 127.0, 126.7, 115.5, 115.3, 51.6, 38.9, 27.6, 25.0, 21.5; HRMS (m/z): [M+H]$^+$ calcd. for C$_{20}$H$_{20}$FNO$_3$SH, 374.1221. found, 374.1229.

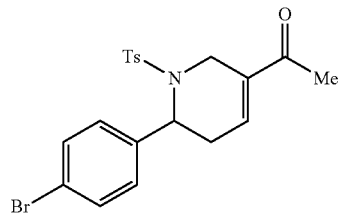

28

White solid, 61% yield, two steps; IR (film) $v_{max}$ 3057, 2917, 1667, 1160 cm$^{-1}$; $^1$H NMR (400 MHz, CDCl$_3$): δ 7.64 (d, J=8.0 Hz, 2H), 7.38 (d, J=8.4 Hz, 2H), 7.23 (d, J=8.0 Hz, 2H), 7.07 (d, J=8.4 Hz, 2H), 6.90-6.88 (m, 1H), 5.34 (t, J=3.9 Hz, 1H), 4.45 (d, J=18.6 Hz, 1H), 3.37 (ddd, J=18.6, 5.5, 3.2 Hz, 1H), 2.68-2.65 (m, 2H), 2.40 (s, 3H), 2.22 (s, 3H); $^{13}$C NMR (100 MHz, CDCl$_3$): δ 196.4, 143.6, 137.4, 137.0, 136.4, 136.3, 131.8, 129.7, 128.8, 127.1, 121.9, 51.7, 39.0, 27.6, 25.0, 21.5; HRMS (m/z): [M+H]$^+$ calcd. for C$_{20}$H$_{20}$BrNO$_3$SH, 434.0420. found, 434.0404.

29

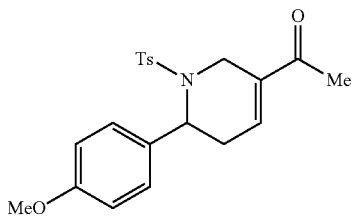

White solid, 65% yield, two steps; IR (film) $v_{max}$ 3064, 2925, 1665, 1159 cm$^{-1}$; $^1$H NMR (400 MHz, CDCl$_3$): δ 7.65 (d, J=8.0 Hz, 2H), 7.22 (d, J=8.0 Hz, 2H), 7.11 (d, J=8.8 Hz, 2H), 6.92-6.90 (m, 1H), 6.77 (d, J=8.8 Hz, 21-1), 5.34 (t, J=3.9 Hz, 1H), 4.44 (d, J=18.6 Hz, 1H), 3.76 (s, 3H), 3.36 (ddd, J=18.6, 5.5, 3.2 Hz, 1H), 2.67-2.65 (m, 2H), 2.39 (s, 3H), 2.23 (s, 3H); $^{13}$C NMR (100 MHz, CDCl$_3$): δ 196.5, 159.1, 143.3, 137.3, 137.1, 136.4, 130.2, 129.6, 128.3, 127.1, 113.9, 55.2, 51.7, 38.8, 27.9, 25.0, 21.5; HRMS (m/z): [M+Na]$^+$ calcd. for C$_{21}$H$_{23}$NO$_3$SNa, 408.1240. found, 408.1255.

30

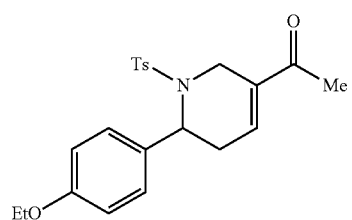

Yellow solid, 63% yield, two steps; IR (film) $v_{max}$ 3060, 2920, 1666, 1159 cm$^{-1}$; $^1$H NMR (400 MHz, CDCl$_3$): δ 7.64 (d, J=8.0 Hz, 2H), 7.22 (d, J=8.0 Hz, 2H), 7.09 (d, J=8.8 Hz, 2H), 6.91-6.90 (m, 1H), 6.76 (d, J=8.8 Hz, 2H), 5.33 (t, J=3.9 Hz, 1H), 4.44 (d, J=18.5 Hz, 1H), 3.98 (q, J=7.0 Hz, 2H), 3.35 (ddd, J=18.5, 5.6, 3.2 Hz, 1H), 2.67-2.64 (m, 2H), 2.39 (s, 3H), 2.23 (s, 3H), 1.38 (t, J=7.0 Hz, 3H); $^{13}$C NMR (100 MHz, CDCl$_3$): δ 196.6, 158.5, 143.3, 137.3, 137.2, 136.4, 130.0, 129.6, 128.3, 127.1, 114.4, 63.4, 51.7, 38.8, 27.9, 25.0, 21.5, 14.8; HRMS (m/z): [M+Na]$^+$ calcd, for C$_{22}$H$_{25}$NO$_4$SNa, 422.1397. found, 422.1393.

31

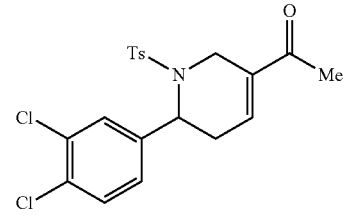

White solid, 58% yield, two steps; IR (film) $v_{max}$ 3062, 2923, 1668, 1161 cm$^{-1}$; $^1$H NMR (400 MHz, CDCl$_3$): δ 7.64 (d, J=8.0 Hz, 2H), 7.32 (d, J=8.4 Hz, 1H), 7.25 (d, J=8.0 Hz, 2H), 7.18 (dd, J=2.1, 0.4 Hz, 1H), 7.05 (ddd, J=8.4, 2.2, 0.6 Hz, 1H), 6.88-6.87 (m, 1H), 5.32 (d, J=4.0 Hz, 1H), 4.49 (dd, J=18.6, 1.1 Hz, 1H), 3.40 (ddd, J=18.6, 5.2, 2.9 Hz, 1H), 2.69-2.65 (m, 2H), 2.41 (s, 3H), 2.24 (s, 3H); $^{13}$C NMR (100 MHz, CDCl$_3$): δ 196.3, 143.8, 138.6, 136.9, 136.4, 136.0, 132.8, 132.0, 130.6, 129.8, 129.1, 127.0, 126.4, 51.4, 39.1, 27.6, 25.0, 21.5; HRMS (m/z): [M+H]$^+$ calcd, for C$_{20}$H$_{19}$Cl$_2$NO$_3$SH, 424.0535. found, 24.0530.

32

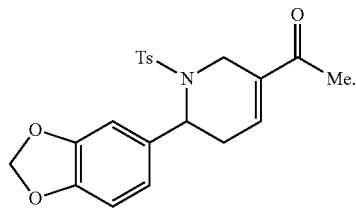

White solid, 63% yield, two steps; IR (film) $v_{max}$ 3062, 2892, 1666, 1160 cm$^{-1}$; $^1$H NMR (400 MHz, CDCl$_3$): δ 7.64 (d, J=8.0 Hz, 2H), 7.23 (d, J=8.0 Hz, 2H), 6.90-6.88 (m, 1H), 6.69-6.63 (m, 3H), 5.91 (s, 2H), 5.29-5.28 (m, 1H), 4.45 (d, J=18.5 Hz, 1H), 3.38 (ddd, J=18.5, 5.4, 3.0 Hz, 1H), 2.66-2.63 (m, 2H), 2.39 (s, 3H), 2.23 (s, 3H); $^{13}$C NMR (100 MHz, CDCl$_3$): δ 196.5, 147.9, 147.1, 143.4, 137.2, 137.0, 136.4, 132.1, 129.6, 127.0, 120.5, 108.0, 107.8, 101.2, 52.0, 38.8, 28.0, 25.0, 21.5; FIRMS (m/z): [M+H]$^+$ calcd. for C$_{21}$H$_{21}$NO$_5$SH, 400.1213. found, 400.1195.

33

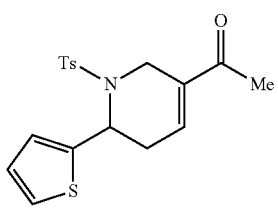

Yellow solid, 66% yield, two steps; IR (film) $v_{max}$ 3068, 2921, 1667, 1162 cm$^{-1}$; $^1$H NMR (400 MHz, CDCl$_3$): δ 7.60 (d, J=8.0 Hz, 2H), 7.18 (d, J=8.0 Hz, 2H), 7.09 (dd, J=4.9, 1.4 Hz, 1H), 6.90-6.88 (m, 1H), 6.81-6.77 (m, 1H), 5.59 (d, J=3.2 Hz, 1H), 5.43 (d, J=6.6 Hz, 1H), 4.42 (dd, J=18.2, 0.6 Hz, 1H), 3.57-3.50 (m, 1H), 2.85-2.76 (m, 1H), 2.68-2.61 (m, 1H), 2.34 (s, 3H), 2.22 (s, 3H); $^{13}$C NMR (100 MHz, CDCl$_3$): δ 196.6, 143.6, 141.2, 136.6, 136.5, 135.9, 129.6, 127.2, 126.6, 125.9, 125.4, 49.0, 39.2, 30.7, 25.0, 21.5; —FIRMS (m/z): [M+Na]$^+$ calcd. for C$_{18}$H$_{19}$NO$_3$S$_2$Na, 384.0699. found, 384.0703.

34

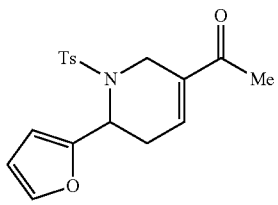

Yellow solid, 59% yield, two steps; IR (film) $v_{max}$ 3120, 2925, 1667, 1162 cm$^{-1}$; $^1$H NMR (400 MHz, CDCl$_3$): δ 7.64 (d, J=8.0 Hz, 2H), 7.21 (d, J=8.0 Hz, 2H), 7.13 (dd, J=1.8, 0.7 Hz, 1H), 6.91-6.88 (m, 1H), 6.15 (dd, J=3.2, 1.8 Hz, 1H), 5.93 (d, J=3.2 Hz, 1H), 5.43 (d, J=6.8 Hz, 1H), 4.40 (dd, J=17.6, 0.8 Hz, 1H), 3.45-3.39 (m, 1H), 2.88-2.79 (m, 1H), 2.69-2.62 (m, 1H), 2.37 (s, 3H), 2.25 (s, 3H); $^{13}$C NMR (100 MHz, CDCl$_3$): δ 196.6, 151.5, 143.4, 142.0, 136.6, 136.3, 135.8, 129.4, 127.4, 110.2, 107.7, 47.3, 39.7, 29.3, 25.0, 21.5; HRMS (m/z): [M+Na]⁺ calcd. for $C_{18}H_{19}NO_4SNa$, 368.0927. found, 368.0923.

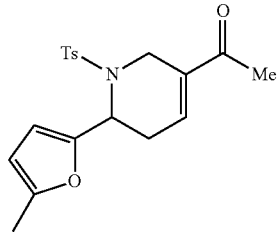

35

Yellow solid, 56% yield, two steps; IR (film) $v_{max}$ 3062, 2917, 1667, 1162 cm⁻¹; ¹H NMR (400 MHz, CDCl₃): δ 7.68 (d, J=8.2 Hz, 2H), 7.22 (d, J=8.2 Hz, 2H), 6.92-6.90 (m, 1H), 5.79 (d, J=3.0 Hz, 1H), 5.71 (d, J=3.0 Hz, 1H), 5.37 (d, J=6.8 Hz, 1H), 4.43 (d, J=17.4 Hz, 1H), 3.42-3.35 (m, 1H), 2.89-2.80 (m, 1H), 2.68-2.62 (m, 1H), 2.38 (s, 3H), 2.26 (s, 3H), 2.02 (s, 3H); ¹³C NMR (100 MHz, CDCl₃): δ 196.6, 151.7, 149.5, 143.2, 136.8, 136.6, 136.0, 129.3, 127.5, 108.4, 106.0, 47.5, 39.6, 29.4, 25.0, 21.5, 13.3; HRMS (m/z): [M+Na]⁺ calcd. for $C_{19}H_{21}NO_4SNa$, 382.1084. found, 382.1071.

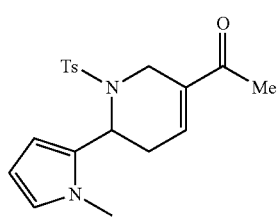

36

Yellow solid, 58% yield, two steps; IR (film) $v_{max}$ 3057, 2921, 1666, 1161 cm⁻¹; NMR (400 MHz, CDCl₃): δ 7.63 (d, J=8.0 Hz, 2H), 7.21 (d, J=8.0 Hz, 2H), 6.70-6.69 (m, 1H), 6.58 (t, J=2.2 Hz, 1H), 5.93 (dd, J=3.6, 2.8 Hz, 1H), 5.83 (ddd, J=3.6, 1.6, 0.5 Hz, 1H), 5.37 (t, J=3.9 Hz, 1H), 4.47 (d, J=18.7 Hz, 1H), 3.73 (s, 3H), 3.29 (ddd, J=18.7, 5.9, 3.4 Hz, 1H), 2.54-2.51 (m, 2H), 2.38 (s, 3H), 2.15 (s, 3H); ¹³C NMR (100 MHz, CDCl₃): δ 196.5, 143.6, 137.1, 135.8, 129.6, 129.5, 128.2, 127.1, 123.6, 108.4, 106.5, 46.5, 38.7, 34.3, 27.2, 24.9, 21.5; FIRMS (m/z): [M+H]⁺ calcd. for $C_{19}H_{22}N_2O_3SH$, 359.1424. found, 359.1415.

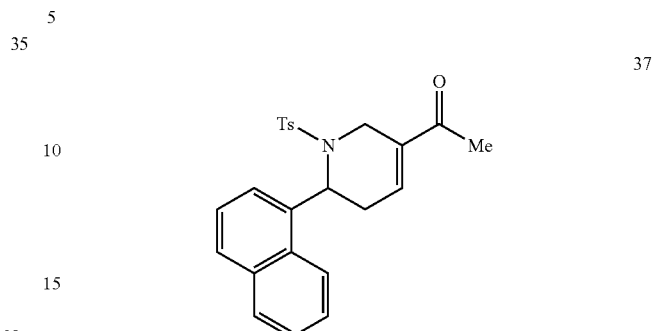

37

White solid, 78% yield, two steps; IR (film) $v_{max}$ 2979, 2917, 1709, 1166 cm⁻¹; ¹H NMR (500 MHz, CDCl₃): δ 8.59 (d, J=8.5 Hz, 1H), 7.85 (d, J=8.1 Hz, 1H), 7.78 (d, J=8.1 Hz, 1H), 7.68 (d, J=8.2 Hz, 2H), 7.62 (t, J=7.3 Hz, 1H), 7.52 (t, J=7.5 Hz, 1H), 7.28 (t, J=7.7 Hz, 1H), 7.18-7.16 (m, 3H), 6.96 (t, J=2.3 Hz, 1H), 6.22 (d, J=7.2 Hz, 1H), 4.34 (d, J=18.8 Hz, 1H), 3.22 (dd, J=18.8, 2.6 Hz, 1H), 2.96 (dd, J=20.0, 3.0 Hz, 1H), 2.75 (ddd, J=20.0, 4.8, 2.3 Hz, 1H), 2.36 (s, 3H), 2.23 (s, 3H); ¹³C NMR (125 MHz, CDCl₃): δ 196.9, 143.6, 137.8, 136.4, 136.1, 134.0, 133.4, 133.3, 129.4, 129.2, 128.7, 127.5, 126.8, 125.9, 124.5, 124.0, 123.9, 49.0, 38.8, 27.9, 24.9, 21.4; HRMS (m/z): [M+H]⁺ calcd, for $C_{24}H_{23}NO_3SH$, 406.1471. found, 406.1458.

From the forgoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional application 61/432,650, filed Jan. 14, 2011, and in the figures, are hereby incorporated by reference in their entirety, particularly with regard to the specific findings for which they are referenced herein.

We claim:

1. A pharmaceutical composition comprising a compound of formula I or a pharmaceutically acceptable salt or solvate thereof and a pharmaceutically acceptable carrier,

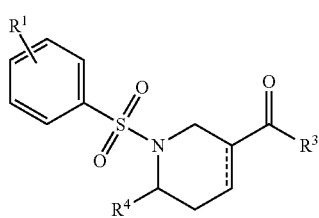

Formula I wherein
the dashed bond indicates that a double bond may be present at the indicated location, or the ring may be saturated,
$R^1$ may be at any position on the phenyl ring and is hydrogen, halogen, nitro, $(C_1-C_4)$alkyl, $(C_1-C_4)$haloalkyl, O—$(C_1-C_4)$alkyl (alkoxy), S—$(C_1-C_4)$alkyl (alkylthio) or NH—$(C_1-C_4)$alkyl (alkylamino),
$R^4$ is hydrogen, halogen, nitro, $(C_1-C_4)$alkyl, $(C_1-C_4)$haloalkyl, O—$(C_1-C_4)$alkyl (alkoxy), S—$(C_1-C_4)$alkyl (alkylthio), NH—$(C_1-C_4)$alkyl (alkylamino), or Ar;
Ar is phenyl, pyridine, or thiophene which may bear one or more substituents $R^2$,
$R^2$ may be at any available position on the aromatic or heteroaromatic moiety Ar and is hydrogen, halogen, nitro, $(C_1-C_4)$alkyl, $(C_1-C_4)$haloalkyl, O—$(C_1-C_4)$alkyl (alkoxy), S—$(C_1-C_4)$alkyl (alkylthio) or NH—$(C_1-C_4)$alkyl (alkylamino), except when $R^2$ is in the para-position of a 6-membered ring, in the para-position, $R^2$ is hydrogen or methyl, and
$R^3$ is $(C_1-C_6)$alkyl, $(C_1-C_6)$haloalkyl, O—$(C_1-C_6)$alkyl, NH—$(C_1-C_6)$alkyl, $(C_1-C_6)$alkenyl, O—$(C_1-C_6)$alkenyl, or NH—$(C_1-C_6)$alkenyl, $(C_1-C_6)$alkynyl, O—$(C_1-C_6)$alkynyl, NH—$(C_1-C_6)$alkynyl, S—$(C_1-C_6)$alkyl, S—$(C_1-C_6)$alkenyl, or S—$(C_1-C_6)$alkynyl.

2. The pharmaceutical composition of claim 1, wherein the compound of Formula I has the structure of Formula II, and is known as aplexone

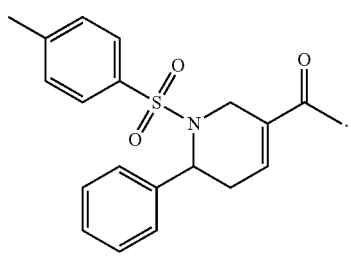

Formula II

3. The pharmaceutical composition of claim 1, wherein the compound of Formula I is one of the following compounds:

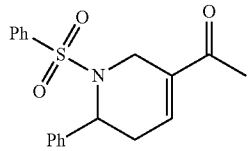

17

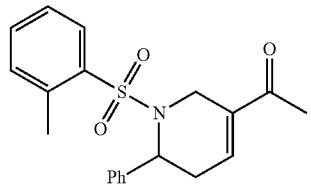

18

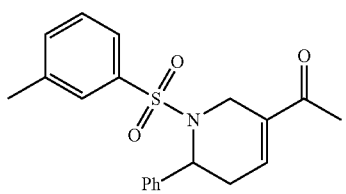

19

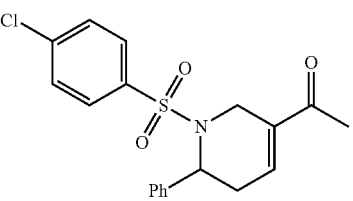

20

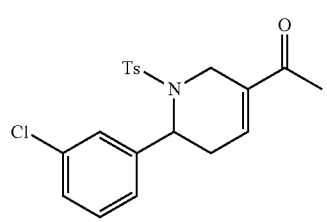

21

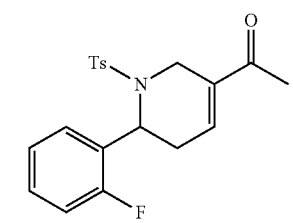

22

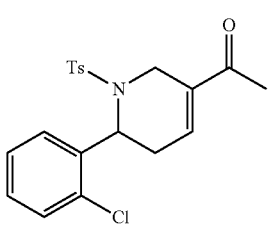

23

-continued
24
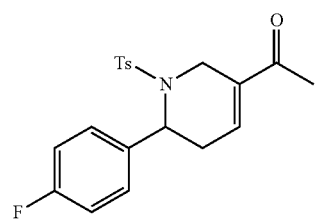
25
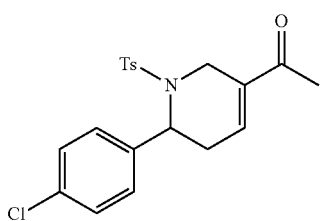
26
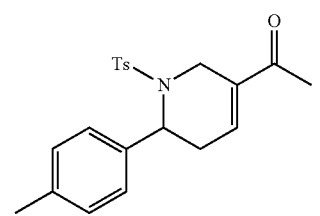
27
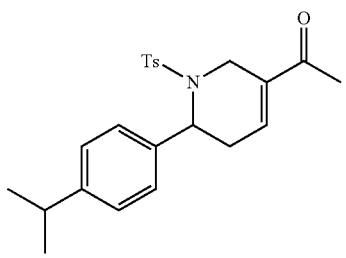
28
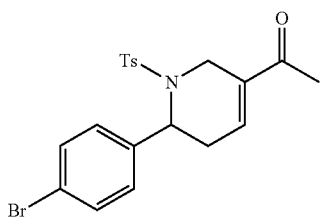
29
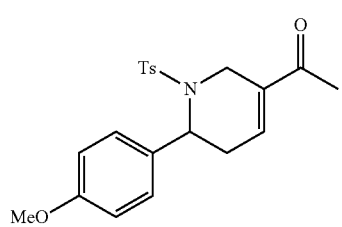
30
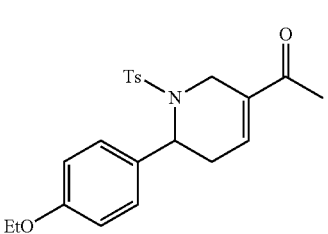
-continued
31
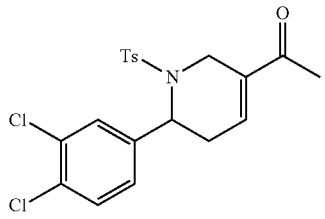
32
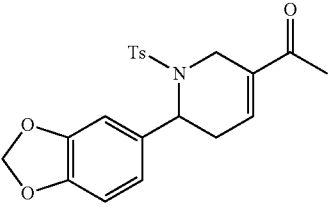
33
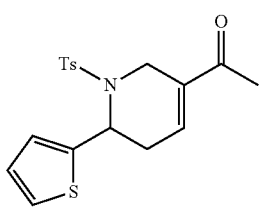
34
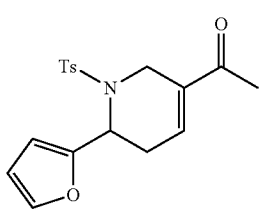
35
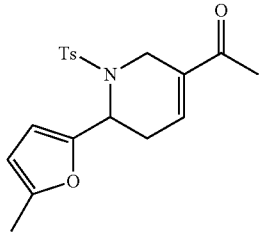
36
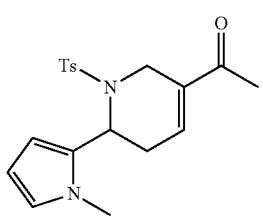
37
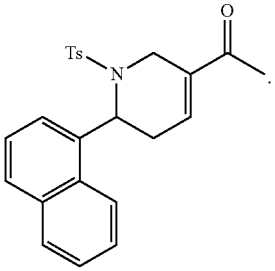

4. The pharmaceutical composition of claim 1, wherein the compound of Formula I is represented by Formula III,

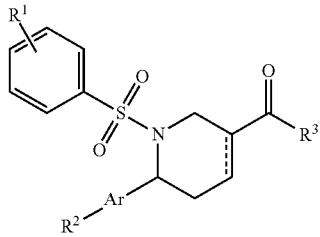

Formula III wherein
the dashed bond indicates that a double bond may be present at the indicated location, or the ring may be saturated,
$R^1$ may be at any position on the phenyl ring and is hydrogen, halogen, nitro, $(C_1$-$C_4)$alkyl, $(C_1$-$C_4)$haloalkyl, O—$(C_1$-$C_4)$alkyl (alkoxy), S—$(C_1$-$C_4)$alkyl (alkylthio) or NH—$(C_1$-$C_4)$alkyl (alkylamino), Ar is phenyl, pyridine, or thiophene which may bear one or more substituents $R^2$, $R^2$ may be at any available position on the aromatic or heteroaromatic moiety Ar and is hydrogen, halogen, nitro, $(C_1$-$C_4)$alkyl, $(C_1$-$C_4)$haloalkyl, O—$(C_1$-$C_4)$alkyl (alkoxy), S—$(C_1$-$C_4)$alkyl (alkylthio) or NH—$(C_1$-$C_4)$alkyl (alkylamino), except when $R^2$ is in the para-position of a 6-membered ring. In the para-position, $R^2$ is hydrogen or methyl, and $R^3$ is $(C_1$-$C_6)$alkyl, $(C_1$-$C_6)$haloalkyl, O—$(C_1$-$C_6)$alkyl, NH—$(C_1$-$C_6)$alkyl, $(C_1$-$C_6)$alkenyl, O—$(C_1$-$C_6)$alkenyl, or NH—$(C_1$-$C_6)$alkenyl, $(C_1$-$C_6)$alkynyl, O—$(C_1$-$C_6)$alkynyl, NH—$(C_1$-$C_6)$alkynyl, S—$(C_1$-$C_6)$alkyl, S—$(C_1$-$C_6)$alkenyl, or S—$(C_1$-$C_6)$alkynyl.

5. The pharmaceutical composition of claim 1, which further comprises another agent for cancer treatment or another agent for lowering cellular cholesterol levels.

6. A kit comprising the pharmaceutical composition of claim 1, wherein the components are packaged in one or more containers.

* * * * *

SEQUENCE LISTING

<160> NUMBER OF SEQ ID NOS: 20

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgaagagtcg ggcaacactg atgt                                          24

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 2
gcaatatcac cagcaacaac cagagc                                          26

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctttggcca agtttgctct gagt                                            24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tccacgaggg catcaagagt gaaa                                            24

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatcctgttc tcagtgatgc cctcaa                                          26

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acttcctcag ttggcagctc agat                                            24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttcagacgga gagatcgagc acat                                            24

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 8
tctcggtatc ttctctgcgc ttcttg                                      26

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggaagtgctt caagatgctg ctgt                                        24

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtgtcccagt cataagggat gctgaa                                      26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taagcagcag gagctgtatg gttacg                                      26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtcttcaggt accaggcttc attcca                                      26

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agaggaagtg ctggacacgc tatt                                        24

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 14
cgcttgaact tgtgtggttc tccaag                                          26

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgtgatggga gtcaaccagg acaa                                            24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttagccagag gagccaagca gtta                                            24

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggatccacca tggtgagcaa gggcgag                                         27

<210> SEQ ID NO 18
<211> LENGTH: 87
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaattctcac aagacaaggc acccagattt tttcttccca cgtctagctt gcagagcagc     60
tctcgtcttg tacagctcgt ccatgcc                                         87

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acgtcggatc caccatggtg agcaagg                                         27

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 20
acgtcgaatt caggagagca cacacttgc                                29
```